US011065346B2

(12) United States Patent
Hasenpusch et al.

(10) Patent No.: US 11,065,346 B2
(45) Date of Patent: *Jul. 20, 2021

(54) RNA FOR USE IN THE TREATMENT OF LIGAMENT OR TENDON LESIONS

(71) Applicant: ethris GmbH, Planegg (DE)

(72) Inventors: Günther Hasenpusch, Munich (DE); Carsten Rudolph, Krailling (DE)

(73) Assignee: ethris GmbH, Planegg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,191

(22) Filed: Apr. 29, 2019

(65) Prior Publication Data

US 2019/0381193 A1 Dec. 19, 2019

Related U.S. Application Data

(63) Continuation of application No. 15/326,332, filed as application No. PCT/EP2015/066329 on Jul. 16, 2015, now Pat. No. 10,272,161.

(30) Foreign Application Priority Data

Jul. 16, 2014 (EP) ..................................... 14177302

(51) Int. Cl.
*A61K 48/00* (2006.01)
*A61K 31/7105* (2006.01)
*A61K 38/18* (2006.01)
*A61K 9/00* (2006.01)

(52) U.S. Cl.
CPC ........ *A61K 48/0016* (2013.01); *A61K 9/0019* (2013.01); *A61K 31/7105* (2013.01); *A61K 38/1875* (2013.01); *A61K 48/005* (2013.01); *A61K 48/0066* (2013.01); *A61K 48/0075* (2013.01)

(58) Field of Classification Search
None
See application file for complete search history.

(56) References Cited

U.S. PATENT DOCUMENTS

| | | | |
|---|---|---|---|
| 10,272,161 B2 * | 4/2019 | Hasenpusch | A61K 48/0075 |
| 2003/0073637 A1 | 4/2003 | Uutela et al. | |
| 2006/0030695 A1 | 2/2006 | Uutela et al. | |
| 2008/0261888 A1 | 10/2008 | Uutela et al. | |
| 2008/0267873 A1 * | 10/2008 | Hoerr | A61P 37/02 |
| | | | 424/9.1 |

FOREIGN PATENT DOCUMENTS

WO WO 2007/103787 A2 9/2007

OTHER PUBLICATIONS

Ruan, Hongjiang, et al. "Prevention of tendon adhesions by ERK2 small interfering RNAs." *International journal of molecular sciences* 14.2 (2013): 4361-4371.
Ozeki, Nobutake, et al. "Transplantation of Achilles tendon treated with bone morphogenetic protein 7 promotes meniscus regeneration in a rat model of massive meniscal defect," *Arthritis & Rheumatism* 65.11 (2013): 2876-2886.
Schiffelers, Raymond M., et al. "Effects of treatment with small interfering RNA on joint inflammation in mice with collagen-induced arthritis." *Arthritis & Rheumatism* 52.4 (2005): 1314-1318.
Suwalski, Arnaud, et al. "Accelerated Achilles tendon healing by PDGF gene delivery with mesoporous silica nanoparticles." *Biomaterials* 31.19 (2010): 5237-5245.
Ryan, Alice S., et al. "Skeletal muscle hypertrophy and muscle myostatin reduction after resistive training in stroke survivors." *Stroke* 42.2 (2011): 416-420.
Phua, Kyle KL, Kam W. Leong, and Smita K. Nair. "Transfection efficiency and transgene expression kinetics of mRNA delivered in naked and nanoparticle format." *Journal of Controlled Release* 166.3 (2013): 227-233.
Kormann, Michael SD, et al. "Expression of therapeutic proteins after delivery of chemically modified mRNA in mice." *Nature biotechnology* 29.2 (2011): 154-157.
International Search Report for International Application No. PCT/EP2015/066329, dated Oct. 16, 2015.
Notice of Allowance issued in U.S. Appl. No. 15/326,332 dated Dec. 10, 2018.
Non Final Office Action issued in U.S. Appl. No. 15/326,332 dated Mar. 9, 2018.

* cited by examiner

*Primary Examiner* — Robert M Kelly
(74) *Attorney, Agent, or Firm* — Morse, Barnes-Brown & Pendleton, P.C.; Lisa M. Warren, Esq.; Erin E. Bryan, Esq.

(57) ABSTRACT

Described is a liquid composition containing naked RNA, such as mRNA encoding a polypeptide, for use in the treatment or prevention of ligament or tendon lesions as well as a method for treating ligament or tendon lesions comprising the administration of a liquid composition containing naked RNA, such as mRNA encoding a polypeptide, which is beneficial in the process of healing the ligament or tendon lesions.

9 Claims, 25 Drawing Sheets
(16 of 25 Drawing Sheet(s) Filed in Color)
Specification includes a Sequence Listing.

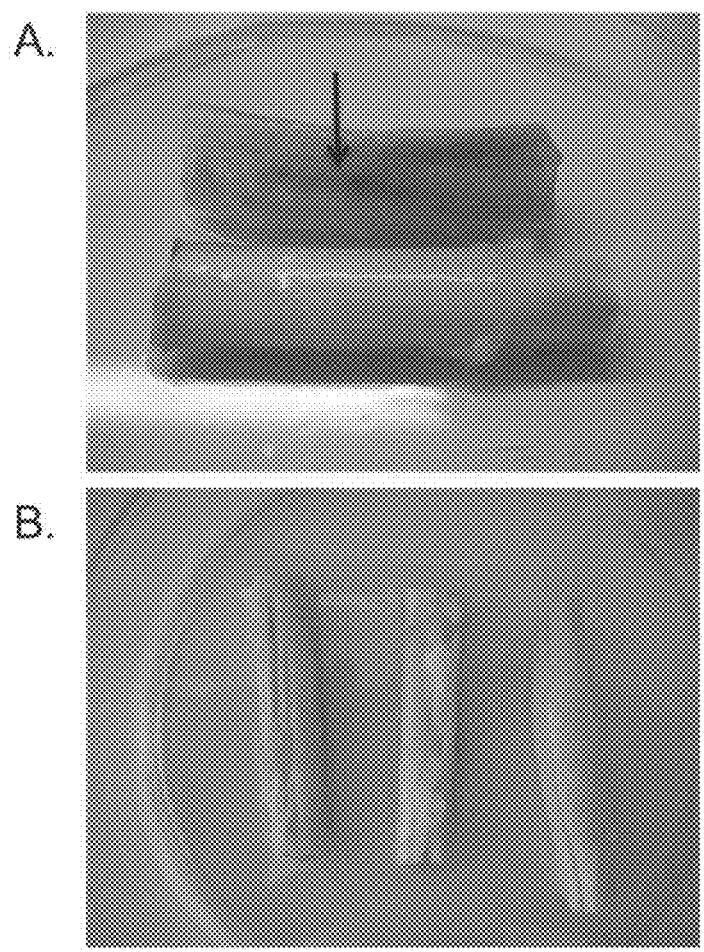
Figure 11 A-B

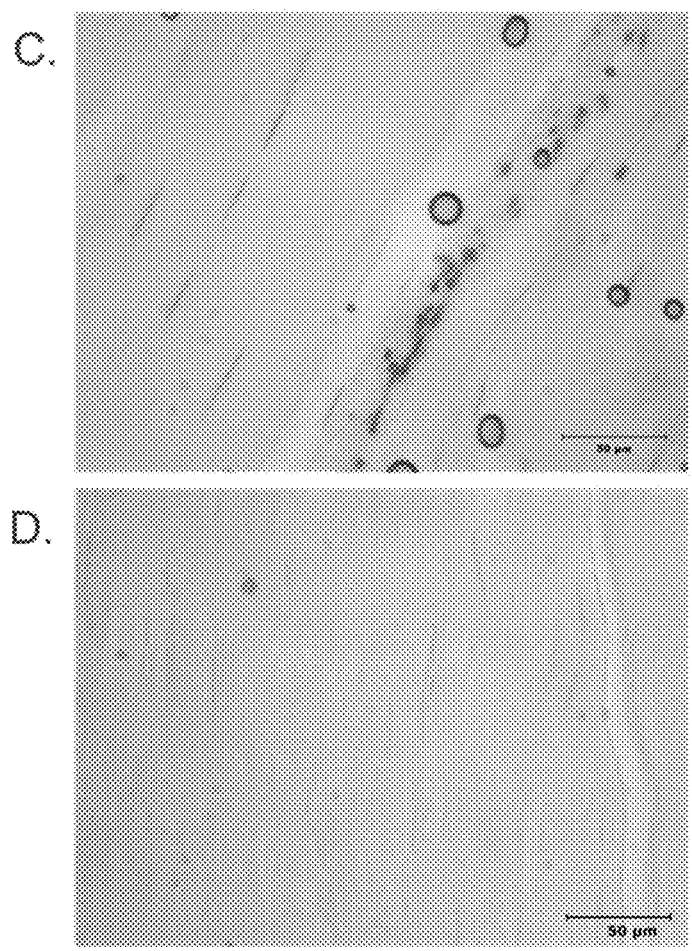
Figure 11 C-D

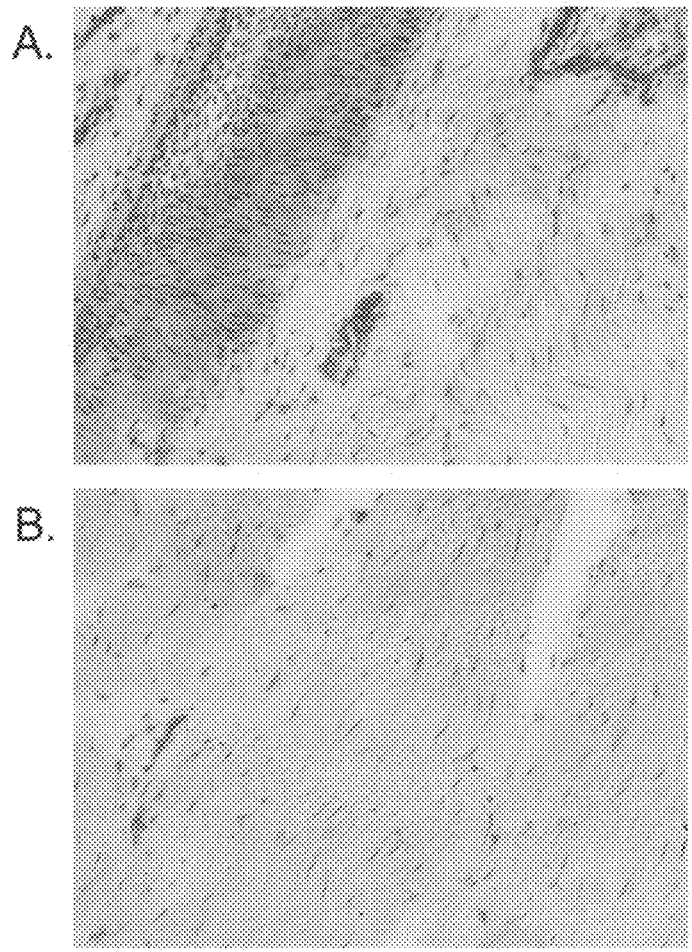
Figure 12 A-B

RNA FOR USE IN THE TREATMENT OF LIGAMENT OR TENDON LESIONS

CROSS-REFERENCE OF RELATED APPLICATIONS

This application is a continuation of U.S. application Ser. No. 15/326,332 (U.S. Pat. No. 10,272,161), filed Jan. 13, 2017, which is a United States National Stage under 35 U.S.C. § 371 of International Application No. PCT/EP2015/066329, filed Jul. 16, 2015, which claims the benefit of European Application No. 14177302.8, filed Jul. 16, 2014. The content of each of the aforementioned patent applications is hereby incorporated by reference in their entirety. International Application No. PCT/EP2015/066329 was published under PCT Article 21(2) in English.

The present invention relates to a liquid composition containing naked RNA, such as mRNA encoding a polypeptide for use in the treatment or prevention of ligament or tendon lesions. The present invention also relates to a method for treating ligament or tendon lesions comprising the administration of a liquid composition containing naked RNA, such as mRNA encoding a polypeptide which is beneficial in the process of healing the ligament or tendon lesions.

Ligaments are dense fibrous tissue structures composed primarily of highly oriented and tightly packed collagen fibrils. Due to this specialized matrix organization, ligaments possess large tensile strength and flexibility. At the same time, ligament injuries are one of the most common injuries to joints. Tendons have a crucial role in maintaining the body mechanics, as their main function is to connect muscles to bones. They are axial connective tissues that ensure transmission of the traction exerted by muscle to bone resulting in joint movements. Tendons are composed of a few cells and parallel arrays of collagen fibers. Their important mechanical function renders them liable to injury and rupture. Such injuries can be caused by different origins, such as trauma, overuse, consequence of metabolic disease or age-related loss of elasticity. Normally, ligaments and tendon may heal spontaneously but their regeneration is very difficult and requires a very long period, i.e. several months and sometimes even a year. Although the natural healing or an efficient surgical repair mostly permits restoration of satisfactory function, it often fails to restore the complete biological and biomechanical characteristics of an uninjured tissue. The healed ligament or tendon remains mechanically weak and susceptible to re-injury. Other lesions like tendinosis feature degenerative changes where all components of the tendon are affected (tenocytes, extracellural matrix and collagen). Where natural healing is insufficient, many of the ligament or tendon lesions continue to present clinical problems defying medical and surgical treatments. The failure to obtain optimal healing conditions led to new approaches taking into consideration advances in the comprehension of the ligament's or tendon's healing process at the cellular and molecular level. In the case of tendon healing this healing process consists of successive phases: clot formation, inflammation, proliferation, remodeling and maturation (Frank, C B, J. Am. Acad. Orthop. Surgeons 4 (1996), 74-83). Several growth factors and cytokines have been shown to play a role in the tendon repair process (Evans, C H, Sports Med. 28 (1999), 71-76). They act on vascular growth, cell migration, cell proliferation as well as collagen and extracellular protein synthesis. In order to optimize the healing process of ligament or tendon lesions, different approaches have been developed in order to deliver growth factors locally, in particular via gene transfer. Nakamura et al. (J. Clin. Invest. 97 (1996), 226-231) describes the transient introduction of a plasmid carrying a reporter gene (β-gal) into the healing rat patellar ligament so as to study the ligament's biology. The introduction of the plasmid DNA was achieved by using hemagglutinating virus of Japan (HVJ)-liposome mediated gene transfer. The same group reported subsequently that they had been able to introduce with the same technique a plasmid encoding platelet-derived growth factor (PDGF)-B into healing patellar ligament (Nakamura et al., Gene Therapy 5 (1998), 1165-1170). The liposome suspension was injected directly into the injured patellar ligament of rats and an enhanced expression of PDGF-B in healing ligament could be observed up to 4 weeks after transfection leading to an initial promotion of angiogenesis and subsequent enhanced collagen deposition. Özkan et al. (Eur. J. Clin. Invest. 29 (1999), 63-67) describes the direct in vivo gene transfer of a plasmid DNA containing the reporter gene β-gal into healing patellar ligament by intra-arterial delivery of HVJ-liposomes. In 2000, Goomer et al. (Clinical Orthopaedics and Related Research 379S (2000), S189-S200) reported on a non-viral in vivo gene transfer method for introducing plasmid DNA containing the β-gal, TGF-β1 or PTHrP gene into cartilage or tendon tissue. Jayankura et al. (J. Gene Med. 5 (2003), 618-624) report on in situ gene transfer into animal tendons by injection of naked DNA and electrotransfer. Gene expression was exclusively observed in cells adjacent to the injection site and along the needle track, indicating that the plasmid could not diffuse through the dense tendon and that the transduced cells do not migrate over time. Another non-viral delivery method of plasmid DNA to tendon tissue was reported by Delalande et al. (Ultrasonics 50 (2010), 269-272 and J. Controlled Release 156 (2011), 223-230). The authors introduced a plasmid encoding luciferase or human fibromodulin into tendon tissue of mice using microbubbles and untrasound-assisted gene transfer. Suwalski et al. (Biomaterials 31 (2010), 5237-5245) describes the possibility to accelerate Achilles tendon healing by introducing a plasmid encoding PDGF via mesoporous silica nanoparticles. A further approach was described in Qui et al. (Gene Therapy 19 (2012), 703-710) using ultrasound-targeted microbubble destruction in order to enhance naked plasmid DNA transfection in rabbit Achilles tendons in vivo. In view of the intended use of gene therapy approaches in the context of healing lesions of ligaments and tendons in the clinic, it would be desirable to have at hand methods for applying the desired proteins in the form of nucleic acids which allow an easy handling.

The present application addresses this need by providing the embodiments as defined in the claims.

In particular, the present inventors have surprisingly found that it is possible to effectively deliver and express RNA, in particular mRNA encoding a polypeptide, to ligament or tendon tissue thereby allowing the expression of the desired polypeptide in the ligament or tendon tissue. The RNA is present in naked form in a liquid composition. This liquid composition can be delivered directly into ligament or tendon tissue, e.g. by injection, and there is no need for any gene transfer vectors or carriers for the RNA or methods for enhancing the transfer into the tissue like electrotransfer or ultrasound. Accordingly, the present invention allows for an easy way to deliver proteins by way of gene therapy via mRNA to ligament or tendon tissue which can be effectively implement in the clinic. Moreover, it was observed that expression of a protein encoded by an injected RNA is not only observed directly at the site of injection but also at more distant locations in the tendon. More particular, the injection of naked RNA, in particular naked chemically modified mRNA (cmRNA), in glucose-containing solution into tendons was shown to result in high protein expression in healthy and (experimentally) injured tendons. For example, the injection of BMP-7 encoding cmRNA was shown to result in increased BMP-7 protein expression, less fulminant degradation of collagen type I, decreased collagen type III formation as well as trends towards higher collagen I/III ratio and chemotactic cell attraction in surgically dissected tendons. Furthermore, it was found that overexpression of BMP-7 especially during the inflammatory phase of tendon regeneration positively influences healing.

In comparison to DNA, RNA has the advantage that it prevents the risk of insertional mutagenesis and, consequently, genotoxicity. Moreover, the RNA, in particular cmRNA, to be employed in the context of the invention was shown to have excellent biological compatibility in vivo when injected locally into ligaments or tendons. For example, it was shown in the context of the invention that injection of RNA, in particular cmRNA, into either intact or injured tendons resulted in local and distinct protein expression. The respectively expressed proteins were biologically functional.

Thus, in a first embodiment the present invention relates to a liquid composition containing naked RNA for use in the treatment or prevention of ligament or tendon lesions (in a patient). It is particularly envisaged that the liquid composition of the invention is a liquid pharmaceutical composition.

The appended Examples show that it is possible to efficiently express proteins from mRNA in tendon tissue according to the present invention. However, the teaching of the present invention is not restricted to the use of an RNA encoding a polypeptide. In the context of the present invention it is also possible to employ other kinds of RNA molecules, e.g. noncoding RNA, as will be explained further below.

A ligament is the fibrous tissue that connects bones to other bones and is also known as articular ligament, articular larua, fibrous ligament, or true ligament. Thus, the term "ligament" refers to a band of tough, fibrous dense regular connective tissue bundles, made of attenuated collagenous fibers; with said bundles protected by dense irregular connective tissue sheaths. Ligaments connect bones to other bones in order to stabilize joints. They do not connect muscles to bones; which is the function of tendons. Some ligaments limit the mobility of articulations, or prevent certain movements altogether.

The term "tendon" (or sinex) refers to a tough band of fibrous connective tissue that usually connects muscle to bone and is capable of withstanding tension. Tendons and muscles work together to move bones.

The term "lesion" refers to any kind of damage to the ligament or tendon which has a negative effect on its function, in particular a decrease in resilience, fracture toughness and/or tensile strength. A lesion can, e.g., be tissue inflammation with or without necrotic areas due to overuse, degeneration, a disease state, the cause of age, such as an age-related loss of function or elasticity, of an injury or a rupture. Moreover surgically dissected healthy tendons and ligaments which are proposed to be used as autologous or allogenic transplants for reconstructing diseased or ruptured tendons and ligaments are as well considered as lesioned, though a lesion-like state is generated as a consequence to the surgical procedure. It is, in principle, envisaged in the context of the invention to treat (or prevent) any ligament or tendon injury or damage, any (degenerative) ligament or tendon disease or disorder and any (degenerative) ligamentopathy and (degenerative) tendinopathy.

In principle, a ligament or tendon lesion, a ligament or tendon injury or damage, a (degenerative) ligament or tendon disease or disorder or (degenerative) ligamentopathy and (degenerative) tendinopathy can develop in any tendon and ligament, respectively, of the body.

In a specific aspect, there is the problem that the healing/regeneration rate in the tendon/ligament is less than the injury/overload rate. In other words, there may be a tendon/ligament disrepair due to repetitive overloading. This leads to degeneration processes in the tendon/ligament. As such, tendinopathy/ligamentopathy is progressively worsening with the continued (over)use (of the affected joint/muscle(s)). Lateral epicondylosis, also known as lateral epicondylitis and "tennis elbow", respectively, is a common example of such a tendinopathy. It is characterized by lateral elbow pain caused by overuse. It affects about two percent of the population, mainly in the fourth and fifth decades. From a pathomechanical perspective, the forearm muscles and tendons become damaged from overuse, e.g. through repeating the same motions again and again. Furthermore, also intrinsic factors are associated with the risk of suffering from (degenerative) tendiopathy/ligamentopathy. These factors are factors like age, sex, obesity, and/or type II diabetes mellitus (Ribbans, Bone Joint J. 95-B, 2013, 305-313). While muscle fibers have high healing potential, ligament/tendon fibers are relatively avascular, less well supported by blood and tend to heal only very slowly. As a consequence, there may be a progressive inflammation (due to overuse); in case of the lateral epicondylosis, progressive inflammation of the tendons that join the forearm muscles on the outside of the elbow. The tendon usually involved in lateral epicondylosis is called Extensor Carpi Radialis Brevis.

The most common short term therapy for lateral epicondylosis is the injection of anti-inflammatory drugs such as corticosteroids into the soft tissue surrounding the elbow. Although studies support their efficacy for short-term pain relief, they do not demonstrate long term benefit or healing. In another injection therapy autologous blood or platelet-rich plasma is injected. However, also these injection therapies do not show better efficacy over time than corticosteroid therapy.

It is clear from the above that there is also the need of prophylaxis and prevention, respectively, of a ligament or tendon lesion, a ligament or tendon injury or damage, a (degenerative) ligament or tendon disease or disorder or (degenerative) ligamentopathy and (degenerative) tendinopathy like, for example, lateral epicondylosis. Hence, in one embodiment, the present invention provides for such a prophylaxis and prevention, respectively, like, for example, prophylaxis/prevention of lateral epicondylosis. In particular, the present invention provides for the liquid composition containing naked RNA of the invention for use in preventing a ligament or tendon lesion, a ligament or tendon injury or damage, a (degenerative) ligament or tendon disease or disorder or (degenerative) ligamentopathy and (degenerative) tendinopathy. What has been said herein elsewhere with respect to the mode of administration applies here, mutatis mutandis. In particular, it is envisaged that the liquid composition containing naked RNA in accordance with the invention is delivered directly into the tendon/ligament tissue (e.g. by injection).

In yet another embodiment the present invention provides for prophylaxis and prevention, respectively, of the progression of a ligament or tendon lesion, a ligament or tendon injury or damage, a (degenerative) ligament or tendon disease or disorder or (degenerative) ligamentopathy and (degenerative) tendinopathy, respectively, like, for example, prophylaxis/prevention of the progression of lateral epicondylosis. In particular, the present invention provides for the liquid composition containing naked RNA of the invention for use in prophylaxis and prevention, respectively, of the progression of a ligament or tendon lesion, a ligament or tendon injury or damage, a (degenerative) ligament or tendon disease or disorder or (degenerative) ligamentopathy and (degenerative) tendinopathy. Again, what has been said herein elsewhere with respect to the mode of administration applies here, mutatis mutandis. In particular, it is envisaged that the liquid composition containing naked RNA in accordance with the invention is delivered directly into the tendon/ligament tissue (e.g. by injection).

In a specific aspect, the prophylaxis and prevention, respectively, in accordance with the invention may start once (a) first symptom(s) have/has been observed. For example, such a symptom is pain and/or tenderness (for example pain and/or tenderness in the bony knob on the outside of the elbow in the case of lateral epicondylosis).

In any case, Lateral epicondylosis is a prominent, however non-limiting, example of a ligament/tendon lesion and (degenerative) ligamentopathy/tendinopathy, respectively, to be treated in accordance with the invention.

The term "naked RNA" means that the RNA is not complexed to any kind of other compound, in particular proteins, peptides, polymers, like cationic polymers, lipids, liposomes, viral vectors or the like. Thus, "naked RNA" means that the RNA is present in the liquid composition in a free and uncomplexed form being molecularly dispersed in solution. For example, it is not envisaged that the "naked RNA" is complexed with a lipid and/or polymer carrier system/transfection reagent like, for example, DreamFect™ Gold or (branched) PEI. Hence, the liquid composition of the invention does, for example, not contain a lipid and/or polymer carrier system/transfection reagent like, for example, DreamFect™ Gold or (branched) PEI.

According to the present invention the naked RNA is present in a liquid composition which is used for application to the ligament or tendon tissue. A liquid composition is any composition in which the RNA is present in solution in a liquid. The solution is preferably an aqueous solution. Thus, the liquid may be water, preferably sterile water, more preferably "water for injection" (WIF) or any other buffered or unbuffered aqueous solution. In one embodiment the liquid composition is an unbuffered solution, preferably a salt solution, more preferably a salt solution of a pharmaceutically acceptable salt, even more preferably an NaCl solution, i.e. saline. Preferably, the salt solution is isotonic and even more preferably it shows a physiological pH value (see below).

In another embodiment the solution in which the RNA is contained is a buffered solution. Preferably, such a solution is isotonic to blood and contains a buffer. In principle any buffer which effectively buffers in the physiological range, in particular in the range of pH 3.0 to 10.5 and more preferably pH 4.0 to 9.0, can be used. Preferable buffers are acetate, phosphate, carbonate, lactate and citrate buffers.

An example for an aqueous buffered solution is Ringer's solution. Ringer's solution is a solution of several salts dissolved in water for the purpose of creating an isotonic solution relative to the bodily fluids of a subject. It typically contains sodium chloride, potassium chloride, calcium chloride and sodium bicarbonate, wherein the latter one is included in order to balance the pH value. A standard Ringer's solution is prepared by dissolving 6.5 g NaCl, 0.42 g KCl, 0.25 g $CaCl_2$ and 1 mole of sodium bicarbonate in one liter of distilled water. Ringer's solution may optionally also contain ATP or dextrose as well as antibiotics or antifungals. In a preferred embodiment, the Ringer's solution is a lactated or acetated Ringer's solution. Lactated Ringer's solution is a solution that is isotonic with blood and normally intended for intravenous administration. One liter of lactated Ringer's solution contains 130 mEq of sodium ion (=130 mmol/L), 109 mEq of chloride ion (=109 mmol/L), 28 mEq of lactate (=28 mmol/L), 4 mEq of potassium ion (=4 mmol/L), 3 mEq of calcium ion (=1.5 mmol/L) and has an osmolarity of 273 mOsm/L. Acetated Ringer's solution generally contains calcium ions (c=0.9 mmol/l), potassium ions (c=5.4 mmol/l), magnesium ions (c=1.0 mmol/l), sodium ions (c=130 mmol/l), acetate ions (c=27 mmol/l) and chloride ions (c=112 mmol/l).

In a particularly preferred embodiment the liquid composition is a glucose solution containing the RNA. The concentration of the glucose is preferably in the range of 0.1-15% (m/v), more preferably in the range of 1-10% (m/v), even more preferably in the range of 2-8% (m/v) and particularly preferred in the range of 3.75-6.25% (m/v). It is especially preferred that the glucose concentration is in the range of 5% (m/v)±0.2% even more preferably in the range of 5% (m/v)±0.1%.

It is preferred that the glucose solution is a buffered solution. In principle any buffer can be used for buffering the glucose solution. The buffer is preferably a buffer which is able to maintain a pH value in the physiological range, i.e., in the range of pH 3.0 to 10.5, more preferably in the range of pH 4.0 to 9.0, even more preferably in the range of pH 5.0 to 8.0 and particularly preferred in the range of pH 7.3 to 7.5.

In a preferred embodiment the buffer classifies as a "Good's buffer". "Good's buffers" are buffers which have been described by Norman Good and colleagues during the period of 1966 to 1980 (Good et al., Biochemistry 5 (1966), 467-477; Good et al., Methods Enzymol. 24 (1972), 53-6; Ferguson et al., (Anal. Biochem. 104 (1980), 300-310)). Good's buffers are selected so as to fulfill the following criteria as far as this is possible:

$pK_a$: Because most biological reactions take place at near-neutral pH between 6 and 8, ideal buffers would have $pK_a$ values in this region to provide maximum buffering capacity there.

Solubility: For ease in handling and because biological systems are in aqueous systems, good solubility in water was required. Low solubility in nonpolar solvents (fats, oils, and organic solvents) is also considered beneficial, as this would tend to prevent the buffer compound from accumulating in nonpolar compartments in biological systems: cell membranes and other cell compartments.

Membrane impermeability: Ideally, a buffer will not readily pass through cell membranes, this will also reduce the accumulation of buffer compound within cells.

Minimal salt effects: Highly ionic buffers may cause problems or complications in some biological systems.

Influences on dissociation: There should be a minimum influence of buffer concentration, temperature, and ionic composition of the medium on the dissociation of the buffer.

Well-behaved cation interactions: If the buffers form complexes with cationic ligands, the complexes formed should remain soluble. Ideally, at least some of the buffering compounds will not form complexes.

Stability: The buffers should be chemically stable, resisting enzymatic and non-enzymatic degradation.
Biochemical inertness: The buffers should not influence or participate in any biochemical reactions.
Optical absorbance: Buffers should not absorb visible or ultraviolet light at wavelengths longer than 230 nm so as not to interfere with commonly used spectrophotometric assays.
Ease of preparation: Buffers should be easily prepared and purified from inexpensive materials.

Examples of Good's buffers, which are also preferably employed in the present invention are set forth in the following Table.

TABLE 1

| Buffer | $pK_a$ at 20° C. | $\Delta pK_a/°$ C. | Solubility in water at 0° C. |
|---|---|---|---|
| MES | 6.15 | −0.011 | 0.65M |
| ADA | 6.62 | −0.011 | — |
| PIPES | 6.82 | −0.0085 | — |
| ACES | 6.88 | −0.020 | 0.22M |
| MOPSO | 6.95 | −0.015 | 0.75M |
| Cholamine Chloride | 7.10 | −0.027 | 4.2M (As HCl) |
| MOPS | 7.15 | −0.013 | Large |
| BES | 7.17 | −0.016 | 3.2M |
| TES | 7.5 | −0.020 | 2.6M |
| HEPES | 7.55 | −0.014 | 2.25M |
| DIPSO | 7.6 | −0.015 | 0.24M |
| Acetaminoglycine | 7.7 | — | Very large |
| TAPSO | 7.7 | −0.018 | 1.0M |
| POPSO | 7.85 | −0.013 | — |
| HEPPSO | 7.9 | −0.01 | 2.2M |
| HEPPS | 8.1 | −0.015 | Large |
| Tricine | 8.15 | −0.021 | 0.8M |
| Glycinamide | 8.2 | −0.029 | 6.4M (As HCl) |
| Bicine | 8.35 | −0.018 | 1.1M |
| TAPS | 8.55 | −0.027 | Large |

MES: 2-(N-morpholino)ethanesulfonic acid
ADA: N-(2-Acetamido)iminodiacetic acid
PIPES: piperazine-N,N'-bis(2-ethanesulfonic acid
ACES: N-(2-Acetamido)-2-aminoethanesulfonic acid
MOPSO: 3-Morpholino-2-hydroxy-propanesulfonic acid
MOPS: 3-(N-morpholino)propanesulfonic acid
BES: N,N-bis[2-hydroxyethyl]-2-aminoethanesulfonic acid
TES: 2-[[1,3-dihydroxy-2-(hydroxymethyl)propan-2-yl]amino]ethanesulfonic acid
HEPES: 2-(4-(2-Hydroxyethyl)-1-piperazinyl)-ethansulfonsäure
DIPSO: 3-(N,N-Bis[2-hydroxyethyl]amino)-2-hydroxypropanesulfonic acid
TAPSO: 3-[[1,3-dihydroxy-2-(hydroxymethyl)propan-2-yl]amino]-2-hydroxypropane-1-sulfonic acid
POPSO: 2-hydroxy-3-[4-(2-hydroxy-3-sulfopropyl)piperazin-1-yl]propane-1-sulfonic acid
HEPPSO: N-(2-Hydroxyethyl)piperazine-N'-(2-hydroxypropanesulfonic acid)
HEPPS: 3-[4-(2-hydroxyethyl)piperazin-1-yl]propane-1-sulfonic acid
Tricine: N-(2-Hydroxy-1,1-bis(hydroxymethyl)ethyl)glycine
Bicine: 2-(Bis(2-hydroxyethyl)amino)acetic acid
TAPS: 3-[[1,3-dihydroxy-2-(hydroxymethyl)propan-2-yl]amino]propane-1-sulfonic acid The different above mentioned Good's buffers fulfill the selection criteria to various degrees and no buffer is completely inert in biological systems. Further examples for Good's buffers which have been identified in the meantime are AMPSO (N-(1,1-Dimethyl-2-hydroxyethyl)-3-amino-2-hydroxypropanesulfonic acid), CABS (4-(Cyclohexylamino)-1-butanesulfonic acid), CHES (N-Cyclohexyl-2-aminoethanesulfonic acid), CAPS (N-cyclohexyl-3-aminopropanesulfonic acid) and CAPSO (N-cyclohexyl-2-hydroxyl-3-aminopropanesulfonic acid).

In a particularly preferred embodiment the buffer is 2-(4-(2-Hydroxyethyl)-1-piperazinyl)-ethansulfonsaure (HEPES), i.e. the glucose solution is a HEPES buffered glucose solution (also referred to herein as HBG). As shown in the appended Examples, an efficient expression of mRNA in tendon tissue can be achieved if mRNA, for example encoding (human) BMP-7 or a reporter protein (luciferase), is injected into ligament or tendon tissue in the form of an aqueous solution, e.g. in saline solution or in different buffered solutions such as acetated or lactated Ringer's solution. A particularly high expression can be achieved if the mRNA is administered in HEPES buffered glucose (HBG), pH 7.4.

More preferably the HBG is a HBG with a concentration in the range of 0.75×HBG to 1.25×HBG, more preferably, 0.8×HBG to 1.2×HBG, even more preferably, 0.9×HBG to 1.1×HBG, and particularly preferred 1×HBG with 1×HBG being. The term "1×HBG" refers to a solution with the following composition: 25 mM HEPES; 5% glucose m/v.

In one embodiment, the liquid composition of the invention does not contain (an) amino acid(s) and/or ammonium.

The concentration of the RNA in the liquid composition is not particularly crucial and can be adjusted as required. Preferably, the concentration lies in the range of 0.1 to 5.0 µg/µl, or in the range of 0.25 to 2.5 µg/µl, more preferably in the range of 0.5 to 2.0 µg/µl, more preferably in the range of 0.75 to 1.5 µg/µl, even more preferably in the range of 0.80 to 1.20 µg/µl, particularly preferred in the range of 0.90 to 1.10 µg/µl.

The liquid composition containing the RNA can be applied to the ligament or tendon tissue by means known to the person skilled in the art, preferably by injection (direct/local injection), typically by using a syringe with a needle. In principle any commercially available syringe in combination with a needle can be used for this purpose. Preferred are hypodermic needles. As is evident from the appended Examples, the size of the needle, in particular the diameter of the needle, used for injecting the liquid composition containing the RNA may have an influence on the effectiveness of the expression/activity of the RNA in the ligament or tendon tissue. The diameter of a needle is indicated by the needle gauge (G; according to the Stub's Needle Gauge). Typically needles in medical use range from 7 G (the largest) to 33 G (the smallest). In a preferred embodiment, the needle used for injecting the liquid composition containing the RNA has a diameter in the range of 20 G to 27 G, preferably in the range of 21 G to 26 G, more preferably in the range of 22 G to 25 G, even more preferably 23 G or 24 G. Particularly preferred are needles with a diameter of 23 G.

The RNA contained in the liquid composition can be any RNA. Thus, in principle any type of RNA can be employed in the context of the present invention. In one preferred embodiment the RNA is a single-stranded RNA. The term "single-stranded RNA" means a single consecutive chain of ribonucleotides in contrast to RNA molecules in which two or more separate chains form a double-stranded molecule due to hybridization of the separate chains. The term "single-stranded RNA" does not exclude that the single-stranded molecule forms in itself double-stranded structures such as loops, secondary or tertiary structures.

The term "RNA" covers RNA which codes for an amino acid sequence as well as RNA which does not code for an amino acid sequence. It has been suggested that more than 80% of the genome contains functional DNA elements that do not code for proteins. These noncoding sequences include regulatory DNA elements (binding sites for transcription factors, regulators and coregulators etc.) and sequences that code for transcripts that are never translated into proteins. These transcripts, which are encoded by the genome and transcribed into RNA but do not get translated into proteins, are called noncoding RNAs (ncRNAs). Thus, in one embodiment the RNA is a noncoding RNA. Preferably, the noncoding RNA is a single-stranded molecule. Studies demonstrate that ncRNAs are critical players in gene regulation, maintenance of genomic integrity, cell differentiation, and development, and they are misregulated in various human diseases. There are different types of ncRNAs: short (20-50 nt), medium (50-200 nt), and long (>200 nt) ncRNAs. Short ncRNA includes microRNA (miRNA), small interfering RNA (siRNA), piwi-interacting RNA (piRNA), and transcription initiating RNA (tiRNA). Examples of medium ncRNAs are small nuclear RNAs (snRNAs), small nucleolar RNAs (snoRNAs), transfer RNAs (tRNAs), transcription start-site-associated RNAs (TSSaRNAs), promoter-associated small RNAs (PASRs), and promoter upstream transcripts (PROMPTs). Long noncoding RNAs (lncRNA) include long-intergenic noncoding RNA (lincRNA), anti-sense-lncRNA, intronic lncRNA, transcribed ultra-conserved RNAs (T-UCRs), and others (Bhan A, Mandal S S, Chem Med Chem. 2014 Mar. 26. doi: 10.1002/cmdc.201300534). Of the above-mentioned non-coding RNAs only siRNA is double-stranded. Thus, since in a preferred embodiment the noncoding RNA is single-stranded, it is preferred that the noncoding RNA is not siRNA. In another (particularly preferred) embodiment the RNA is a coding RNA, i.e. an RNA which codes for an amino acid sequence. Such RNA molecules are also referred to as mRNA (messenger RNA) and are single-stranded RNA molecules. The RNA may be made by synthetic chemical and enzymatic methodology known to one of ordinary skill in the art, or by the use of recombinant technology, or may be isolated from natural sources, or by a combination thereof. The RNA may optionally comprise unnatural nucleotides.

Preferably, the RNA refers to mRNA and most preferably to modified mRNA, in particular to modified mRNA as described herein below and, for example, in WO 2011/012316. In a (particularly) preferred embodiment the mRNA encodes a polypeptide which can have a positive effect on the healing process of ligament or tendon lesions. Thus, the polypeptide is a polypeptide which has a beneficial effect on the healing process of ligament or tendon lesions, in particular a polypeptide which is therapeutically active in the healing process of ligament or tendon. Examples for such polypeptides are growth factors and cytokines. Examples for growth factors are platelet-derived growth factor (PDGF), FGF (fibroblast growth factor) such as basic fibroblast growth factor (bFGF), insulin-like growth factor 1 (IGF-1), transforming growth factor β1 (TGF-β1), epidermal growth factor (EGF). Without being bound by theory, both, FGF and TGF-β (TGF-β1) are important/involved in the parallel organization of collagen fibrils. Other Examples are growth and differentiation factors (GDFs) which are a subfamily of the bone morphogenic proteins (BMPs) and are involved in the embryonic development of different organs. GDF 5, 6 (BMP-13) and 7 (BMP-12) are particularly preferred since they have been shown to lead to the ectopic formation of ligaments and tendons when injected into rats (Evans, C H, Sports Med. 28 (1999), 71-76). A further and preferred example for a growth factor is BMP-7, for example as encoded by a nucleotide sequence as depicted in SEQ ID NO. 1, 2 or 3 (see also, for example, Pubmed accession number: NM_001719; Version: NM_001719.2, GI:187608319; http://www.ncbi.nlm.nih.gov/nuccore/NM_001719.2 (non-codon-optimized sequence including exons; the coding sequence starts at nt948 and ends, without interruptions, at nt4031)).

Other examples for proteins which can be encoded by the mRNA are transcription factors to activate the regeneration program in tendons/ligaments or inhibit anti-regenerative cellular programs in tendons/ligaments, e.g. EGR1/2, Scleraxis, Mohawk and Sox9 (Guerquin et al., J. Clin. Invest. 123 (2013), 3564-3576; Huanhuan Liu et al., Cell and Tissue Research 356(2014), 287-298). Further examples for proteins to be encoded by the mRNA are structural proteins such as collagens or proteoglycans.

Further examples for proteins which can be encoded by the mRNA are the following: FBJ osteosarcoma oncogene B (Fosb), FBJ osteosarcoma oncogene (c-Fos), Regulator of G protein signaling-1 (Rgs1), Galanin-like peptide (Galp), Early growth response protein-1 (Egr1), Early growth response protein-2 (Egr2), NK6 homeobox 1 (Nkx), Similar to ribosomal protein s10 (LOC688706), Similar to testis-specific farnecyl pyrophosphate synthetase (RGD1565157), Frizzled homolog 9 (Fzd9), Aldehyde oxidase-1 (Aox-1), Selenium binding protein 1 (Selenbp1), Mitogen-activated protein kinase kinase kinase 13 (Map3k13), Aggrecan, Adamts-4, Alox-5, Ptges, iNOS, IL-1, IL-1 receptor antagonist, Angpoietin 1, Angpoietin like 1, Vegf, Pappa, Fmo2, C1qTNF3, Fabp4, Scleraxis, Tendomodulin, F2rl2, F3, and F5, tgf-3, mdk, and bmp-6, keratocan, and fibromodulin, coil VIII, coil XI, coil I, Amot, Epha3, Epha4, Fgf-2, Calp6, Enpp2, Fmo1-4, MaoB, Nox4, Xdh, Hmox1, S100a9, Pappa, Arklc14, Arklc19, Gstt2, Gstm5, Gstm7, Hasph1, Hsph8, Hspa1b, Six1, Six2, growth and differentiation factors (GDFs, GDF1-11, GDF15), Smad8, Homer-1b, Metabotropic glutamate receptor type 1, Histamine H2-receptor, Vegetal related, Secreted NK cell receptor 2B4, 5-lipoxygenase, Preproepidermal growth factor, Immunoglobulin lambda-5 chain, Lumican, Betacellulin, rSec8, Sonic hedgehog, LIM homeobox protein 7, Frizzled, ZOG, Notch 3 protein, Tissue inhibitor of metalloproteinase type 2, N-methyl-D-aspartate receptor subunit 2C, T-cell marker CD2 antigen, Glutamate receptor interacting protein 2, Synapsin 2b, Hepatocyte growth factor, T-cell receptor active beta-chain V-region, Growth factor receptor-bound protein 14, Fibroblast growth factor receptor-3, Vegetal related, High-affinity glutamate transporter and Homeobox protein rPtx2. The genes encoding these proteins have been reported to be dysregulated during regeneration of tendon tissue.

In one embodiment, the administration of two or more (e.g. 3, 4 or 5) mRNAs each encoding a different polypeptide as described herein and, in particular, as described above is envisaged. In this context, administration may be simultaneously (preferred) or sequentially. Likewise, the administration of an mRNA which encodes two or more (e.g. 3, 4 or 5) of the polypeptides as described herein and, in particular, as described above may be applied.

In the context of this embodiment, it is preferred that the two or more (e.g. 3, 4 or 5) polypeptides are selected from the group consisting of PDGF, FGF such as bFGF, IGF-1, TGF-1, EGF, a GDF, Egr1, Egr2, SCX and BMP. In this context, the GDF may be GDF 5, 6 (BMP-13), 7 (BMP-12) and/or myostatin (GDF-8) and/or the BMP may be BMP-7.

The term "mRNA" (i.e. messenger RNA) refers to polymers which are built up of nucleoside phosphate building blocks mainly with adenosine, cytidine, uridine and guanosine as nucleosides, and which contain a coding region encoding a polypeptide. In the context of the present invention, mRNA should be understood to mean any polyribonucleotide molecule which, if it comes into the cell, is suitable for the expression of a polypeptide or fragment thereof or is translatable to a polypeptide or fragment thereof. The term "polypeptide" here encompasses any kind of amino acid sequence, i.e. chains of two or more amino acids which are each linked via peptide bonds and also includes peptides and fusion proteins.

The mRNA contains a ribonucleotide sequence which encodes a polypeptide or fragment thereof whose function in the cell or in the vicinity of the cell is needed or beneficial, in particular in the context of the healing of ligament or tendon lesions.

The mRNA may contain the sequence for the complete polypeptide or a functional variant thereof. Further, the ribonucleotide sequence can encode a polypeptide which acts as a factor, inducer, regulator, stimulator or enzyme, or a functional fragment thereof, where this polypeptide is one whose function is necessary in order to remedy a disorder, in particular a ligament or tendon lesion.

Here, functional variant is understood to mean a fragment which in the cell can undertake the function of the polypeptide whose function in the cell is needed. In addition, the mRNA may also have further functional regions and/or 3' or 5' noncoding regions. The 3' and/or 5' noncoding regions can be the regions naturally flanking the polypeptide-encoding sequence or artificial sequences which contribute to the stabilization of the RNA. Those skilled in the art can determine the sequences suitable for this in each case by routine experiments.

In a preferred embodiment, the mRNA contains an m7GpppG cap, an internal ribosome entry site (IRES) and/or a polyA tail at the 3' end in particular in order to improve translation. The mRNA can have further regions promoting translation.

In a preferred embodiment the RNA, preferably the mRNA, is an RNA which contains a combination of modified and unmodified nucleotides. Preferably, it is an (m)RNA containing a combination of modified and unmodified nucleotides as described in WO2011/012316. The mRNA described therein is reported to show an increased stability and diminished immunogenicity. In a preferred embodiment, in such a modified mRNA 5 to 50% of the cytidine nucleotides and 5 to 50% of the uridine nucleotides are modified. The adenosine- and guanosine-containing nucleotides can be unmodified. The adenosine and guanosine nucleotides can be unmodified or partially modified, and they are preferably present in unmodified form. Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties. It is particularly preferred that the modified cytidine nucleotides are 5-methylcytidin residues and the modified uridine nucleotides are 2-thiouridin residues. Most preferably, the content of modified cytidine nucleotides and the content of the modified uridine nucleotides is 25%, respectively.

In another preferred embodiment, the RNA, preferably the mRNA, may be combined with target binding sites, targeting sequences and/or with micro-RNA binding sites, in order to allow activity of the desired RNA only in the relevant cells. In a further preferred embodiment, the RNA can be combined with micro-RNAs or shRNAs downstream of the 3' polyA tail.

Preferably, the naked RNA to be employed in the context of the present invention, in particular the naked mRNA, is codon-optimized. A non-limiting example of a codon-optimized and chemically modified (m)RNA to be employed in the context of the invention is the codon-optimized BMP-7-encoding mRNA as depicted in SEQ ID NO. 2 or 3. The skilled person is readily in the position to codon-optimize a given (m)RNA by relying on respective means and methods known in the art. For example, codon optimization may be performed by using Eurofins "GENEius" software (see, for example, https://www.eurofinsqenomics.eu/media/892634/an_geneius_compared-to-competitors.pdf). Moreover, the skilled person is readily in the position to chemically modify a given (m)RNA by relying on respective means and methods known in the art (see, for example, WO 2011/012316).

The present invention also relates to RNA, preferably mRNA encoding a polypeptide, for use in the treatment of ligament or tendon lesions wherein the RNA is administered to, in particular directly into, the ligament or tendon (preferably by injection) in the form of a liquid composition wherein the RNA is contained as naked RNA. As regards the way of administration and the characteristics of the composition and the RNA contained therein, the same applies as has been set forth herein elsewhere.

The present invention also relates to a method for treating (or preventing) ligament or tendon lesions comprising the administration (of a pharmaceutically effective amount) of a liquid composition containing naked RNA, preferably mRNA encoding a polypeptide (e.g. BMP-7), which is beneficial in the process of healing the ligament or tendon lesion to the ligament or tendon (to a patient in need thereof). As regards the way of administration and the characteristics of the composition and the RNA contained therein, the same applies as has been set forth herein elsewhere.

In a preferred embodiment, the liquid composition and naked RNA, respectively, of the present invention is to be administered to, in particular directly into, the ligament or tendon. In this context, the most preferred way of administration is injection, i.e. intra-ligament or intra-tendon injection.

It is, in principle, envisaged in the context of the invention to administer the liquid composition and naked RNA, respectively, as early as possible, i.e. at the earliest possible stage of the ligament/tendon lesion and (degenerative) ligamentopathy/tendinopathy, respectively. For example, this stage is once (a) first symptom(s) have/has been observed (e.g. pain or tenderness) or once a surgical intervention starts or during a surgical intervention. This applies to both, the acute and chronic forms of the lesions/diseases/disorders to be treated or prevented in accordance with the invention. However, any possible point of time after the diagnosis is possible and worthwhile and, hence, envisaged in accordance with the invention. For example, in case there is a surgical intervention (for example following a ligament/tendon rupture) the liquid composition and naked RNA, respectively, may be administered already during, but at least shortly after, the surgical intervention. When administered during surgical intervention, the liquid composition and naked RNA, respectively, may be administered to (for example by injection into) one of or both tails of the rupture.

In a specific embodiment, the liquid composition and naked RNA, respectively, is to be administered during or even before the inflammatory and early proliferative phase, respectively, of ligament/tendon regeneration. For example, administration may be during day 0 to day 10, preferably during day 0 to day 7, post injury/post lesion. More specifically, administration may be at day 0, 1, 2, 3, 4, 5, 6 or 7 post injury/post lesion. Preferably, administration is at day 1 and even more preferably at day 0 post injury/post lesion.

The administration of the liquid composition and naked RNA, respectively, in accordance with the invention may, for example depending on the course of the lesion/disease/disorder to be treated/prevented, be repeated at least once but preferably several times (for example 3 to 5 times). The repeated administration may be every few weeks (for example every 1, 2, 3, or 4 weeks) up to every few days (for example every 1, 2, 3, 4, 5 or 6 days).

The liquid composition and naked RNA, respectively, of the invention can be administered to a patient at a suitable dose. The dosage regimen can be determined by the attending physician, for example based on clinical factors. As is well known in the medical arts, dosages for any one patient depend upon many factors, including the patient's size, body surface area, age, the particular compound to be administered, sex, time and route of administration, general health, and other drugs being administered concurrently. However, the skilled person/the attending physician is readily in a position to (a) deduce (therapeutically) effective concentration(s) and/or dosages of the active substance(s) to be administered, e. g. in vivo or ex vivo. Corresponding samples may be taken from, for example, the ligament or tendon (e.g. by a suitable probe) and the active compounds (naked RNA) may be detected and their corresponding concentrations may be determined in said samples, for example by HPLC.

The determination of the active compound concentrations may be obtained in human patients, healthy (human) individuals as well as in animals (e.g. mice, rats, pigs, horses and the like), like laboratory animals, non-human transgenic animals (e.g. transgenic mice, rats, pigs, and the like). It is envisaged that the determination of active compound concentrations in, e. g. the ligament or tendon, may, for example, be deduced in (healthy) volunteers and corresponding administration schemes for (human) patients may be established. For example, the dosage dependencies (e.g. dosage administered versus concentration-/dosage detected (in various regions of) the ligament or tendon may be determined by standard methods known in the art. Further methods comprise, but are not limited to, the detection of labelled peptides in vivo (e.g. by corresponding labelling techniques, like radioactive labelling, fluorescent labelling, etc.) or physiological/biochemical assays. Accordingly, the dosage of active compounds to be administered in order to obtain a desired concentration of the active compounds (in a certain part of the ligament/tendon) may be deduced. These and other methods to deduce such concentrations are known in the art.

A typical dose of active substances (e.g. naked RNA) can be, for example, in the range of 1 ng to several grams, preferably in the range of 0.1 μg to 1 g, preferably in the range of 1 μg to 0.1 g, preferably in the range of 10 μg to 10 mg, and most preferably in the range of 100 μg to 1 mg. This particularly applies to a human patient. Applied to (m)RNA therapy, the dosage of an (m)RNA for expression (or for inhibition of expression) should correspond to this range; however, doses below or above this exemplary range are, in principle, also envisioned, especially considering the aforementioned factors. Generally, the regimen as a regular administration of the liquid composition should be in the range of 0.1 μg to 10 mg units, preferably in the range of 1 μg to 1 mg units, more preferably in the range of 10 μg to 0.1 mg units per kilogram of body weight per day. Again, this is particularly applies to a human patient. Progress can be monitored by periodic assessment. Dosages may vary but a preferred dosage for administration by injection of (m)RNAs as constituents of the liquid composition of the present invention is from approximately $10^5$ to $10^{15}$ copies of the (m)RNA molecule per injection. Again, this particularly applies to a human patient.

In particular, the liquid composition of the invention is envisaged to be administered to a patient, preferably to a human patient/a human. However, the herein described ligament or tendon lesions (and related conditions) may also be treated (or prevented) in a non-human animal subject/patient like, for example, a pet (e.g. dog, cat, rabbit, rat and mouse), a cattle (e.g. cow, pig, sheep), a horse (e.g. a race horse) or pony or a bird (e.g. chicken, turkey, parrot).

Any of the liquid compositions of the invention may be provided together with an instruction manual or instruction leaflet. The instruction manual/leaflet may comprise guidance for the skilled person/attending physician how to treat (or prevent) a disease or disorder as described herein (ligament or tendon lesion) in accordance with the invention. In particular, the instruction manual/leaflet may comprise guidance as to the herein described mode of delivery/administration and delivery/administration regimen, respectively (for example route of delivery/administration, dosage regimen, time of delivery/administration, frequency of delivery/administration). In particular, the instruction manual/leaflet may comprise the instruction that the liquid composition and naked RNA, respectively, is to be injected and/or is prepared for injection into the ligament or tendon. The instruction manual/leaflet may further comprise the instruction that the liquid composition and naked RNA, respectively, is prepared for administration during the inflammatory phase which follows the ligament or tendon lesion. In principle, what has been said herein elsewhere with respect to the mode of delivery/administration and delivery/administration regimen, respectively, may be comprised as respective instructions in the instruction manual/leaflet.

The present invention also relates to a HEPES-buffered glucose solution comprising naked RNA, preferably an mRNA encoding a polypeptide (e.g. BMP-7). As regards the preferred embodiments of the solution and the RNA, the same applies as has been set forth herein elsewhere.

Furthermore, the present invention also relates to a therapeutic composition containing RNA, preferably mRNA encoding a polypeptide (e.g. BMP-7), which is therapeutically active in the healing process of ligament or tendon. Preferably, the therapeutic composition is a liquid formulation in which the RNA is present in the form of naked RNA. As regards the way of administration and the characteristics of the composition and the RNA contained therein, the same applies as has been set forth herein elsewhere.

The liquid composition of the invention may be provided in (or in form of) a kit/a kit of contents. The kit may comprise one or more of the components of the liquid composition of the invention, for example in one or more separate containers. For example, the kit may comprise the naked RNA (e.g. in dried form), a solubilizer and (buffered or unbuffered) aqueous solution, for example in one, two or three (or more) separate containers, respectively. The kit may also comprise the instruction manual or instruction leaflet.

FIGURE LEGENDS

The patent or application file contains at least one drawing executed in color. Copies of this patent or patent application publication with color drawings will be provided by the Office upon request and payment of the necessary fee.

Figure 10A:
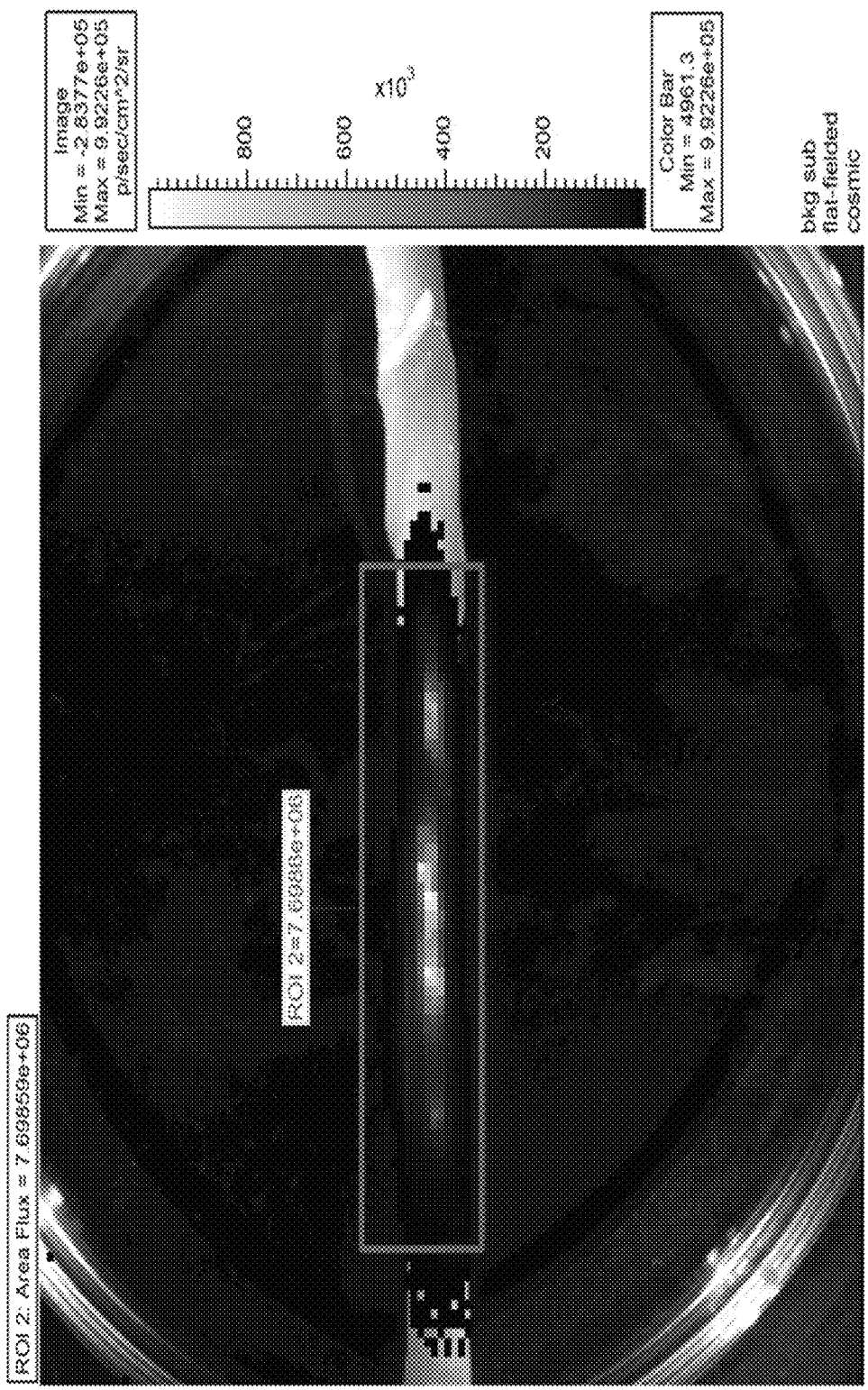
FIG. 10a shows intact ovine deep digital flexor tendon. High expression in the injected area of the tendon 24 hours after SNIM®-FFL-RNA (WO 2011/012316) injection (see Example 10).
Figure 10B:
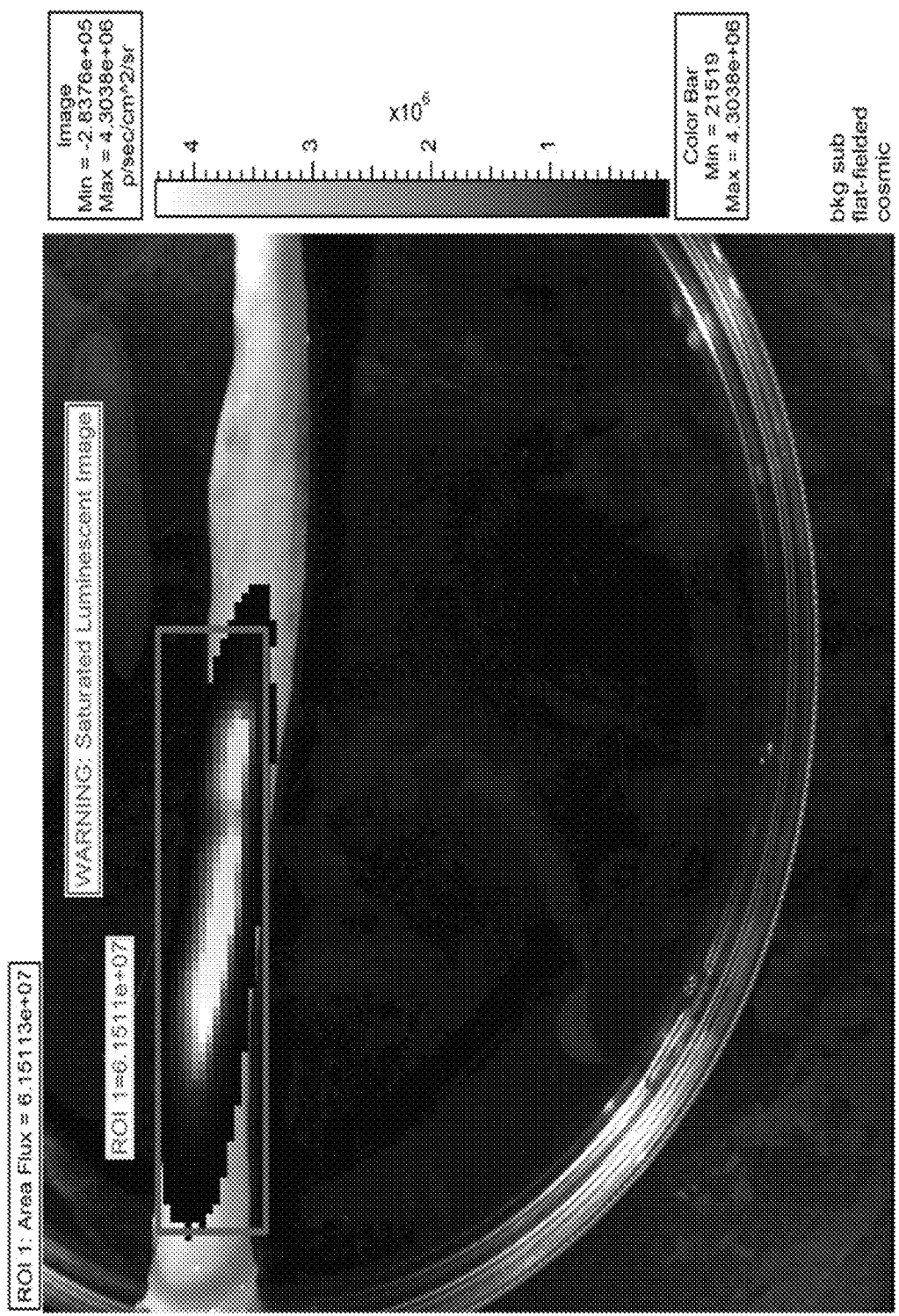
FIG. 10b shows mild damaged tendon by injection of 100 CDU. High expression in the injected peripheral area of the defect (see Example 10).
Figure 10C:
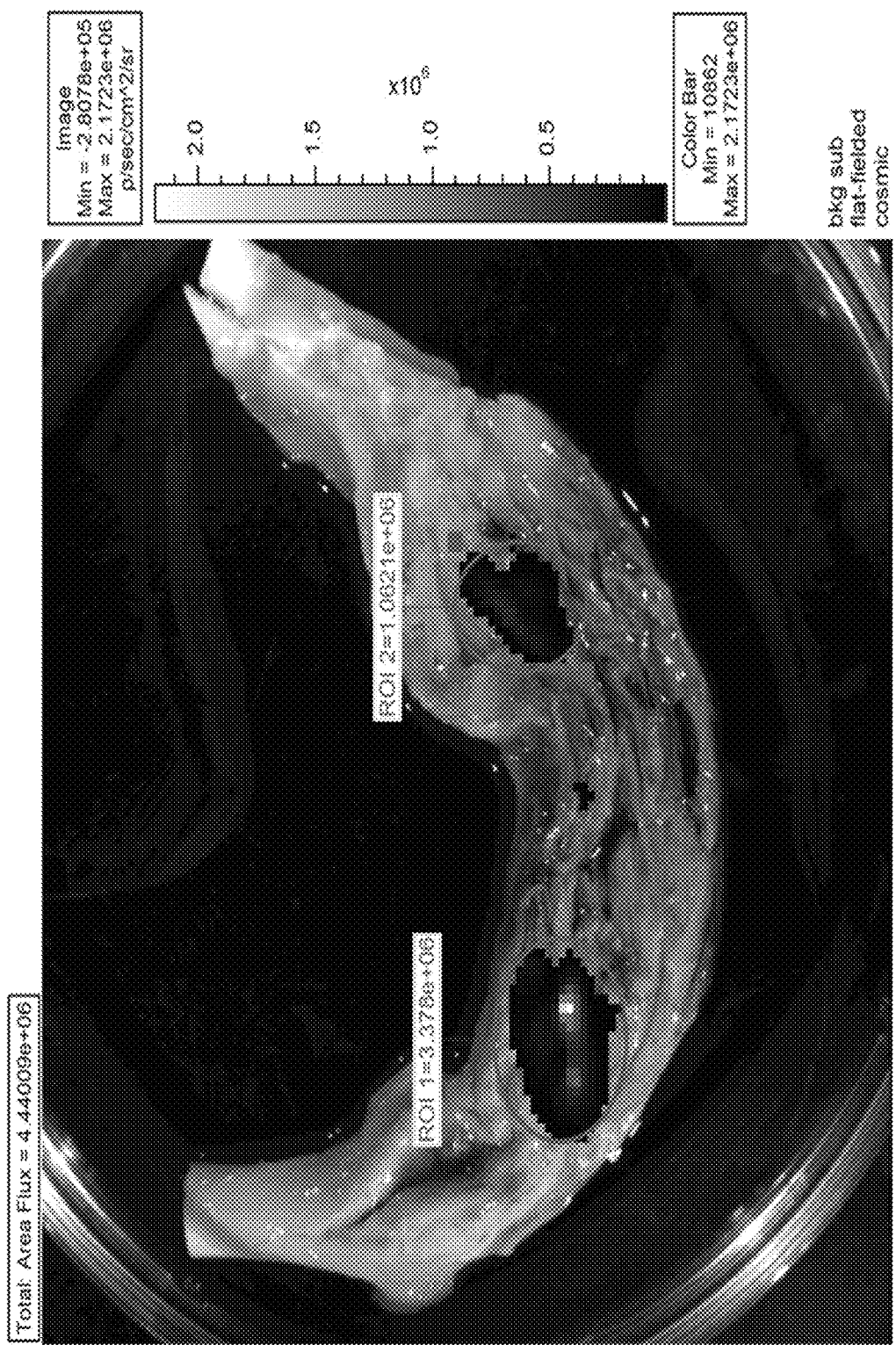

FIG. 10c shows moderate damaged tendon by injection of 200 CDU. Punctual expression in the peripheral area of the defect. Tendon was opened longitudinally prior to the incubation in luciferin (see Example 10).

Figure 10D:
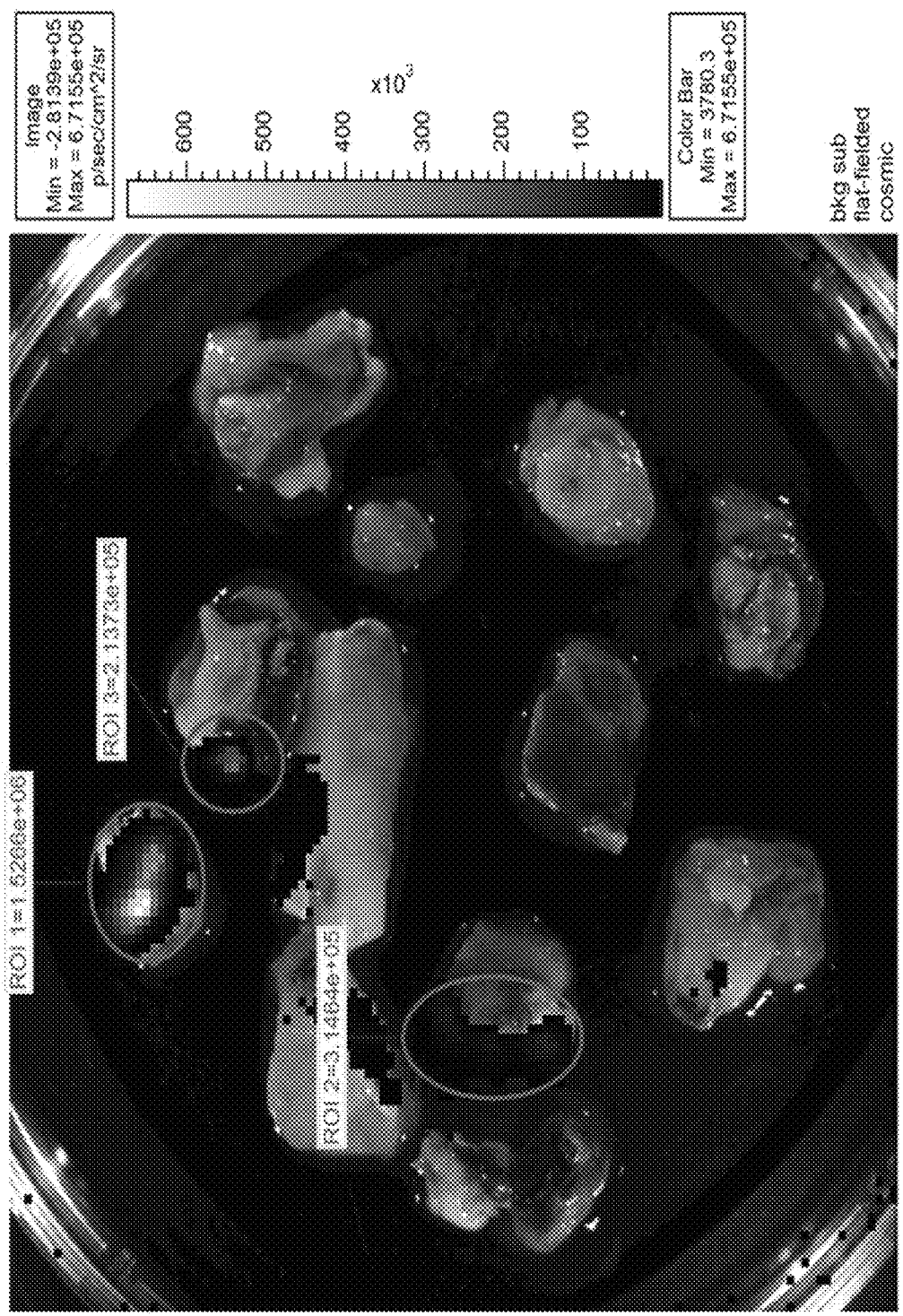

FIG. 10d shows severe damaged tendon by injection of 500 CDU. Punctual expression in the peripheral area of the defect. Tendon was cut before incubation in luciferin solution (see Example 10).

FIG. 11A Longitudinal section of ovine tendons 24 hours post modified LacZ mRNA injection and LacZ staining. Blue precipitate is detectable in the central area of the tendon (see Example 11).

FIG. 11B Longitudinal section of untreated control ovine tendons and LacZ staining. Blue precipitate is not detectable in the central area of the tendon (see Example 11).

FIG. 11C Microscopic images of a longitudinal section of ovine tendons 24 hours post modified LacZ mRNA injection and LacZ staining. Blue precipitate is detectable in cells between tendon fibers (see Example 11).

FIG. 11D Microscopic images of a longitudinal section of untreated control ovine tendons and LacZ staining. Blue precipitate is not detectable in cells between tendon fibers (see Example 11).

FIG. 12A Microscopic images of a longitudinal section of BMP7-immunohistochemistry of modified BMP7 mRNA treated rat Achilles tendon 24 hrs after injection. Red/purple staining is detectable in cells between tendon fibers (see Example 12).

FIG. 12B Microscopic images of a longitudinal section of a control untreated rat Achilles tendon. Red/purple staining is not detectable in cells between tendon fibers (see Example 12).

Figure 13:
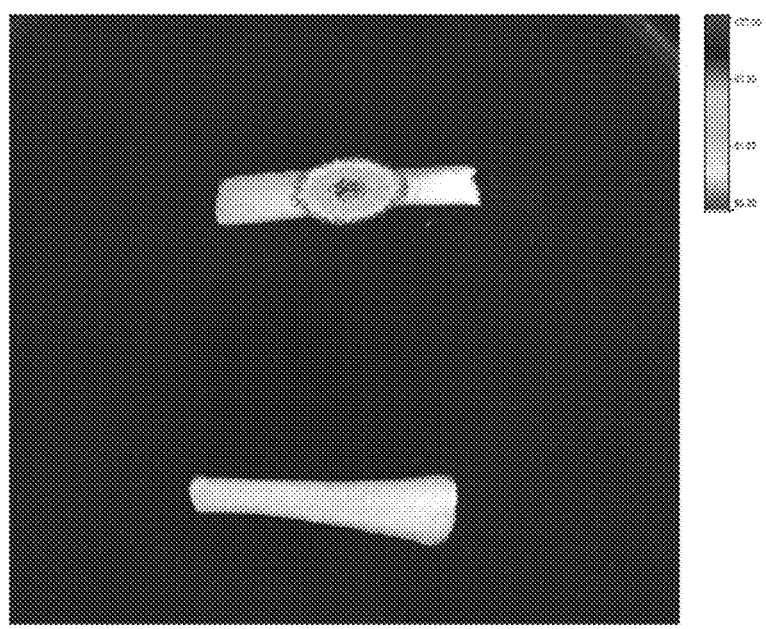

FIG. 13 $I^{125}$ marked mRNA was injected into porcine tendon and radioisotopically imaged 30 min later (upper tendon). Lower tendon act as negative control. (see Example 13). mRNA slowly diffuses away from the site of injection.

Figure 14:
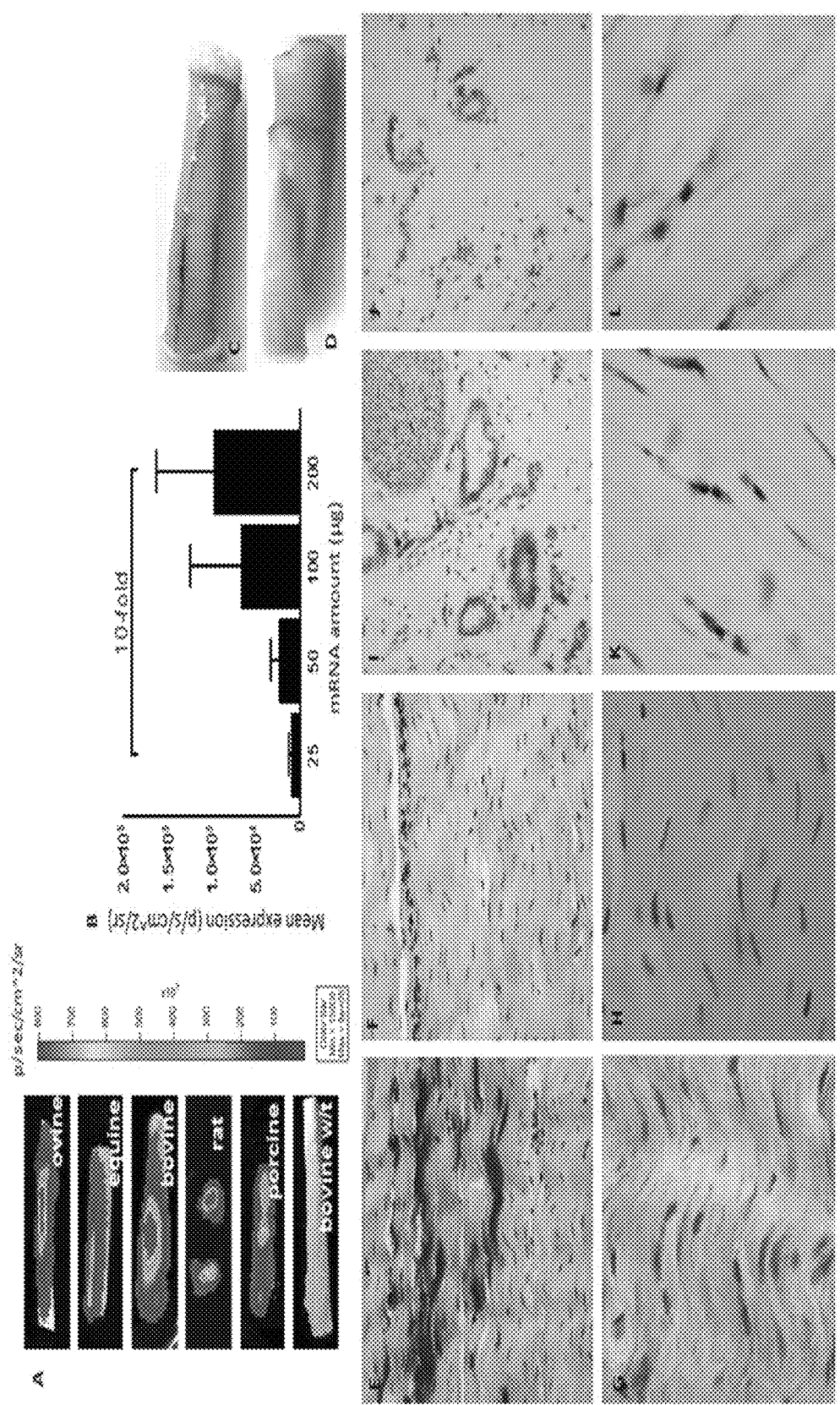

FIG. 14 Protein expression in intact tendon explants after naked mRNA injection. (A) Bioluminescence imaging (BLI) 24 hours after cmRNA$^{LUC}$ injection in tendon explants of different species. Either 26.6 µg [0.65 mg/ml] (rat), 50 µg [0.5 mg/ml] (bovine, equine) or 100 µg [1 mg/ml] (porcine, ovine) of naked cmRNA$^{LUC}$ was injected. Expression was detected in all species tested. (B) Luciferase expression is dose-dependent. Porcine tendon explants were injected with either 25 µg, 50 µg, 100 µg or 200 µg of cmRNA$^{LUC}$ in 250 µl of isotonic saline solution (NaCl). Mean expression±SEM of 24 hour point of time is shown (n=4). (C) Porcine tendon explants showing macroscopically blue precipitate spread in a tube-like manner 24 hours after cmRNA$^{LacZ}$ injection and X-Gal staining. (D) Control explants 24 hours after cmRNA$^{LUC}$ injection and X-Gal staining. (E, F, G, H) Sections of LacZ stained cmRNA$^{LacZ}$ injected (E, G) and cmRNA$^{LUC}$ injected porcine tendons (F, H) counterstained with hematoxylin. β-galactosidase was locally expressed near the injection site (E) and could be detected in tenocytes (G) and connective tissue, while cmRNA$^{LUC}$ treated controls were negative for β-gal activity (F, H). E, F Original magnification ×20. G, H Original magnification ×40. (I, J, K, L) Immunostaining of BMP-7 in sections of cmRNA$^{BMP-7}$ treated rat Achilles tendons (I, K) and untreated controls (J, L) counterstained with hematoxylin. Positive signals were stained red. BMP-7 is increasingly detectable in vascular walls, connective tissue (I) as well as in tenocytes (K) in cmRNA$^{BMP-7}$ treated tendons. I, J Original magnification ×10. K, L Original magnification ×40.

Figure 15:
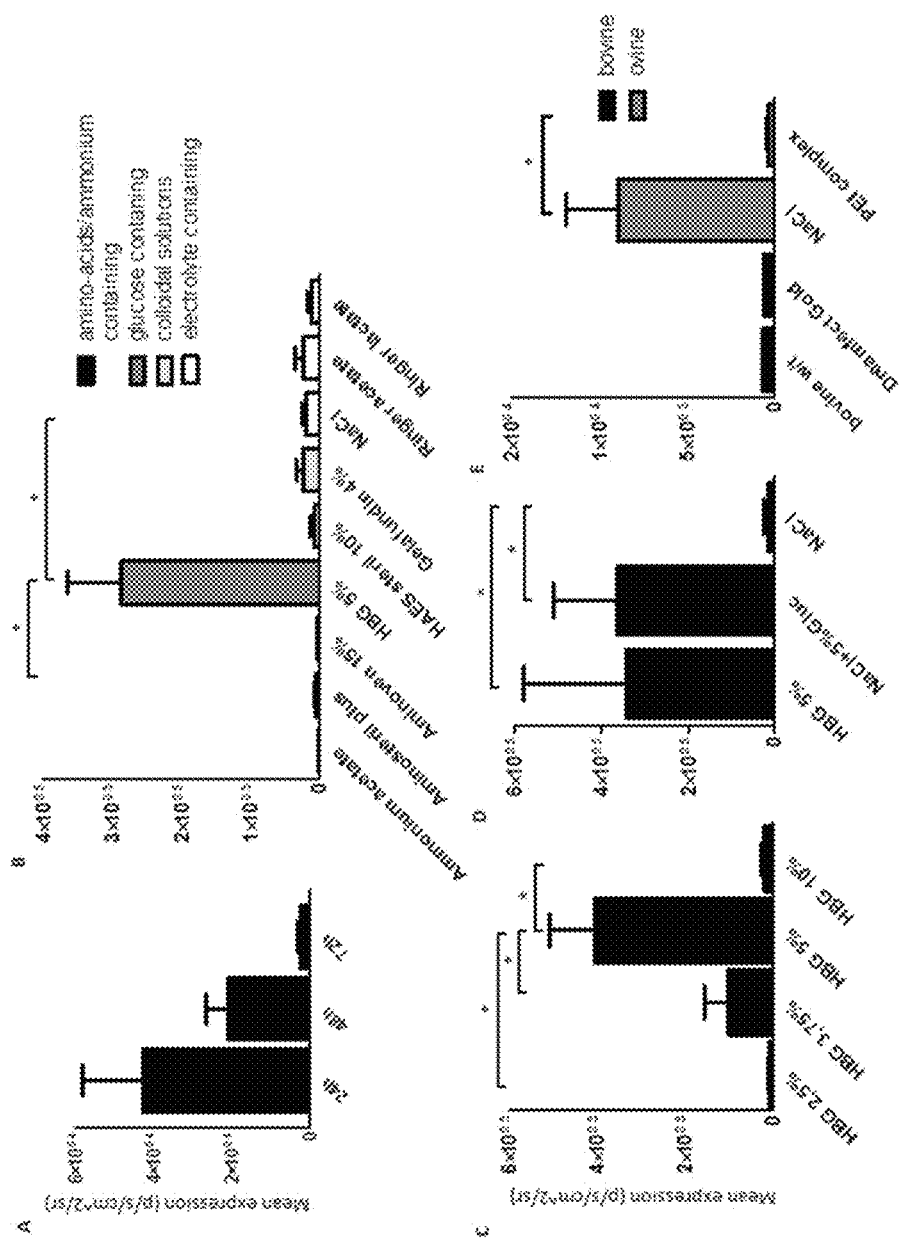

FIG. 15 Expression kinetics and comparison of different solvents used for naked mRNA injection. (A) Kinetics of luciferase expression in bovine tendon explants. 50 µg cmRNA$^{LUC}$ [0.5 mg/ml] in isotonic saline solution was injected. Data represents mean expression levels±SEM after 24 h, 48 h and 72 h post injection (n≥10). Highest luciferase expression was measured after 24 hours post injection. Within 72 hours luciferase activity decreased to background levels. (B) 50 µg cmRNA$^{LUC}$ [0.25 mg/ml] in different solvents were injected in bovine tendon explants (n≥5). Vertical axis shows FFL expression values, while horizontal axis shows different solvents that where used for dilution. Data represents average expression levels±SEM 24 hours post injection. Significantly enhanced expression was observed with HBG 5% (15-fold) compared to cmRNA$^{LUC}$ dissolved in saline solution (*, p<0.05) and (57-fold) compared to Aminosteril plus (*, p<0.05). (C) Comparison of different HBG concentrations. Data represent mean±SEM of Luciferase expression after 24 hours post cmRNA$^{LUC}$ (0.5 mg/ml) injection (n≥5). HBG 5% resulted in significant higher expression values (50-fold) compared to 2.5%, 20-fold compared to 10% (*, p<0.05) and 4-fold compared to 3.75% (*, p<0.05). (D) Comparison of glucose-containing solvents and solutions without glucose. 50 µg cmRNA$^{LUC}$ [0.5 mg/ml] was injected in porcine tendon explants 24 hours prior to BLI (n=5). Data represents mean±SEM of Luciferase expression. Average Luciferase expression values from cmRNA$^{LUC}$ formulated in HBG 5% and in NaCl+ 5% Gluc were significantly higher (20-fold for HBG 5% and 21-fold for NaCl+5% Gluc) compared to isotonic saline solution (*, p<0.05). (E) Comparison of carrier systems and isotonic saline. Average luciferase activity with cmRNA$^{LUC}$ complexed either with lipid or polymer carriers only reached levels of background expression in bovine as well as ovine tendons. Average expression from 25 µg cmRNA$^{LUC}$ dissolved in saline solution were 22-fold higher compared to 25 μg cmRNA$^{LUC}$ complexed with brPEI (*, p<0.05).

Figure 16:
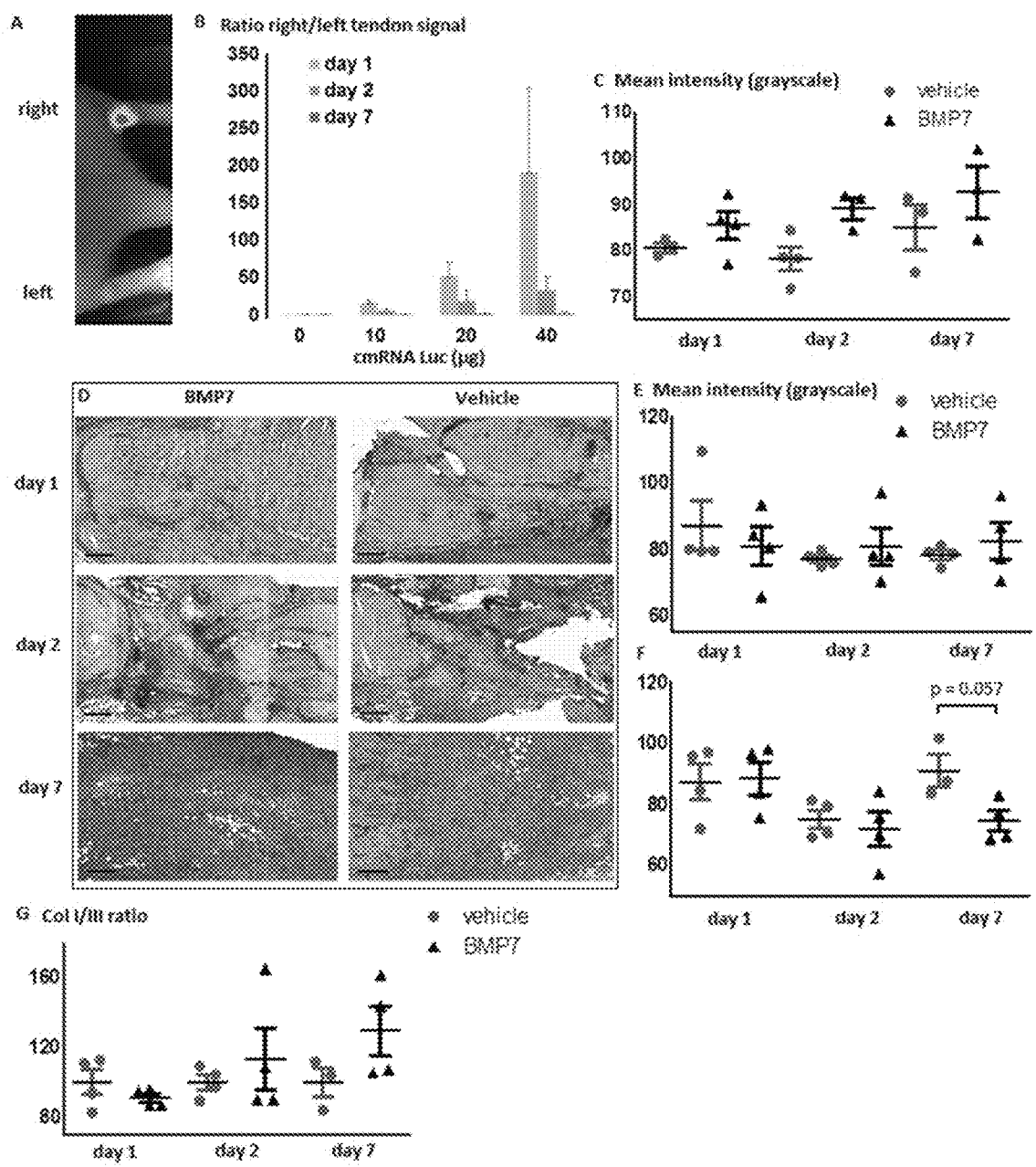

FIG. 16 Protein expression in intact and injured rat Achilles tendons in vivo. (A) BLI 24 hours after cmRNA$^{Luc}$ injection into the intact Achilles tendon. (B) Kinetics and dose-dependency of Luciferase expression in intact Achilles tendons. Luciferin substrate was applied intraperitoneally 15 minutes prior to the measurement (mean±SEM, n=4) (C) Mean intensity of BMP-7 immunostaining of Achilles tendons at day 1, 2 and 7 post-injury either treated with cmRNA$^{BMP-7}$ or vehicle. A trend of increased BMP-7 levels was observed in cmRNA$^{BMP-7}$ treated tendons compared to vehicle treated tendons (n≥3). (D) H.E. staining of Achilles tendons at day 1, 2 and 7 post-injury, treated either with cmRNA$^{BMP-7}$ or vehicle. Scale bars are equivalent to a length of 400 μm. (E) Mean intensity of collagen type I immunostaining of Achilles tendons at day 1, 2 and 7 post-injury either treated with cmRNA$^{BMP-7}$ or vehicle. Higher intensity at day 2 and at day 7 in cmRNA$^{BMP-7}$ treated tendons compared to vehicle treated tendons (n≥3). (F) Mean intensity of collagen type III immunostaining of Achilles tendons at day 1, 2 and 7 post-injury either treated with cmRNA$^{BMP-7}$ or vehicle. Lower collagen type III intensity in cmRNA$^{BMP-7}$ treated tendons at day 7 compared to vehicle treated tendons (p=0.057, n≥3). (G) Ratios of mean intensity of collagen type I to collagen type III immunostaining of Achilles tendons at day 1, 2 and 7 post-injury either treated with cmRNA$^{BMP-7}$ or vehicle. Trend towards higher collagen I/III ratios in cmRNA$^{BMP-7}$ treated tendons compared to vehicle treated tendons (n≥3).

Figure 17:
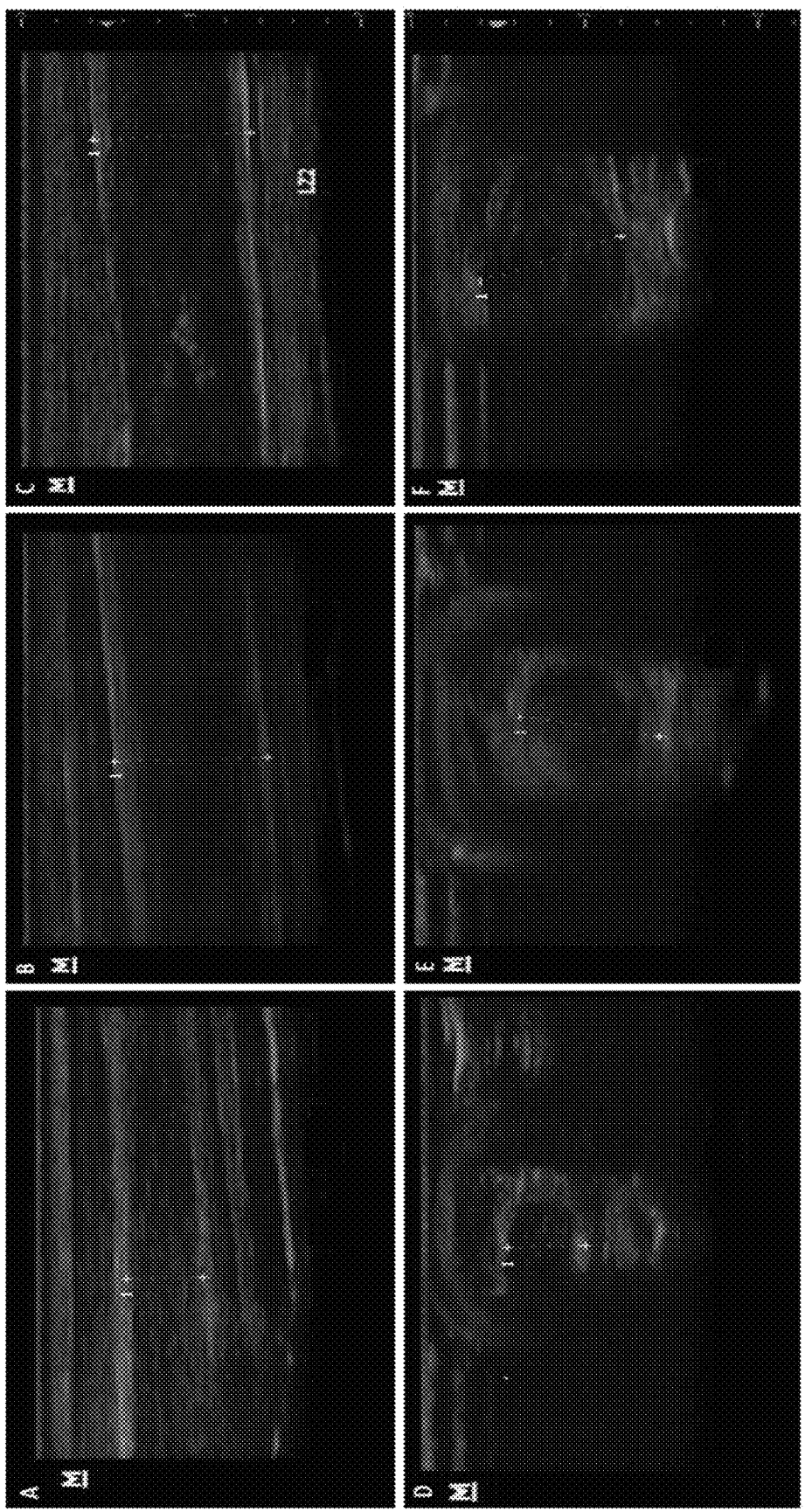
Figure 17:
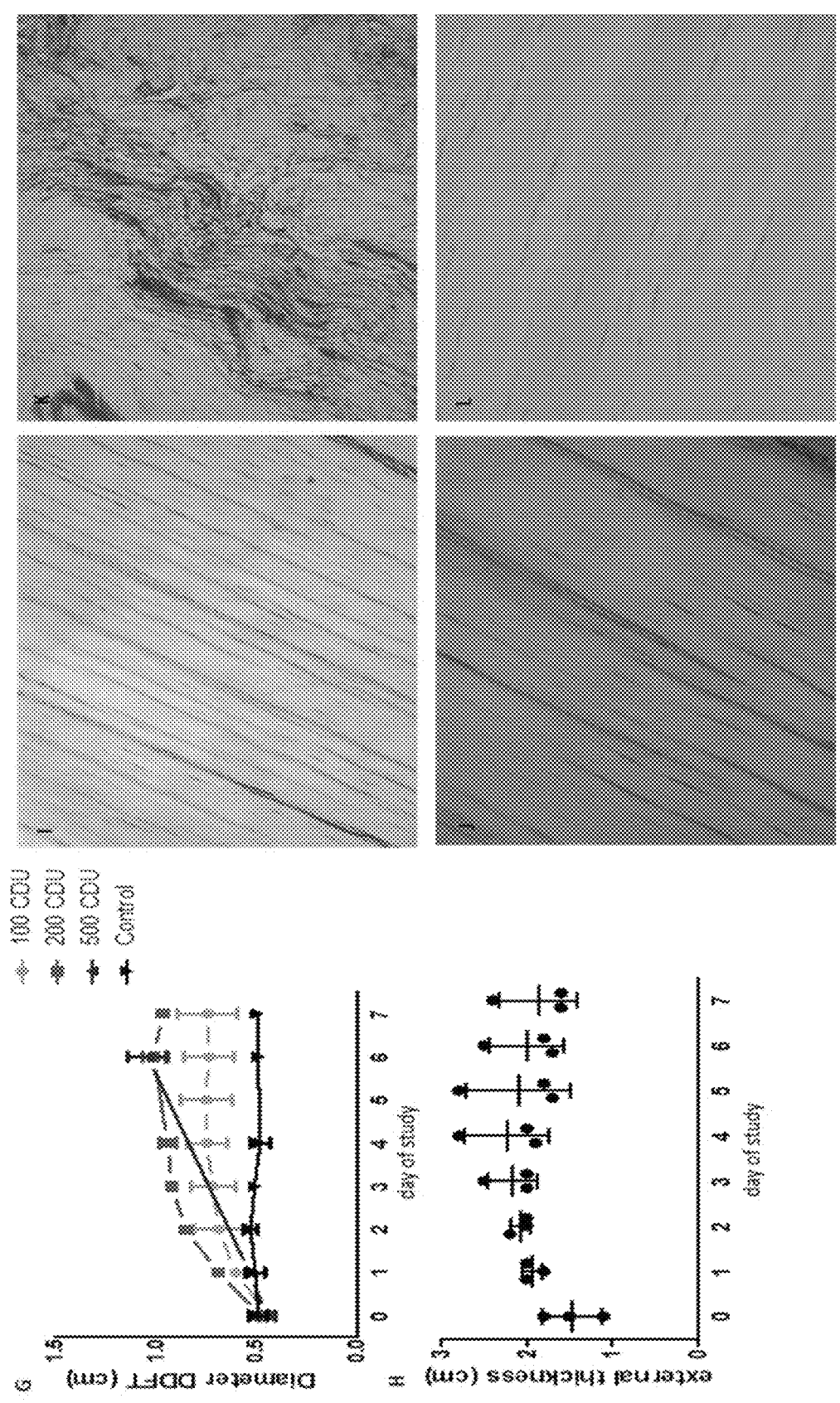

FIG. 17 Pathology of collagenase-gel induced tendon defects in sheep. (A-F) Longitudinal (A-C) and transversal (D-F) ultrasound images of a sheep's injured hind limb. (A, D) Longitudinal and transversal ultrasound image at day 0 before collagenase injection, (B, E) 3 and (C, F) 7 days after collagenase-gel injection (100 CDU). (G) Diameter analysis during experimental period of tendons injected with either 100, 200 or 500 CDU and untreated contralateral controls. Data is represented as the mean±SD. Diameter of DDFT increased proceedingly in all groups after collagenase application. (H) External thickness analysis of sheep treated with 100 CDU during experimental period. Data is represented as the mean±SD. External thickness reached maximum (1.5-fold) 4 days post collagenase injection. (I-L) H.E. staining of intact (I, J) and injured (K, L) ovine tendon. (I, J) Typical fiber structure with tenocytes located between fibers. (K) Necrotic material, hematoma, inflammation and massive loss of fiber structure in the central area of the defect. Structure of adjusted fibers was still apparent although fibers were swollen and connections between fibers appeared loosened. (L) Cell number and cell density in surrounded mostly intact areas was increased. (I, K Original magnification ×10, J, L Original magnification ×20)

Figure 18:
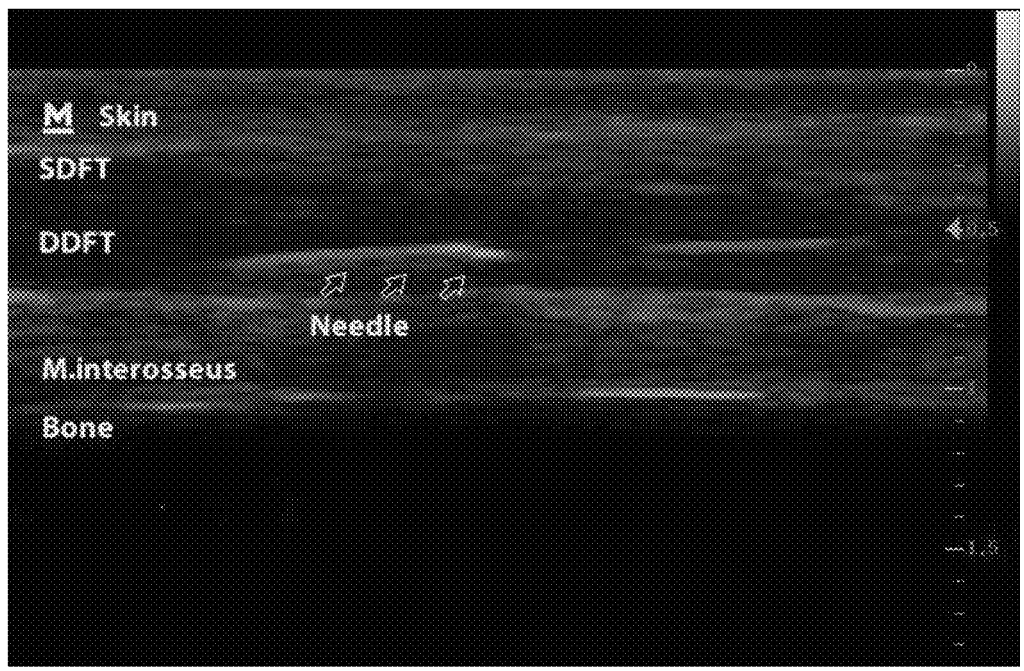

FIG. 18 Longitudinal ultrasound image of a sheep's hind limb. Needle was inserted in deep digital flexor tendon before collagenase injection was performed. (SDFT= Superficial Digital Flexor Tendon, DDFT=Deep Digital Flexor Tendon, M. interosseus=Musculus interosseus)

Figure 19:
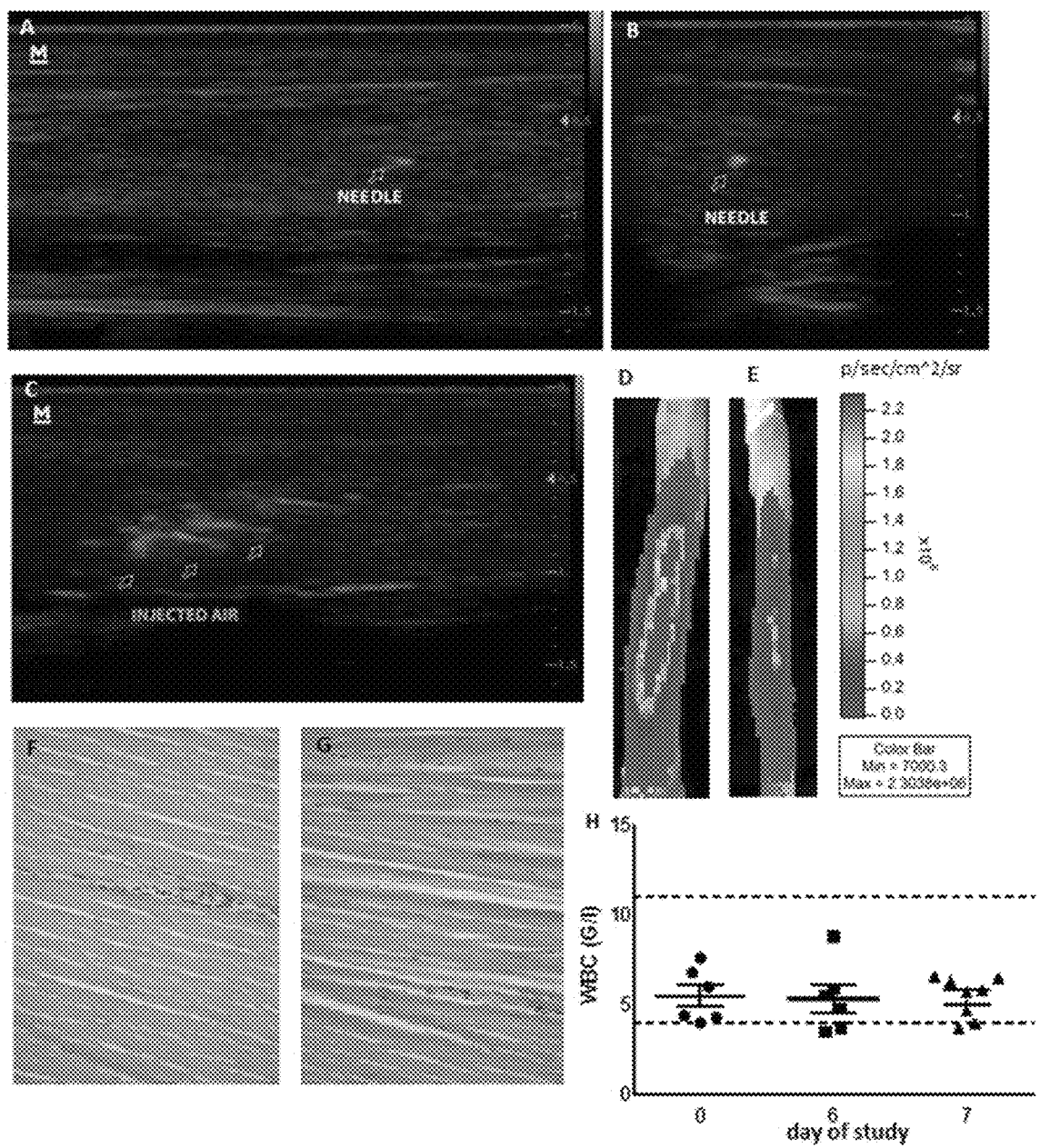

FIG. 19 Successful in vivo transfection of injured and intact tendons in sheep. (A, B) Longitudinal (A) and transversal (B) ultrasound image of a damaged DDFT on day 6 with needle inserted in the central part of the tendon. (C) Longitudinal ultrasound image just after SNIM-RNALUC (WO 2011/012316) injection. Injected air is visible in the central area of the tendon. (D, E) BLI of damaged (D) and intact (E) explanted contralateral ovine DDFT 24 hours after in vivo injection of 200 μg cmRNA$^{LUC}$ in each DDFT. Damage was induced by injection of 100 collagen digestion units. BLI was performed within 2 hours post euthanasia. (F, G) H.E. staining of intact cmRNA$^{LUC}$ treated tendon at the injection site (F) and 3 cm proximal to the injection site (G). Original magnification ×20. (H) White blood cell (WBC) analysis on day 0, day 6 and day 7. Dashed lines define reference range (5-11 G/l).

Figure 20:
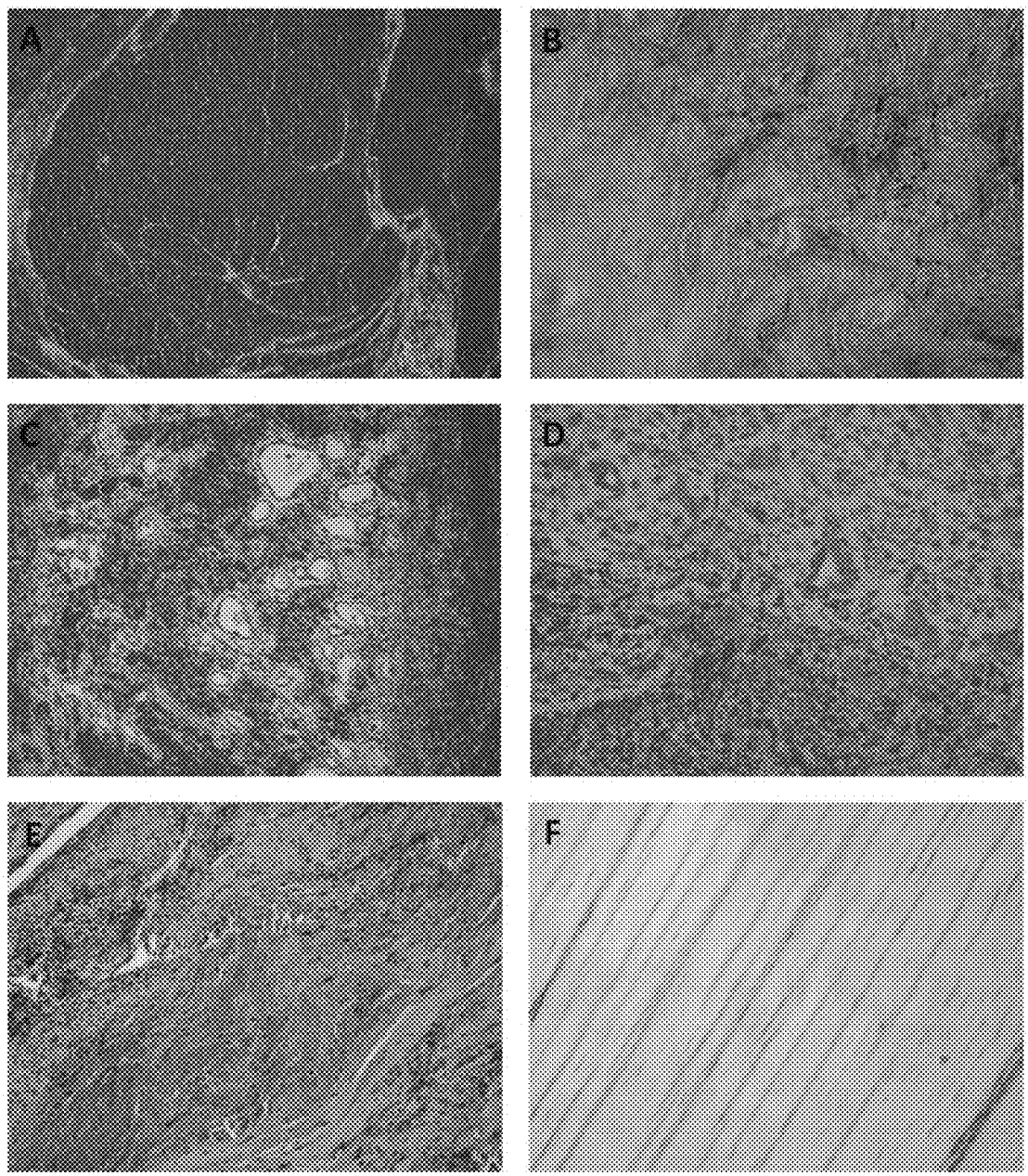

FIG. 20 Defect characterization 7 days after collagenase-gel application containing 200 CDU or 500 CDU (H.E. staining) (A) Hematoma in the central area of the defect. (B) Necrotic material, conglomeration of red blood cells as well as invaded inflammatory cells in peripheral area of the defect. (C) Neovascularization and (D) invasion of inflammatory cells in peripheral area of the hematoma. (E) Red blood cell accumulation between fibers close to the defect and massive inflammation. (F) The contralateral limbs' intact tendon with tenocytes located between parallel fibers. (A-C, E, F original magnification ×10, D original magnification ×20).

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Methodology of Ex Vivo Experiments (Especially Pertaining to Examples 1 to 9)

Tendon Harvest and Preparation

Tendon tissue of either slaughtered or euthanized animals were harvested within one hour post mortem and rinsed in ice cold Dulbecco's PBS (1×) containing 1% Penicillin/Streptomycin twice. Deep digital flexor tendons derived from cattle, horses or sheep and Achilles tendons derived from rats or pigs. Connective tissue was removed and major tendons were cut into slices (0.5 cm×3 cm).

RNA Synthesis

A codon optimized DNA sequence (e.g. SEQ ID No. 2) with known flanking sequences was cloned into a standard expression vector for in vitro mRNA production. To generate the template for in vitro transcription, the plasmid was linearized downstream of the poly (A) tail and purified using chloroform extraction and sodium acetate precipitation as described by Sambrook et al. (Sambrook, J., Fritsch, E. F., and Maniatis, T (1989) in Molecular Cloning: A Laboratory Manual. Cold Spring Harbor Laboratory Press, N.Y. Vol 1, 2, 3). Complete linearization of plasmid template was confirmed by 1% agarose gel electrophoresis. In vitro transcription was carried out with RiboMAX Large Scale RNA Production System—T7 (Promega, Germany) at 37° C. following the manufacturer's protocol. For in vitro transcription of chemically modified mRNA (cmRNA) 25% cytidine-5'-triphosphate and 25% uridine-5'-Triphosphate were replaced by 5-methylcytidine-5'-triphosphate (TriLink, USA) and 2-thiouridine-5'-triphosphate (TriLink, USA), respectively, in the reaction mixture (for more details see WO 2011/012316). Purification of mRNA was performed by chloroform extraction and size exclusion chromatography.

Ex Vivo Transfection and Cultivation mRNA was diluted in different solvents and different concentrations before the injection was performed slowly in parallel direction of the tendon fibers by using a 23 G needle for major tendons and 30 G insulin syringes for rat Achilles tendons. Transfected tendon slices were stored in tissue culture flasks with vented caps in DMEM (1×)+GlutaMAX medium containing 1% Penicillin/Streptomycin, 2% Nystatin and 10% FBS at 37° C. and 5% $CO_2$ immediately after SNIM®-RNA (WO 2011/012316) injection. Four to five samples were stowed per flask.

Bioluminescence Measurement

Firefly Luciferase (FFL) is a common reporter protein that is not endogenously present in mammals and can be detected easily by luminescent imaging. Luciferase catalyses the reaction of luciferin and oxygen which results in bioluminescence emission.

Bioluminescence was measured at indicated time points (24 h, 48 h, 72 h, 168 h) using a Xenogen IVIS In-Vivo Imaging System 100 (Caliper Life Science, USA). D-Luciferin substrate diluted in Dulbecco's PBS (1×) was added to the cell culture flasks (100 µg D-Luciferin/ml medium) one hour prior to the measurement of luciferase activity. The measurement was operated in the field of view A with high sensitivity (Binning 16) and an exposure time of 1 minute. Living Image® 2.50 software was used for analysis.

Betagalactosidase (LacZ) Staining

Betagalactosidase is another common reporter protein used for analysis of gene expression. The cleavage of XgaI substrate results in a blue precipitate. Tendon slices were injected with 100 µg modified LacZ-RNA dissolved in 250 µl isotonic saline. LacZ staining was performed 24 hours post injection.

BMP7 Immunohistochemistry

Rat Achilles tendons were injected with 30 µg modified BMP-7-mRNA (25% 2-thiouridine, 25% 5-methylcytidine) dissolved in 40 µl 1× concentrated HEPES-buffered glucose (HBG, 25 mM HEPES, glucose 5% m/v) pH 7.4. After 24 hours of incubation tendons were embedded in Tissue-Tek, deep frozen in liquid nitrogen and stored at −80° C. Cryo-sectioning and Immuno-histochemistry were performed by Sophistolab AG (Muttenz, Switzerland).

Radioisotopic Imaging $I^{125}$ marked mRNA was injected into porcine tendon (Pierce Iodination Tubes). Measurement was performed with 1×1 Binning, FOV 10 and an exposure time of 1 min by using an In-Vivo Xtreme BI 4MP, X-ray System (Bruker).

The following Examples 1 to 9 represent ex vivo experiments.

Figure 1:
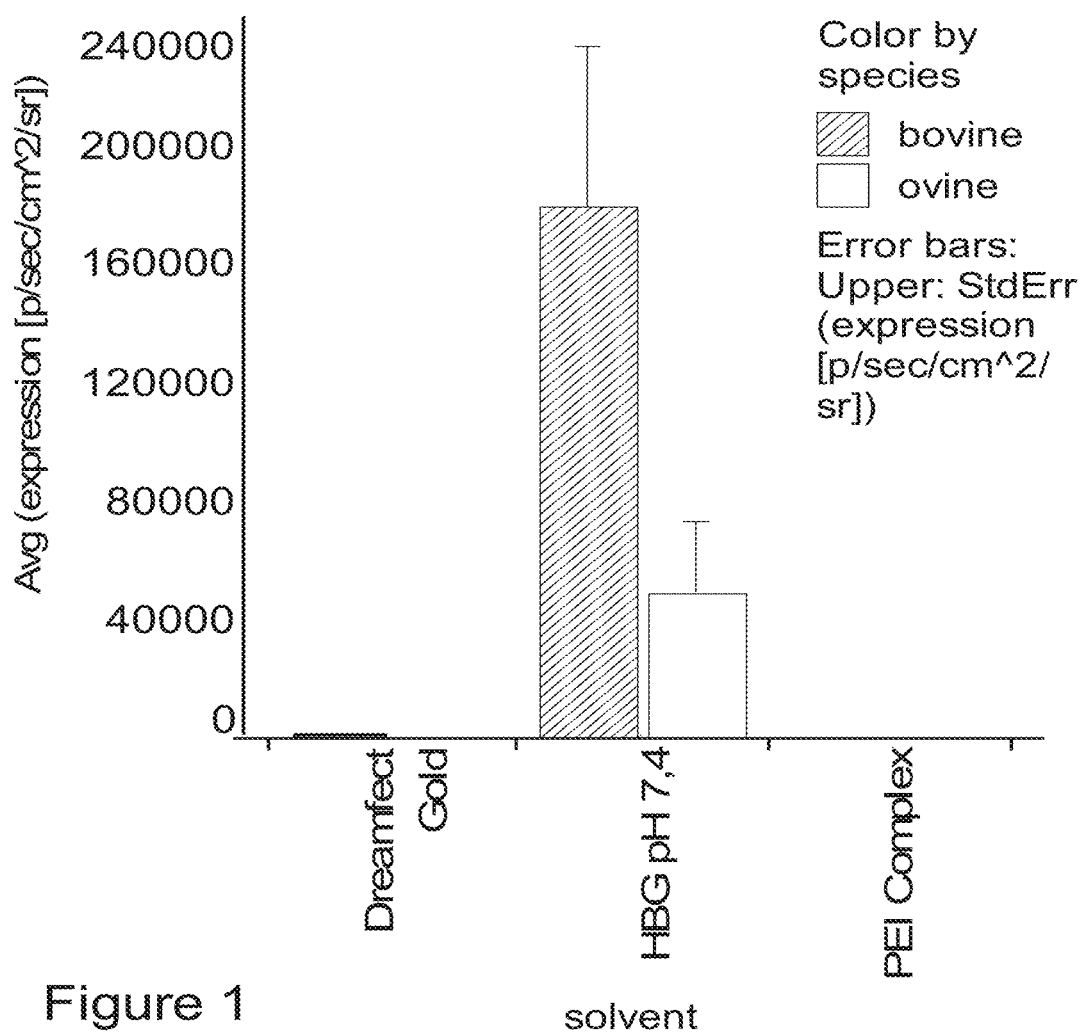
FIG. 1 shows the expression of naked mRNA coding for firefly luciferase (FFL) in HBG pH 7.4 (1×) versus mRNA coding for firefly luciferase (FFL) in different carrier systems in bovine and ovine tendon (see Example 1).

Example 1: Comparison of Bioactivity of Naked mRNA with Lipid- and Polymer-Complexed mRNA after Injection into Bovine and Ovine Tendon Explants 50 µg of naked modified mRNA encoding firefly luciferase (FFL) (25% 2-thiouridine, 25% 5-methylcytidine) was injected into five bovine or ovine tendon explants, respectively, and compared with modified FFL mRNA complexed with DreamFect$^{FM}$ Gold (4 µl/1 µg RNA, bovine tendon explants) or branched PEI 25 kDa (N/P=10, ovine tendon explants). The results of this experiment are shown in FIG. 1.

Luciferase expression of naked modified FFL mRNA was 295.5-fold higher than for DreamFect$^{FM}$ Gold and 122.5- fold higher than for branched PEI. The results of this experiment are shown in FIG. 1.

Example 2: Bioactivity of Naked mRNA in Tendon Explants of Different Species

Figure 2:
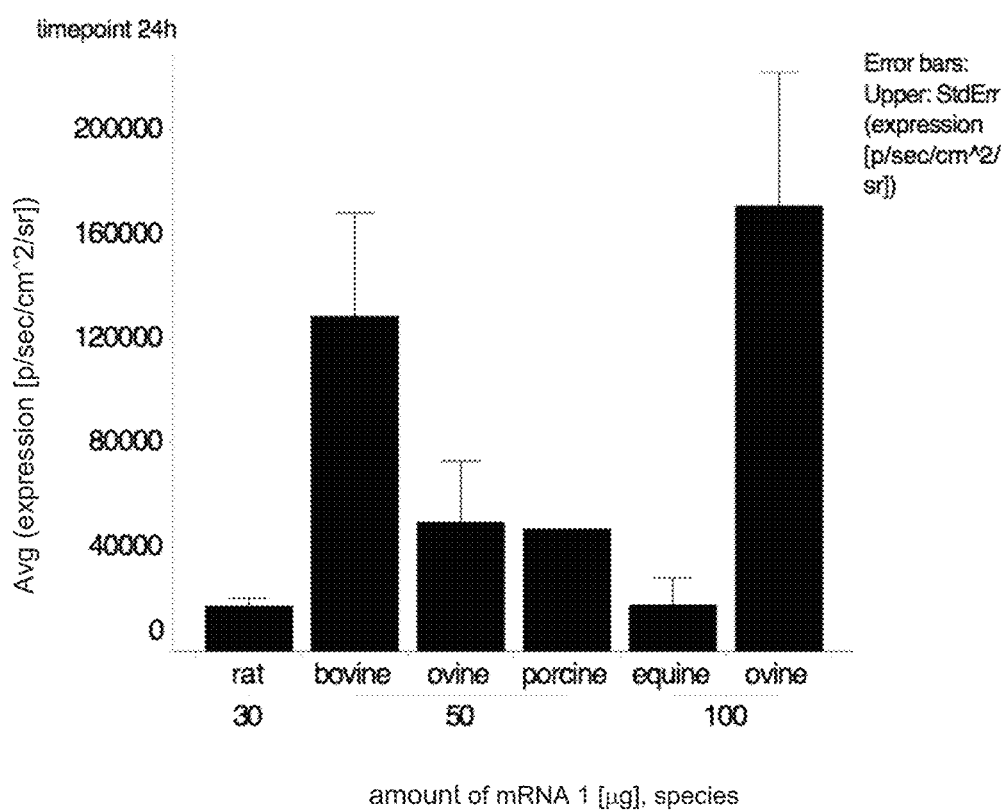
FIG. 2 shows the expression of firefly luciferase (FFL) encoding mRNA in tendons of different species (see Example 2). The data represent the expression level 24 h after injection.

Modified FFL-mRNA (25% 2-thiouridine, 25% 5-methylcytidine) was injected in tendon explants derived from rats, cattle, sheep, horses and pigs. Either 30 µg (rat tendons), 50 µg (bovine, ovine and porcine tendons) or 100 µg (equine and ovine tendons) of modified FFL-mRNA was injected. The results are shown in FIG. 2. Luciferase expression was observed in all different species that had been tested.

Example 3: Expression Kinetics of Different mRNA at Different Doses

Figure 3:
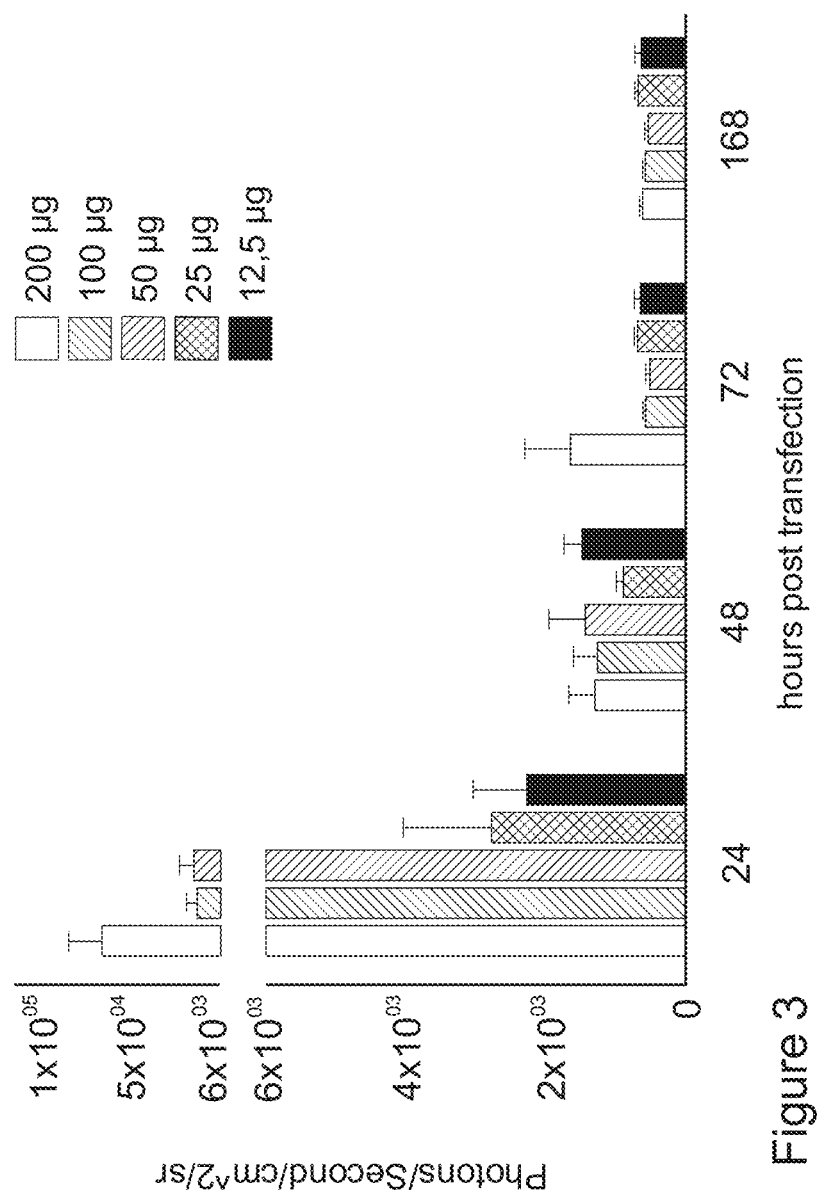
FIG. 3 shows the kinetics of the expression of firefly luciferase (FFL) encoding mRNA of different mRNA concentrations in ovine tendon explants (see Example 3).

200 µg, 100 µg, 50 µg, 25 µg and 12.5 µg modified FFL-mRNA (25% 2-thiouridine, 25% 5-methylcytidine) were dissolved in 250 µl isotonic saline. Bioluminescence was measured at determined time points (24 h, 48 h, 72 h, 168 h). The results are shown in FIG. 3. The highest expression of each dose tested was detected after 24 hours post transfection. Expression decreased during 7 days post transfection.

Figure 4:
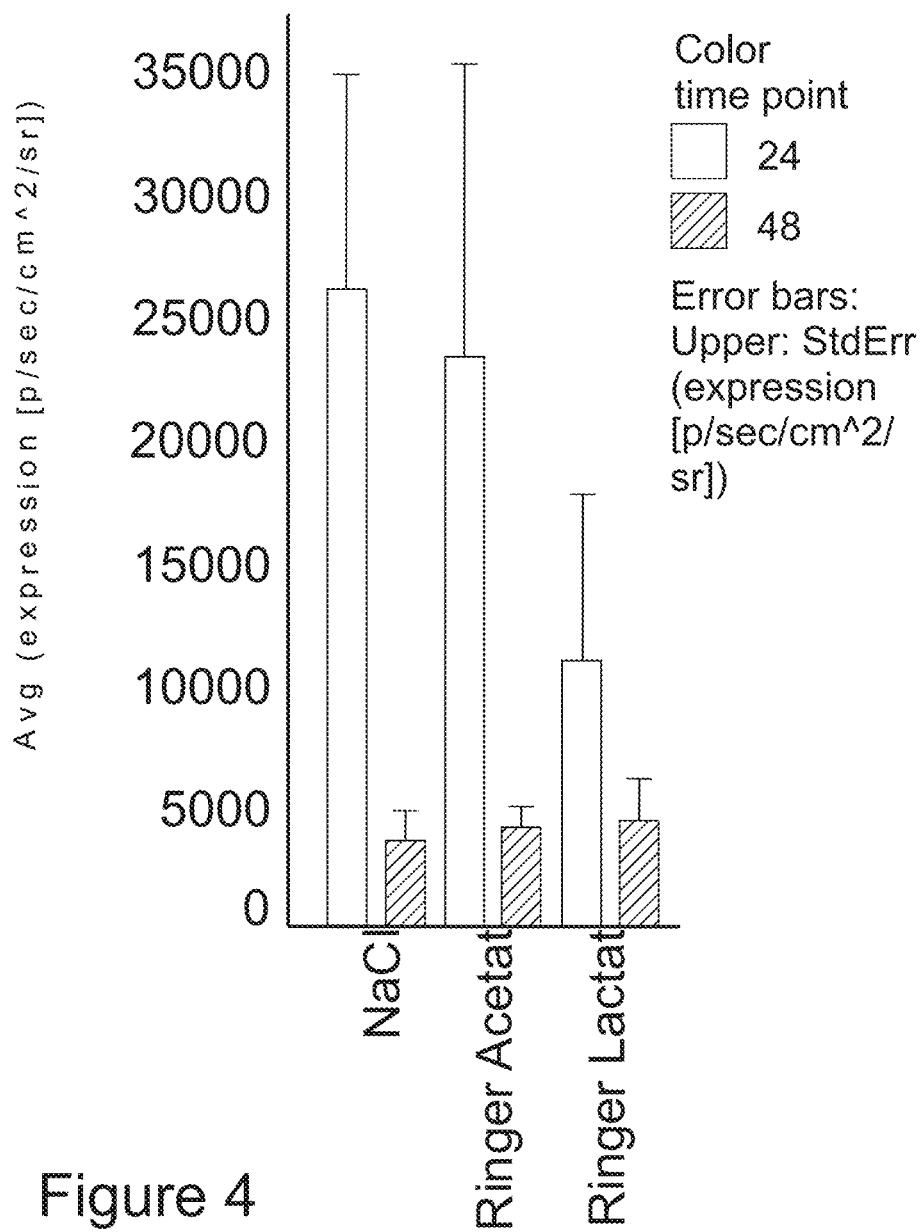
FIG. 4 shows the comparison of different solvents used for naked mRNA injection into bovine tendon explants (see Example 4).

Example 4: Comparison of Different Solvents Used for Naked mRNA Injection into Tendon Explants 50 µg modified FFL-mRNA (25% 2-thiouridine, 25% 5-methylcytidine) was dissolved in 200 µl (c=0.25 mg/ml) of different solvents and injected into five tendon explants per group. The results are shown in FIG. 4. The highest Bioluminescence levels after 24 hours were detected when modified FFL-mRNA was dissolved in saline solution compared to other solutions. Significant expression was also observed in Ringer Acetate or Ringer Lactate.

Example 5: Comparison of Modified FFL-mRNA Dissolved in Isotonic Saline, Water for Injection and HEPES Buffered Glucose (HBG 1×)

Figure 5:
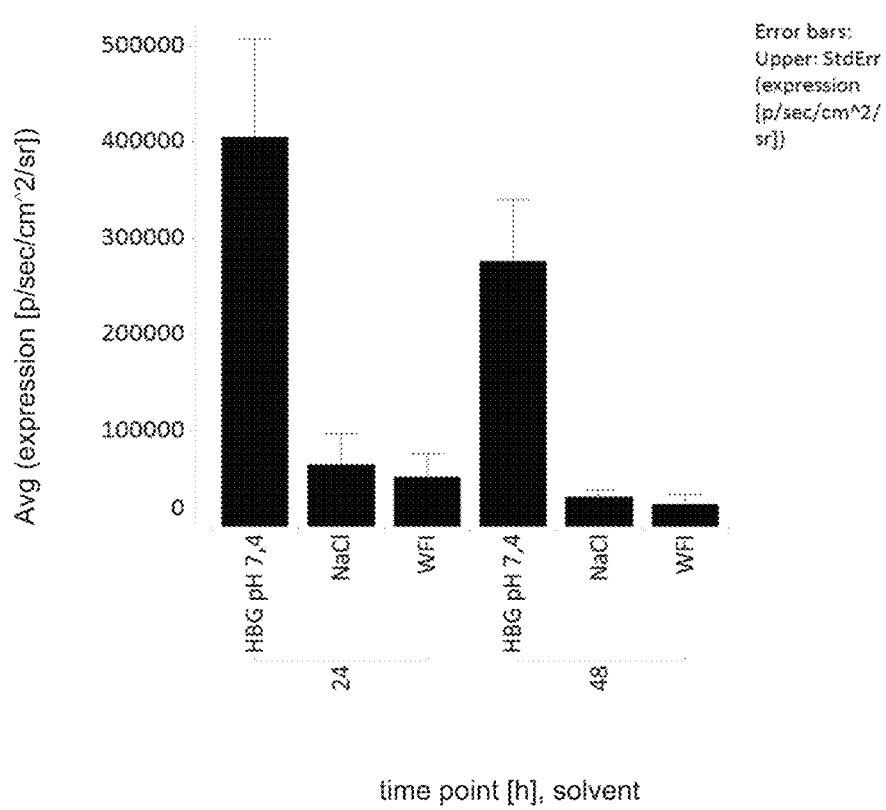
FIG. 5 shows a comparison of expression of firefly luciferase (FFL) encoding mRNA in bovine tendon explants when injected in water-for-injection (WFI), NaCl (isotonic saline) and HBG (1×) pH 7.4 (see Example 5).

50 µg modified FFL-mRNA (25% 2-thiouridine, 25% 5-methylcytidine) was dissolved in 100 µl (c=0.5 mg/ml) of HBG pH 7.4 (1×; 25 mM HEPES, glucose 5%), isotonic saline and water for injection (WFI) and injected into eight bovine tendon explants. Expression was highest in HEPES buffered glucose. The results are shown in FIG. 5. After 24 hours bioluminescence levels were 6.3-fold higher when modified FFL-mRNA was dissolved in HBG pH 7.4 (1×) compared to modified FFL-mRNA dissolved in isotonic saline and 7.8-fold higher compared to modified FFL-mRNA dissolved in WFI. After 48 hours the expression was 9-fold higher by using HBG pH 7.4 (1×) compared to isotonic saline and 11-fold higher compared to WFI.

Example 6: Comparison of Different HBG Concentrations

Figure 6:
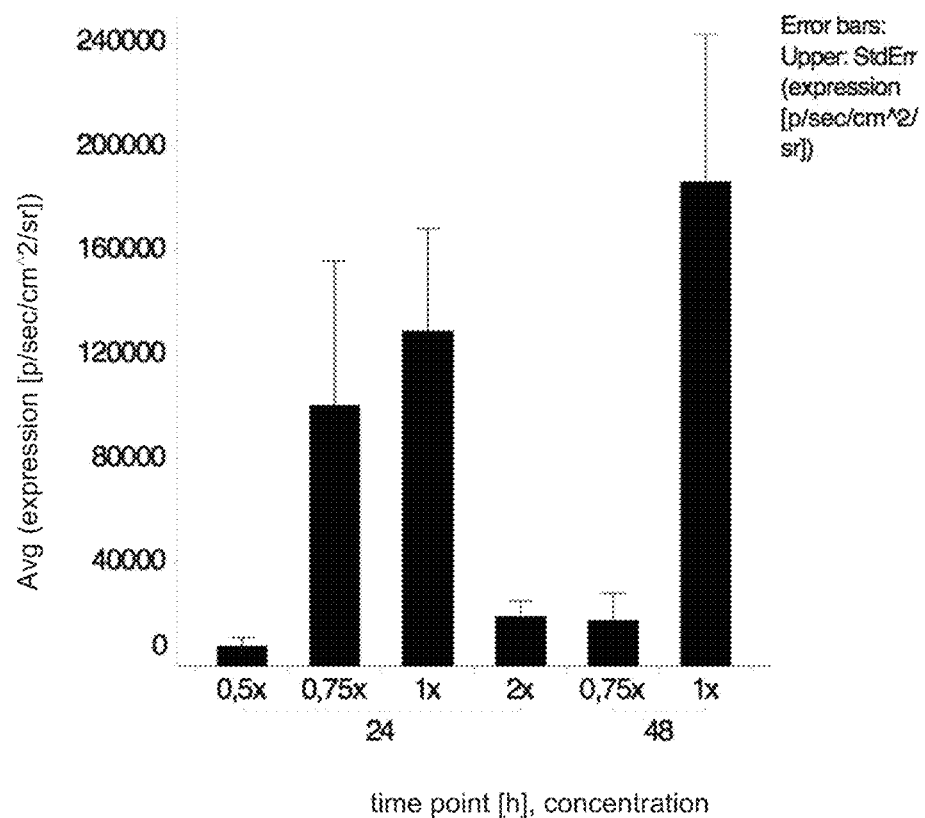
FIG. 6 shows the influence of the HBG concentration on the expression level of firefly luciferase (FFL) encoding mRNA in bovine tendon explants (see Example 6).

50 µg modified FFL-mRNA (25% 2-thiouridine, 25% 5-methylcytidine) was dissolved in 100 µl (c=0.5 mg/ml) of 0.5×, 0.75×, 1× or 2× concentrated HBG pH 7.4 and was injected into five bovine tendon explants. The results are shown in FIG. 6. HBG 1× concentrated resulted in 17.7-fold higher expression compared to 0.5×, 1.4-fold higher compared to 0.75× and 7.3-fold higher compared to 2× after 24 hours and 10.4-fold higher expression compared to 0.75× after 48 hours.

Example 7: Comparison of Different Modified FFL-mRNA Amounts

Figure 7:
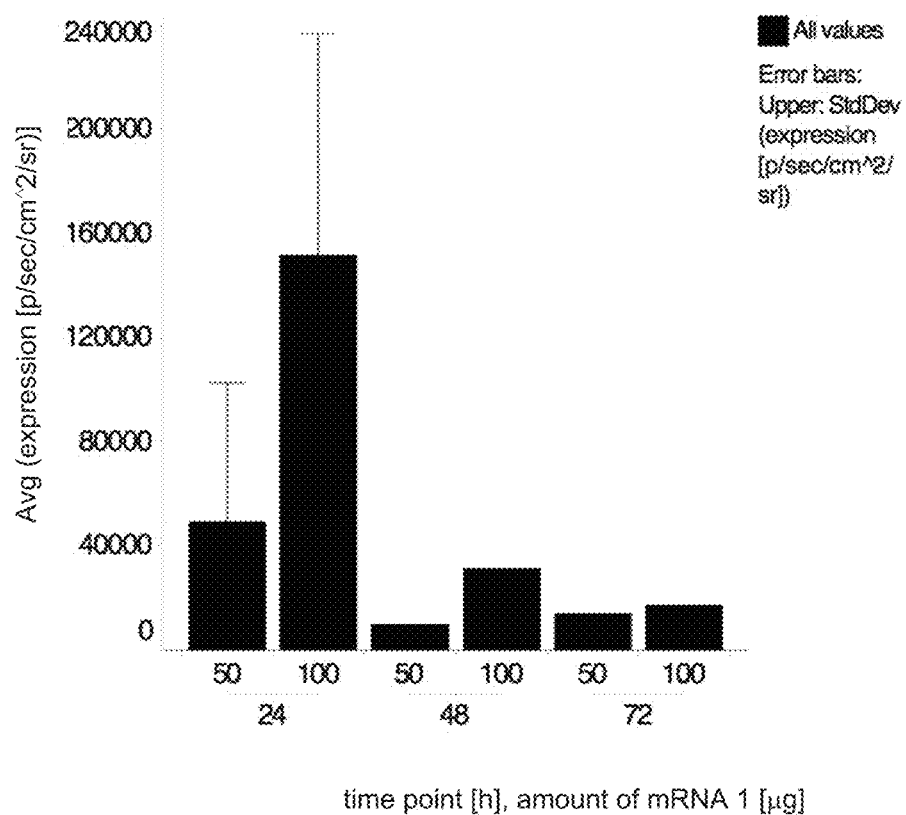
FIG. 7 shows the influence of the amount of mRNA on the expression level of firefly luciferase (FFL) encoding mRNA in ovine tendon explants (see Example 7).

50 µg and 100 µg modified FFL-mRNA (25% 2-thiouridine, 25% 5-methylcytidine) were dissolved in 100 µl HBG pH 7.4 (1×) and injected into ovine tendon explants. The results are shown in FIG. 7. 100 µg modified mRNA resulted in 3-fold higher expression after 24 hours, 3.2-fold higher expression after 48 hours and 1.2-fold higher expression after 72 hours compared to 50 µg mRNA. Luciferase expression is therefore dose dependent.

Example 8: Comparison of Different mRNA Concentrations

Figure 8:
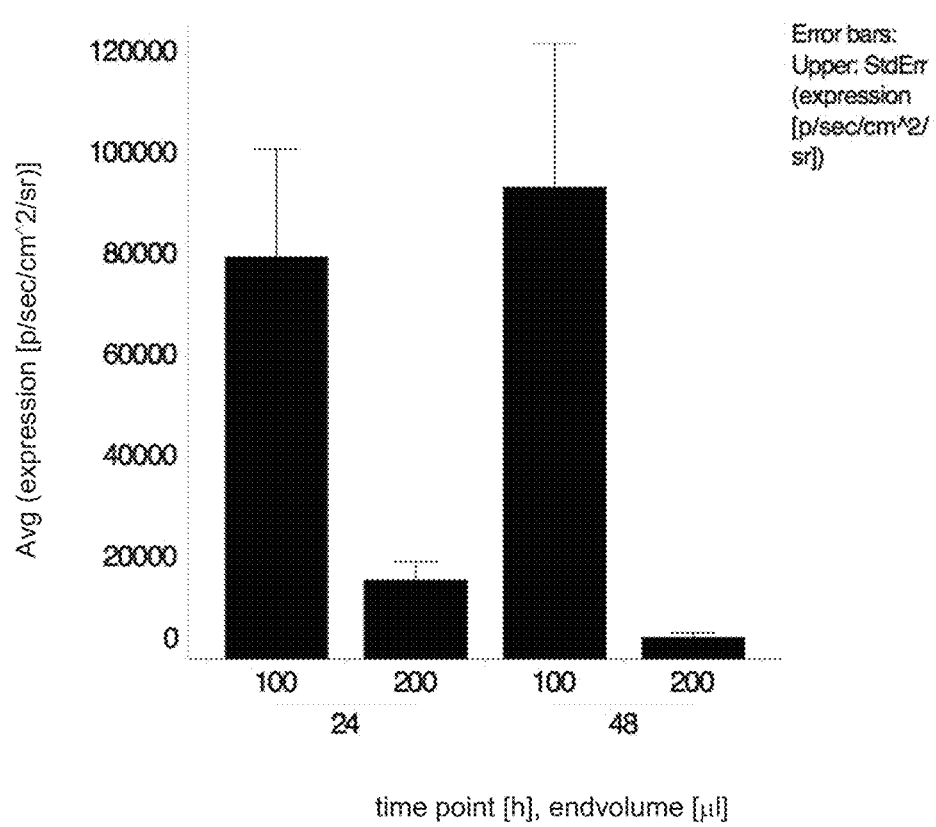
FIG. 8 shows the influence of the mRNA concentration on the expression level of firefly luciferase (FFL) encoding mRNA in bovine tendon explants (see Example 8).

50 µg modified FFL-mRNA (25% 2-thiouridine, 25% 5-methylcytidine) was dissolved in 100 µl (c=0.5 mg/ml) and in 200 µl (c=0.25 mg/ml) HBG pH 7.4 (1×) and injected into bovine tendon explants. The results are shown in FIG. 8. Increasing the mRNA concentration c=0.5 mg/ml resulted in an 5.1-fold higher expression after 24 hours and 21.2-fold higher expression after 48 hours compared to the lower mRNA concentration of c=0.25 mg/ml.

Figure 9:
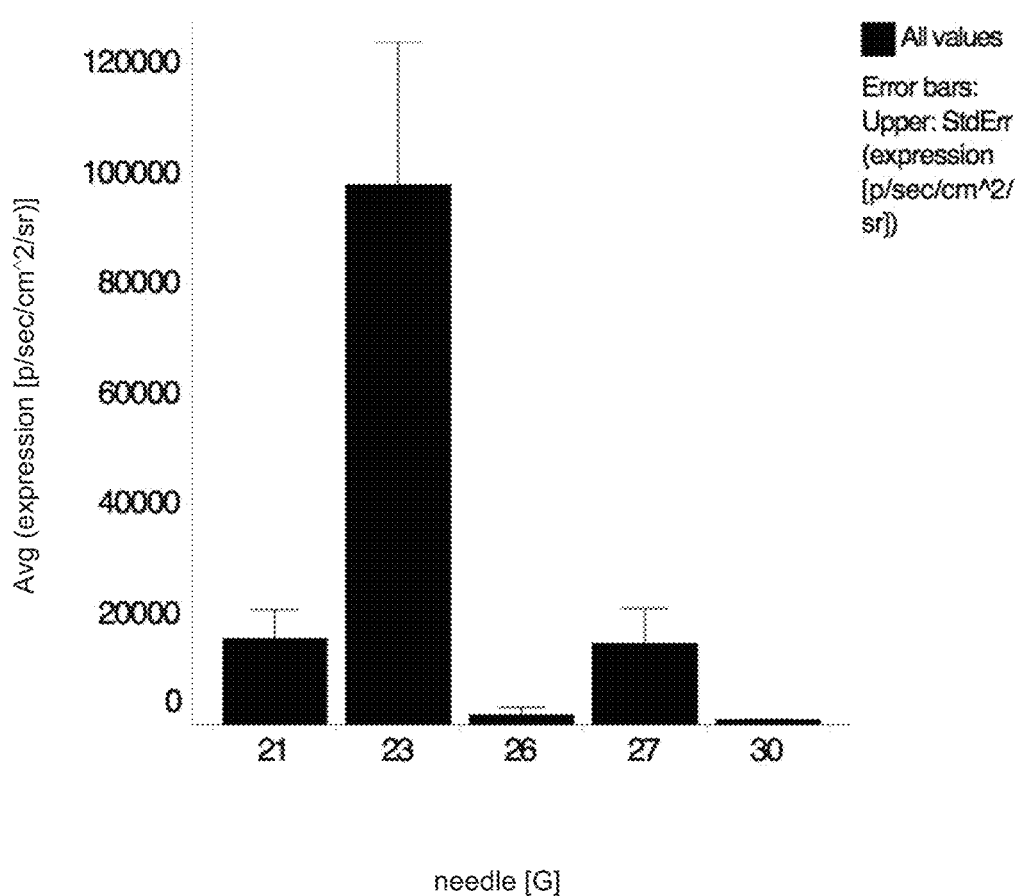
FIG. 9 shows the influence of the needle size on the expression level of firefly luciferase (FFL) encoding mRNA in ovine tendon explants (see Example 9).

Example 9: Comparison of Different Needle Sizes that were Used for Injection in Ovine Tendon Explants The injection was performed with either 21 G, 23 G, 26 G, 27 G or 30 G needles. The results are shown in FIG. 9. The highest expression occurred when 100 µg (0.25 mg/ml) modified FFL-mRNA was injected by using a 23 G needle. High expression was also detected with a 30 G needle in rat tendons.

The following Example 10 represents in vivo experiments.

Example 10: Luciferase Expression in Intact and Damaged Ovine Tendons

Methodology of In Vivo Experiments
Tendon Defect Induction
Either 500, 200 or 100 CDU (collagen digestion units) of collagenase type 1A was injected into the deep digital flexor tendons (hind limb) of mature female Merino sheep. The injection was performed under ultrasound guidance.
In Vivo Transfection and Tendon Harvest
Six days after the collagenase injection modified FFL-mRNA (25% 2-thiouridine, 25% 5-methylcytidine) diluted in HBG pH 7.4 (1×) was injected into healthy and damaged deep digital flexor tendons. Modified FFL-mRNA (250 µg) was applied in two separate injections of 150 µl (proximal and distal of the defect) under ultrasound guidance.
On the next day tendons were harvested within one hour post euthanasia. Connective tissue and tendon sheath was removed.
Bioluminescence Measurement
Harvested tendons were immediately incubated in D-luciferin-solution (100 µg D-luciferin/ml PBS (1×)) at 37° C. and 5% $CO_2$ for one hour before bioluminescence imaging was performed by using a Xenogen IVIS In-Vivo Imaging System 100 (Caliper Life Science, USA)

The measurement was operated in the field of view A with high sensitivity (Binning 16) and an exposure time of 1 minute. Living Image® 2.50 software was used for analysis.
The results are shown in FIG. 10 a to d. Luciferase expression was detected in intact tendons and in mild, moderate and even severe damaged tendons.

Example 11: LacZ Expression in Ovine Tendons

Tendon explants were injected with 100 µg modified LacZ-RNA dissolved in 250 µl isotonic saline. LacZ staining was performed 24 hours post injection. The cleavage of XgaI substrate results in a blue precipitate. Untreated ovine tendon explants were used as controls. The results are shown in FIG. 11 A to D.

Example 12: BMP-7 Expression in Rat Tendons

Rat Achilles tendons were injected with 30 µg chemically modified BMP-7-mRNA (25% 2-thiouridine, 25% 5-methylcytidine; SEQ ID NO. 3) dissolved in 40 µl 1× concentrated HEPES-buffered glucose (HBG, 25 mM HEPES, glucose 5% m/v) pH 7.4. After 24 hours of incubation tendons were embedded in Tissue-Tek, deep frozen in liquid nitrogen and stored at −80° C. Cryosectioning and BMP-7 immunohistochemistry was performed. The results are shown in FIGS. a12 A and B.

Example 13: Imaging of Radioisotopically Labeled mRNA $I^{125}$ marked mRNA was injected into porcine tendon (Pierce Iodination Tubes). Measurement was performed with 1×1 Binning, FOV 10 and an exposure time of 1 min by using an In-Vivo Xtreme BI 4MP, X-ray System (Bruker) 30 min after injection. The results are shown in FIG. 13.
Further Materials and Methods (Especially Pertaining to Examples 14 to 18)
Ex Vivo Transfection, Cultivation and Bioluminescence Imaging
Deep Digital Flexor Tendons (DDFT) derived from horses, cattle, sheep or pigs and Achilles tendons derived from rats. Tendons were harvested within one hour after animals had been euthanized (horses, sheep, rats) or slaughtered (pigs and cattle) and rinsed twice in ice cold Dulbecco's phosphate-buffered saline (DPBS) (Life Technologies GmbH Darmstadt, Germany) containing 1% penicillin/streptomycin (PAA Laboratories GmbH Pasching, Austria). Chemically modified naked mRNA either encoding for luciferase ($cmRNA^{LUC}$), β-galactosidase ($cmRNA^{LacZ}$) or human bone morphogenetic protein 7 ($cmRNA^{BMP-7}$ (25% 2-thiouridine, 25% 5-methylcytidine); SEQ ID NO. 3) was diluted in different solvents and different concentrations. Injection of cmRNA was performed in parallel direction of tendon fibers using 23 G needles (Sterican, B.Braun Melsungen AG, Germany) and 1 ml Injekt-F syringes (B.Braun Melsungen AG, Germany) for major tendons and 30 G Insulin syringes (BD Micro-Fine, Becton, Dickinson and Company, Franklin Lakes, USA) for rat Achilles tendons. The $cmRNA^{LUC}$ was diluted in different solvents and prepared using commercially available solutions and standard laboratory chemicals (Table 2). Hepes-buffered-glucose (HBG) (Sigma-Aldrich Chemie Schnelldorf, Germany) was adjusted to pH 7.4 and prepared in four different concentrations, namely 2.5%, 3.75%, 5% and 10%. The $cmRNA^{LacZ}$ and the $cmRNA^{BMP-7}$ were prepared in saline solution only. Complexed $cmRNA^{LUC}$ was prepared using Dreamfect$^{FM}$ Gold (OZ Biosciences Marseille, France) as recommended by the manufacturer (10 µg cmRNA$^{LUC}$/40 µl Dreamfect$^{FM}$ Gold) and using branched polyethyleneimine (brPEI) 25 kDa (Sigma-Aldrich Schnelldorf, Germany) at an N/P-ratio of 1:10 using 25 µg cmRNA$^{LUC}$.

Transfected tendon specimen were stored in T75 tissue culture flasks (TPP Trasadingen, Switzerland) in 50 ml DMEM (1×)+GlutaMAX medium (Life Technologies Darmstadt, Germany) containing 1% penicillin/streptomycin (PAA Laboratories GmbH Pasching, Austria), 2% nystatin (Sigma-Aldrich Chemie Schnelldorf, Germany) and 10% FBS (Life Technologies Darmstadt, Germany) at 37° C. and 5% $CO_2$ immediately after cmRNA injection.

Bioluminescence imaging (BLI) was conducted at determined points of time, namely 24, 48 and 72 hours after transfection, using a Xenogen IVIS In-Vivo Imaging System 100 (Caliper Life Science, USA). D-Luciferin substrate (S039, SYNCHEM, Felsberg/Altenburg, Germany) diluted in Dulbecco's PBS (1×) was added to the cell culture flasks (100 µg D-Luciferin/ml medium) one hour prior to the measurement of luciferase activity. The measurement was operated in the field of view A with high sensitivity (Binning 16) and an exposure time of one minute. Living Image® 2.50 software was used for data analysis.

Histological Processing of Ex Vivo Cultivated Tendon Explants

Staining for β-galactosidase activity was performed 24 hours after the corresponding cmRNA was injected according to the protocol of Dai et al. (Journal of orthopaedic research: official publication of the Orthopaedic Research Society. 2003; 21:604-9). Tendon specimen were fixed on ice for 30 minutes in 0.5% glutardialdehyde (Carl Roth Karlsruhe, Germany) and 2 mM magnesium chloride hexahydrate (Carl Roth Karlsruhe) in DPBS, adjusted to pH 7.4 and subsequently washed twice in rinsing buffer (100 mM HEPES, 5 mM DTT (Dithiotreitol, Sigma-Aldrich Chemie Schnelldorf, Germany), 1 mM $MgSO_4$ (Magnesium sulfate heptahydrate, Carl Roth Karlsruhe), 2% Triton X-100 (Carl Roth Karlsruhe), pH 8.0) at room temperature for 30 minutes and then rinsed at 50° C. for one hour. Tendon specimen were subsequently incubated in X-Gal staining solution (1 mg/ml 5-Bromo-4-Chloro-3-indolyl 3, Sigma-Aldrich Chemie), 2 mM $MgCl_2$, 5 mM $K_3Fe(CN)_6$ (Potassium ferricyanide (III), Carl Roth Karlsruhe), 5 mM $K_4Fe(CN)_6$ (Potassium hexacyanoferrate(II) trihydrate, Carl Roth Karlsruhe) in DPBS, pH 7.4) overnight in a non-$CO_2$ incubator. Finally tendons were fixed in 4% formaldehyde (Roti Histofix, Carl Roth Karlsruhe), dehydrated, embedded in paraffin and counterstained for hematoxylin.

For BMP-7 immunohistochemistry (IHC) tendons were embedded in Tissue-Tek® O.C.T.™ Compound (Sakura Finetek Staufen, Germany), snap frozen in liquid nitrogen and stored at −80° C. Cryosections were prepared and immunohistochemistry was performed by an external laboratory (Sophistolab AG Muttenz, Switzerland) using a rabbit polyclonal BMP-7 antibody (ab56023, abcam plc Cambridge, UK) as primary antibody.

In Vivo Studies in Intact and Injured Rat Achilles Tendons

All experiments were approved by the local ethics committee for animal experiments and adhered to the international guidelines for the care and treatment of laboratory animals. Female Sprague Dawley rats (4 month of age, bodyweight between 300 g and 340 g, Janvier Labs Saint-Berthevin, France) were group-housed under a 12:12 h light-dark circle with food and water ad libitum. 16 rats were used for Luciferase reporter protein kinetics in intact Achilles tendons and 24 rats were used to test the therapeutic potential of BMP-7 in injured Achilles tendons.

To determine Luciferase reporter protein expression in intact rat Achilles tendons, animals were anesthetized using isoflurane inhalation with air and $O_2$ as carrier gases (isoflurane 3-5 vol % in an inhalation chamber for induction followed by 1.5-2.5 vol % using an inhalation mask for maintenance). Different doses of cmRNA$^{LUC}$ (0, 10, 20, 40 µg; dose volume 10 µl) were then injected into the right Achilles tendon (n=4 rats/dose group). At day 1, 2 and 7 post cmRNA$^{LUC}$ injection in vivo bioluminescence imaging was performed using Photon Imager™ (Biospace Lab Nesles la Vallée, France). BLI was conducted 15 minutes after D-Luciferin substrate (L-8220 dissolved in 0.9% saline, Biosynth Staad, Switzerland) was administered intraperitoneally (150 mg/kg, 5 ml/kg). Images were acquired using 10 minutes of integration time. No filter was used. Quantification was performed using a region of interest defined manually (Achilles tendon) and the results were expressed as total counts. M$^3$Vision software (Biospace Lab, Nesles la Vallée, France) was used for data analysis. On day 7, rats were sacrificed with $CO_2$, Achilles tendons were explanted immediately and Luciferase activity was measured again in tendon explants.

Therapeutic cmRNA$^{BMP-7}$ (25% 2-thiouridine, 25% 5-methylcytidine; SEQ ID NO. 3) was applied directly into injured, i.e. dissected and surgically repaired Achilles tendons to investigate the influence on early tendon healing. Prior to surgery rats received a subcutaneous (sc.) injection of 0.05 mg/kg buprenorphine (Temgesic®, Reckitt Benckiser Wallisellen, Switzerland). Surgery was performed under inhalation anesthesia as described above. The left leg was prepared for aseptic surgery and then fixed in a custom-made holder to stabilize the ankle at a 90° position with the foot facing downwards. An incision was made above the left Achilles tendon. The superficial Achilles tendon was exposed and was fully dissected in the midportion between the calcaneus side and the muscle insertion. The Plantaris tendon was left intact. An end-to-end anastomosis of the Achilles tendon stumps was then performed applying a Three Loop Pulley pattern suture using a non-absorbable monofil filament (Prolene® 5-0, ⅜ reverse cutting needle P3, Ethicon, Johnson & Johnson Medical, Norderstedt, Germany). Subsequently, either cmRNA$^{BMP-7}$ (100 µg) or vehicle was administered intra-tendinously proximal and distal to the anastomosis with a dose volume per injection site of 5 µl (BD Micro-Fine 30 G Insulin Syringes, Becton, Dickenson and Company, Franklin Lakes, USA). The subcutaneous layer and the skin were then closed by a continuous suture technique with an interrupted intracutaneous suture using an absorbable synthetic thread (Safil® 6-0, B. Braun Melsungen AG, Germany). Animals were then allowed to wake up on a heating pad to aid the return to normal body temperature. Buprenorphine was again administered every 8-12 h post-surgery for up to two days.

On day 1, 2, and 7 post-surgery each 4 cmRNA$^{BMP}$-7-treated and 4 vehicle-treated rats were sacrificed with $CO_2$ and both injured and intact contralateral Achilles tendons were explanted. Achilles tendons were fixed overnight in 4% paraformaldehyde (Sigma-Aldrich Chemie Buchs, Switzerland), dehydrated with an ascending ethanol series, and embedded in paraffin (Paraplast Xtra, Leica Wetzlar, Germany). For immunohistochemistry Anti-BMP-7 antibody (ab56023, abcam plc Cambridge, UK), polyclonal Anti-Collagen I antibody (ab 34710, abcam plc Cambridge, UK) and polyclonal Anti-Collagen III antibody (ab7778, abcam plc Cambridge, UK) were used as primary antibodies.

Biotinylated Goat Anti-Rabbit IgG (BA-1000, Vector Laboratories, Peterborough, UK) were used as secondary antibodies. Staining was induced by peroxidase (biotin-labeled) activity. Sections were counterstained with hematoxylin (VWR International, Dietikon, Switzerland). DAB staining in microscopic images was thresholded and mean gray values of positive pixels were evaluated. Analysis was performed with Fiji/Image J Version 1.49k.

In Vivo Studies in an Ovine Model of Acute Tendon Injury

All experiments were approved by the local ethics committee for animal experiments and adhered to the international guidelines for the care and treatment of laboratory animals. For large animal experiments, nine female mature Merino sheep, 4-7 years of age, bearing between 72 kg and 87 kg, were group housed under a 12:12-h light-dark circle. Hay and water was provided ad libitum. All large animals had no clinical or ultrasonographic evidence of tendon injury.

For tendon defect induction a collagenase-gel model was chosen (Watts, Equine veterinary journal. 2012; 44:576-86; Smith, Equine veterinary journal. 2014; 46:4-9). The metatarsal area of both hind limbs was clipped, shaved and aseptically prepared before either 500, 200 or 100 collagen digestion units (CDU) of collagenase type 1A (from *Clostridium histolyticum* C0130, Sigma-Aldrich Chemie Schnelldorf, Germany) were injected into the Deep Digital Flexor Tendon (DDFT) of the left hind limb. Collagenase was diluted in Dulbecco's PBS (1×), filter sterilized and merged with 50 µl of thrombin solution (Component 2, Tissucol Duo S Immuno, Baxter UnterschleiRheim, Germany). The injection was performed with a lateral approach in the mid-tarsal area under ultrasound guidance (Mindray DP 50 vet; Sonoring Schmitt-Haverkamp, Germany) using a 23 gauge needle and a Duploject system (Baxter Germany) in which the collagenase-thrombin-solution was combined with 50 µl fibrinogen-solution (Component 1, Tissucol Duo S Immuno, Baxter Germany) during injection. FIG. 18 shows a longitudinal ultrasound image of a sheep's hind limb while the needle was inserted in DDFT just before the injection was performed. Ensuring that the gel formation process had been completed, the needle was not withdrawn until 30 seconds had passed after injection. A suture was applied where the needle was inserted.

Antibiotics (Veracin® compositum 3 ml/50 kg, Albrecht, Aulendorf, Germany) were administered intramuscularly every second day for five days. 0.3 mg Buprenorphin-hydrochloride (Buprenovet® Multidose 0.3 mg/ml, Bayer HealthCare, Leverkusen, Germany) was applied subcutaneously every twelve hours for two days and Ketoprofen 3 mg/kg (Romefen® PR 10%, Merial, Hallbergmoos, Germany) every twenty-four hours for five days as analgesics. Frequent ultrasound and daily clinical examination was performed by two veterinarians. A portable Mindray DP 50 vet ultrasound machine (Sonoring Schmitt-Haverkamp, Germany) with a linear probe (5-12 MHz) was used. Ultrasound examinations were performed with the sheep bearing weight on the examined foot. Diameter of the DDFT was measured in the mid-tarsal area, 2 cm below the applied suture. External thickness was measured from medial to lateral in the same mid-tarsal area by using a digital caliper in group treated with 100 CDU.

Six days after collagenase injection, cmRNA$^{LUC}$ diluted in HBG 5% was injected into healthy and damaged deep digital flexor tendons of both hind limbs. Procedure was again performed under general anesthesia. The cmRNA$^{LUC}$ was applied in two separate injections of 100 µg (500 CDU group, n=2), 200 µg (200 CDU group, n=2) or 250 µg (100 CDU group, n=2) cmRNA (proximal and distal area of the defect) under ultrasound guidance. Some air was drawn in the syringe and injected in the end of the injection to ensure that syringe and needle were emptied completely. Ketoprofen 3 mg/kg (Romefen® PR 10%) was administered intravenously during anesthesia.

On the next day, the sheep were euthanized by an intravenous overdose of pentobarbital (Euthadorm®, CP-Pharma, Burgdorf, Germany) and tendons were harvested within one hour post euthanasia. Connective tissue and tendon sheath was removed. Harvested tendons were immediately incubated in D-Luciferin-solution (100 µg D-Luciferin/ml PBS (1×)) at 37° C. and 5% $CO_2$ for one hour before bioluminescence imaging was performed by using a Xenogen IVIS in-vivo Imaging System 100 (Caliper Life Science, USA). The measurement was operated in the field of view A with high sensitivity (Binning 16) and an exposure time of one minute. Living Image® 2.50 software was used for the analysis. Tendons were fixed in 4% paraformaldehyde for 24 hours, dehydrated with an ascending ethanol series, and embedded in paraffin. In intact tendons five parts of cmRNA$^{LUC}$ injected area were chosen, as well as parts 3 cm proximal and distal to the injection site. In injured tendons central and peripheral areas of the defect were selected. 3 µm sections were stained with hematoxylin and eosin for histopathological examination.

Blood was taken on day 0, day 6 (before mRNA application) and day 7 (before euthanasia) and full blood count as well as liver and kidney test values were analyzed by an external veterinary laboratory.

Statistical Analysis

All statistical analyses were performed with GraphPad Prism 5. Results are presented as the mean±SEM, with n equal to the number of samples per group. Differences between groups were analyzed for significance using Mann Whitney U test, with significance attained at p<0.05. Results in FIG. 17G, H and Tab. 3 are presented as the mean±SD.

Example 14: Injection of Naked cmRNA Results in High Protein Expression in Tendon Explants Naked cmRNA dissolved in saline solution was injected into tendon explants to investigate, whether chemically modified messenger RNAs could transfect tendon tissue thereby resulting in the expression of therapeutic protein(s). An initial ex vivo experiment was conducted in explanted porcine tendons. Tendon tissue was transfected through direct injection of cmRNA$^{LUC}$ following which, the explants were then incubated (24 hours, 37° C., 5% $CO_2$) and luciferase activity was measured subsequently. Using this methodology, Luciferase expression was detected in specimen injected with cmRNA$^{LUC}$, but not in untreated control tendons or in tendons injected with saline solution only. Based on these promising findings, further experiments were conducted in explants of different animal species to investigate, whether the concept of ex vivo transfection could be successfully applied to more mammalians. Interestingly, besides expression in porcine tendon explants, injection of naked cmRNA$^{LUC}$ resulted also in distinct Luciferase expression in explanted tendons of sheep, cattle, horses, and rats (FIG. 14A). Notably expression patterns revealed a particular distribution with highest Luciferase activity at the injection site and a slim, tube-like distribution within the entire explant.

In a next set of experiments, dose-dependent expression of Luciferase could be demonstrated in porcine tendons after injection of cmRNA$^{LUC}$ (FIG. 14B). Luciferase expression directly correlated with the amount of injected mRNA and was 10-fold higher at a used cmRNA$^{LUC}$ amount of 200 µg compared to 25 µg (FIG. 14B). To identify the transfected cells, cmRNA encoding for β-galactosidase was injected into porcine tendon explants and tissues stained for β-gal activity at 24 hours after incubation. Similar to luciferase expression, most of the β-gal expression was localized both in tenocytes and connective tissue cells close to the injection site (FIG. 14D, 14F). In control tendons injected with cmRNA$^{LUC}$ no positive β-gal staining could be observed (FIG. 14E, 14G).

Encouraging results with reporter genes (Luciferase and β-galactosidase) prompted us to investigate the applicability of this technology to produce therapeutic proteins. Human BMP-7 was selected as a therapeutic target, as its potential to increase healing processes due to stimulating effects on tenocytes has been discussed recently (Yeh, Journal of cellular biochemistry. 2008; 104:2107-22; Pauly, Journal of shoulder and elbow surgery/American Shoulder and Elbow Surgeons. 2012; 21:464-73). Further in vivo experiments were intended to be conducted in rats, hence cmRNA encoding for human BMP-7 was injected into rat Achilles tendons and BMP-7 immunohistochemistry (IHC) was performed after a cultivation period of 24 hours. Using this methodology, BMP-7 positive signals were found in vascular walls, connective tissue and tenocytes in BMP-7 transfected tendon specimen (FIG. 14 H, J). Indeed control specimen revealed to be slightly positive as well, but merely in vascular walls (FIG. 14 I, K).

Example 15: Glucose Enhances, Amino-Acids Impair Luciferase Expression in Tendon Explants As initial experiments showed strongest expression in bovine tendon tissue it was continued by using bovine tendon explants for further experiments. Investigating expression kinetics, peak expression after 24 hours and clear drop off (2-fold) after 48 hours were observed. At 72 hours post injection, luciferase expression reduced to almost background levels (FIG. 15A).

It was further investigated if tendon transfection and transgene expression could be further potentiated via use of different commercially available and/or standard laboratory solutions containing amino acids, electrolytes and/or sugars. It was hypothesized that (1) osmotic gradients may increase intracellular electrolyte influx and thereby intracellular uptake of cmRNA, (2) providing cells with additional amino acids may enhance the translation of cmRNA, (3) precipitating mRNA with ammonium acetate may result in a "depot effect" thereby enabling relatively long-term expression. Furthermore, colloidal solutions were used to test the influence of large molecules on transfection of tendon tissue. As highest expression levels were observed 24 hours after cmRNA$^{LUC}$ injection, this point of time was selected for the comparison of different solvents.

Our results indeed reveal strong influence of the used solvent/electrolyte on the resulting Luciferase expression. This effect was most prominent when comparing electrolyte and/or glucose-containing solutions with solutions containing amino-acids (FIG. 15B). Noticeably, glucose-containing solution such as HEPES buffer containing 5% glucose (HBG 5%) resulted in highest Luciferase expression compared to saline solution (15-fold, P<0.05) or amino-acids-containing solution (57-fold compared to Aminosteril plus, p<0.05). cmRNA$^{LUC}$ in ammonium acetate solution completely abolished the expression of luciferase. Reasoning, whether concentration of glucose influences transfection efficacy, highest Luciferase expression was observed at a glucose concentration of 5% and which decreased several fold when glucose concentration was either increased (20-fold less) or decreased (50-fold) (FIG. 15 C). To verify that these findings were transferable to other species, experiments in porcine tendons were continued. It was further examined, whether mixing of glucose and saline may additionally enhance transfection efficacy. Mixing 5% glucose with saline (NaCl+ 5% Gluc) did not affect Luciferase expression compared to HBG 5% solution (FIG. 15D).

As mRNA application was recently used to be conducted with mRNA formulated in carrier systems, transfection efficacy of cmRNA$^{LUC}$ complexed with lipid and polymer carriers in different species was furthermore examined. Interestingly, cmRNA$^{LUC}$ complexed with DreamFect Gold resulted in expression levels only comparable to w/t specimen. Moreover, Luciferase expression was 22-fold lower in tendons treated with cmRNA$^{LUC}$ complexed with brPEI compared to cmRNA$^{LUC}$ dissolved in saline solution.

Example 16: Naked Chemically Modified mRNA Efficiently Transfects Intact Rat Achilles Tendons In Vivo To test the translation of our ex vivo findings in vivo cmRNA$^{LUC}$ dissolved in the best performing solution (HBG containing 5% glucose, adjusted to a pH of 7.4) was injected into Achilles tendons of rats at 4 different doses (40, 20, 10 and 0 µg). Expression of Luciferase protein was measured by in vivo BLI at 1, 2 and 7 days post injection (FIG. 16A). Dose-dependent Luciferase expression was also observed in rat Achilles tendons in vivo and expression kinetics were comparable with the ex vivo data in porcine tendons (FIG. 14B) and bovine tendons (FIG. 15A). Highest expression was observed at 24 hours post cmRNA injection which declined over time to extremely low but detectable levels by day 7 (FIG. 16B).

Example 17: Naked cmRNABMP-7 Positively Affects Early Healing in Injured Rat Achilles Tendons In Vivo The therapeutic potential of human BMP-7 was investigated in rats on the healing of dissected and surgically repaired Achilles tendons. Histological examination of healing Achilles tendons was performed 1, 2 and 7 days after surgery and injection of mRNA$^{BMP-7}$ (25% 2-thiouridine, 25% 5-methylcytidine; SEQ ID NO. 3) or vehicle (HBG 5%).

Tendon samples were stained for BMP-7 using immunohistochemistry (IHC) to evaluate, whether mRNA$^{BMP-7}$ injection induced the expression of therapeutic protein. Compared to untreated intact contralateral Achilles tendons, BMP-7 expression increased in all tendons that underwent surgical procedure from day 1 until the end of the study at day 7, no matter whether they received cmRNA$^{BMP-7}$ or vehicle. However, BMP-7 expression levels were higher during the whole experimental period in cmRNA$^{BMP-7}$-treated tendons compared to vehicle-treated tendons (FIG. 16C).

At day 1 post-surgery histopathological examination of the injured Achilles tendon revealed an inflammatory reaction with immigration of granulocytes and more or less necrotic areas with or without hematoma in both groups. Increased mitotic activity of tenocytes and fibroblasts was observed in both groups, indeed more distinct in animals being treated with cmRNA$^{BMP-7}$. At day 2 post-surgery comparable increase in inflammation and tissue proliferation was apparent in both groups. At day 7 post-surgery further proliferative progress was apparent, however all samples exhibited fibrous "bridge-like" tissue in the anastomosis region (FIG. 16D, E).

Analysis of IHC for collagen type I revealed a slight decrease in expression from day 1 to day 2 in tendons being treated with vehicle, whereas mean intensity in tendons treated with cmRNA$^{BMP-7}$ remained stable. The decrease was followed by a very slight increase until day 7 in both groups. At day 2 and day 7 the intensity of collagen type I was thereby higher in tendons treated with cmRNA$^{BMP-7}$ compared to tendons treated with vehicle only (FIG. 16E). In contrast, the expression of collagen type III decreased from day 1 to day 2 in both groups, but more distinct in the cmRNA$^{BMP-7}$ group, followed by a pronounced increase in the vehicle group from day 2 to day 7. At day 7 the signal intensity for collagen type III was considerably lower in tendons treated with cmRNA$^{BMP-7}$ than in vehicle-treated tendons (p=0.057) (FIG. 16F). Additionally, collagen type I to collagen type III ratios of tendons treated with cmRNA$^{BMP-7}$ were higher at day 2 and at day 7 compared to the vehicle group (FIG. 16G).

Example: 18: Naked cmRNA Efficiently Transfects Injured and Intact Tendons in Large Animals In Vivo Tendinopathy is characterized by matrix disorganization, hypercellularity, fiber disorientation and vascular ingrowth. As these conditions could not be compared to those of intact or surgically injured tendons, cmRNA's capability of transfecting tendons in a large animal model of tendinopathy was ought to investigate. Collagenase-gel in three different doses (100 CDU, 200 CDU, 500 CDU) was therefore injected into the left Deep Digital Flexor Tendon (DDFT) of anesthetized elderly sheep to generate a defect with partial failure, resembling clinical characteristics of preliminary stages of tendinopathies in humans and horses. Subsequent clinical and ultrasound examination was performed at different time-points (FIG. 17A-F). Ultrasound examination furthermore revealed increasing inhomogeneity in all groups. Diameter of DDFTs treated with 100 CDU increased 1.57-fold from 0.44 cm±0.030 cm to 0.69 cm±0.126 cm within 2 days and to 0.74 cm±0.150 cm at day 7 (FIG. 17G). DDFTs' diameter of sheep treated with 200 CDU and 500 CDU increased even stronger, with peaking size on day 6 (1.01 cm±0.0566 cm for 200 CDU, 1.04 cm±0.099 cm for 500 CDU). Due to our pain treatment, only slight lameness was objected in sheep treated with 100 CDU within the first three days after collagenase-gel injection. However, the limbs' external thickness increased 1.5-fold within 4 days from 1.47 cm±0.351 cm to 2.23 cm±0.493 cm, but consistently decreased again to 1.87 cm±0.462 cm at day 7 (FIG. 17H). Sheep treated with 200 CDU or 500 CDU suffered from moderate lameness within four days post collagenase injection and from slight lameness until day 7.

Tendon defects were investigated histologically at day 7 (animals euthanized on this day), revealing smaller necrotic areas with loss of fiber structure, conglomerations of red blood cells and some invading inflammatory cells in the central area of the defect (FIG. 17K) as well as smaller conglomerations of red blood cells and isolated inflammatory cells between tendon fibers in the adjacent area of the defect in tendons treated with 100 CDU. Moreover, adjacent fibers seemed swollen and connections between fibers appeared loosened. Cell number and cell density were increased (FIG. 17I) compared to intact tendons (FIG. 17L). Tendons injected with 200 CDU and 500 CDU were characterized by large-area necrosis and hematoma with immense loss of fiber structure. Moreover, massive invasion of inflammatory cells could be objected (FIG. 18). Necrotic area in tendons injected with 500 CDU were extended to one third of the tendon, in tendons injected with 200 CDU around one quarter of the tendon was affected.

At day 6, i.e. 24 hours before euthanasia, cmRNA$^{LUC}$ (500 µg in 100 CDU group, 400 µg in 200 CDU group and 200 µg in 500 CDU group) was injected into the defect of the left injured (FIG. 19A, B) and into the right intact tendon under ultrasound guidance. Injected air that had been withdrawn in the syringe together with cmRNA$^{LUC}$ made the application position visible by ultrasound (FIG. 17C). One day later sheep were euthanized and tendons were harvested for ex vivo BLI and histopathological examination. Luciferase expression was more widely distributed and intensive in the injured region than in healthy tissue of the contralateral tendon (FIG. 19D, E). The histopathological examination of cmRNA$^{LUC}$ treated intact tendons showed predominantly intact tendon tissue without pathological findings. Only a few small cellular conglomerations of macrophages and granulocytes could be detected (FIG. 19F). Tissue distal and proximal of the injection site was without any abnormalities (FIG. 19G). Lameness or tissue swelling could not be detected.

With regard to side-effects it has to be mentioned, that animals were clinically examined every day. No adverse effects became apparent due to the application of cmRNA. Furthermore, blood analysis was performed before and 24 hours after the application of cmRNA. Indeed no pathological changes became apparent and measured values of blood leucocytes were within the physiological range after mRNA application (FIG. 19H). Additionally full blood count, liver and kidney test values were analyzed (FIG. 20). No pathological findings due to cmRNA application could be identified.

Example 19: Further Discussion, Especially of Examples 14 to 18

Tendon injuries or degenerative tendinopathies are common in both animals and humans, especially in athletes (Kvist, Sports medicine (Auckland, NZ). 1994; 18:173-201). Achilles tendon and rotator cuff tendinopathies, for example, are frequently diagnosed among humans (Jarvinen, Foot and ankle clinics. 2005; 10:255-66, Herrmann, Acta chirurgiae orthopaedicae et traumatologiae Cechoslovaca. 2014; 81:256-66). The appearance of tendon damage is various. The occurrence is heterogenous and ranges from acute rupture to chronic tendinopathies. Medical reasons are multisided and predisposal factors are similar in humans and animals, such as overloading due to training or joint malposition, age, gender, genetics, body weight or endocrinopathies (Patterson-Kane, ILAR journal/National Research Council, Institute of Laboratory Animal Resources. 2014; 55:86-99, Perkins, New Zealand veterinary journal. 2005; 53:184-92, Baird, Connective tissue research. 2014; 55:275-81, Ippolito, Italian journal of orthopaedics and traumatology. 1975; 1:133-9, Magnan, Foot and ankle surgery: official journal of the European Society of Foot and Ankle Surgeons. 2014; 20:154-9). In numerous cases chronic damage caused by overuse or degenerative processes leads to an acute injury or even tendon rupture (Jarvinen, Scandinavian journal of medicine & science in sports. 1997; 7:86-95). Beside degenerative processes, a failed healing after tendon injury is also discussed as pathogenesis of tendinopathies (Rees, The American journal of sports medicine. 2009; 37:1855-67, Watts, Equine veterinary journal. 2012; 44:576-86).

The natural healing potential of tendon tissue is low due to hypocellularity, hypovascularity and a low metabolic rate compared to other soft tissues (Bray, Journal of anatomy. 1996; 188 (Pt 1):87-95, Sharma, Journal of musculoskeletal & neuronal interactions. 2006; 6:181-90, Liu, Tissue engineering Part B, Reviews. 2011; 17:165-76). The healing process is therefore extremely slow (James, The Journal of hand surgery. 2008; 33:102-12, Williams, Sports medicine (Auckland, NZ). 1986; 3:114-35); it usually takes months or years. The healing process moreover normally results only in tissue repair instead of regeneration as the original tensile strength and elasticity is usually not regained (Sharma, Foot and ankle clinics. 2005; 10:383-97). Recovery is therefore rarely fully functional (Sharma, Journal of musculoskeletal & neuronal interactions. 2006; 6:181-90, Hogan, The Journal of the American Academy of Orthopaedic Surgeons. 2011; 19:134-42) and the risk of re-injury or even a tendon rupture is highly increased (Mast, The Surgical clinics of North America. 1997; 77:529-47).

Treatment methods are numerous and can be categorized in conservative and surgical therapy. Besides rest and bandaging followed by controlled exercise in cases of acute injury, conservative therapy methods can also be intra lesion application of various substances such as corticosteroids (Muto, Journal of orthopaedic research: official publication of the Orthopaedic Research Society. 2014; 32:1297-304, Hart, Clinical journal of sport medicine: official journal of the Canadian Academy of Sport Medicine. 2011; 21:540-1), which is highly controversial; hyaluronic acid (Muneta, Journal of orthopaedic science: official journal of the Japanese Orthopaedic Association. 2012; 17:425-31, Foland, American journal of veterinary research. 1992; 53:2371-6) or glycosaminoglycans (Moraes, The Veterinary record. 2009; 165:203-5) that are components of the extracellular matrix in tendons. Furthermore, physical methods such as electromagnetic stimulation or shockwave therapy (Bosch, Equine veterinary journal. 2007; 39:226-31, Seeliger, European journal of medical research. 2014; 19:37) are used. Also various approaches using stem cell-based (Smith, Disability and rehabilitation. 2008; 30:1752-8, Martinello, Journal of orthopaedic research: official publication of the Orthopaedic Research Society. 2013; 31:306-14, Renzi, Research in veterinary science. 2013; 95:272-7) and growth factor-based therapies are investigated (Witte, Journal of the American Veterinary Medical Association. 2011; 239:992-7, Shah, Journal of orthopaedic research: official publication of the Orthopaedic Research Society. 2013; 31:413-20, Arguelles, The Veterinary record. 2008; 162:208-11, de Vos, British journal of sports medicine. 2011; 45:387-92).

The assumption that cytokines and growth factors play a key role during the healing process generated considerable research interest in growth-factor based gene therapy, namely that they stimulate cell proliferation as well as cell differentiation and formation of extracellular matrix components (Molloy, Sports medicine (Auckland, NZ). 2003; 33:381-94, Evans, Sports medicine (Auckland, NZ). 1999; 28:71-6, Grotendorst, International journal of tissue reactions. 1988; 10:337-44). Various ex vivo and in vivo experiments provided promising results, for example improved tendon healing in a rat Achilles tendon healing model after BMP-12 gene transfer (Majewski, Gene therapy. 2008; 15:1139-46) or a positive influence of platelet-rich plasma on core lesions of Superficial Digital Flexor Tendons (SDFT) in horses (Bosch, Journal of orthopaedic research: official publication of the Orthopaedic Research Society. 2010; 28:211-7). In recent years much research has been focused on DNA gene transfer in the field of growth factor based therapies (Majewski, Gene therapy. 2008; 15:1139-46, Nakamura, Gene therapy. 1998; 5:1165-70, Evans, International orthopaedics. 2014, Lou, Journal of orthopaedic research: official publication of the Orthopaedic Research Society. 2001; 19:1199-202), which are not very efficient due to limitations of nuclear entry in non-dividing cells (Tong, Current gene therapy. 2009; 9:495-502), and carry potential risk of mutagenesis. Messenger RNA on the other hand has been successfully applied in several mouse models. Kormann et al. reported raising hematocrit levels after single intramuscular injection of modified murine erythropoietin encoding mRNA and in addition, aerosol application containing surfactant B protein encoding mRNA in a congenital mouse disease model reconditioned large parts of the lung (Kormann, Nature biotechnology. 2011; 29:154-7). Furthermore, human VEGF encoding modified mRNA improved heart function and long-term survival in a mouse model of myocardial infarction (Zangi, Nature biotechnology. 2013; 31:898-907). In the context of the invention a focus was set on application of chemically modified naked mRNA (cmRNA) in intact as well as in surgically and chemically injured tendons.

Chemically modified mRNAs represent a novel platform technology for transfecting tissues and consequently expressing therapeutic proteins within the body for the treatment of various pathological conditions (Kormann, Nature biotechnology. 2011; 29:154-7, Zangi, Nature biotechnology. 2013; 31:898-907). It is reported herein for the first time that there is feasibility of using cmRNA technology as a therapeutic approach for effective expression of physiologically active proteins in intact and injured tendons. A self established ex vivo transfection method enabled us to screen transfection efficacy of cmRNA in a variety of species (sheep, cattle, horses, hogs and rats), to optimize transfection conditions and to evaluate expression of several proteins (Luciferase, β-Galactosidase and BMP-7) in a cost efficient and rapid manner. Reporter protein expression was species independent and expression levels were significantly higher when naked cmRNA was applied compared to cmRNA complexed with common lipid and polymer carriers. Furthermore, transgene expression could be optimized when using naked mRNA dissolved in glucose-containing solvents, which could possibly be explained by nutrition effects as tendons are poorly provided with blood due to the low incidence of blood vessels.

Results of our ex vivo studies were confirmed in vivo in intact rat Achilles tendons and subsequently in a Achilles tendon injury model of dissected and surgically repaired Achilles tendons in rats as well as in a collagenase-gel induced tendon defect model in sheep. Injection of cmRNA$^{LUC}$ into healthy tendons resulted in considerable Luciferase expression, peaking after 24 hours and fading out within 7 days in a dose-dependent manner. These observations resembled expression kinetics observed in our ex vivo studies. Injection of cmRNA$^{BMP-7}$ into injured Achilles tendons in turn, resulted in a BMP-7 expression pattern with proceedingly increasing BMP-7 levels up to day 7. Additionally certain background expression of BMP-7 was detected in healthy rat tendons ex vivo and in vivo, as the antibody used cross reacted with endogenous rat BMP-7. Furthermore, expression of endogenous BMP-7 was strongly increased, due to the surgical procedure during rat Achilles tenotomy. Indeed increased expression of BMP-7 as a consequence to harming insults on tendons has already been described by others in various animal studies and patient derived tissue specimen of tendinopathic tendons (Eliasson, Clinical orthopaedics and related research. 2008; 466:1592-7, Yee, Journal of orthopaedic research: official publication of the Orthopaedic Research Society. 2011; 29:816-21, Rui, Knee surgery, sports traumatology, arthroscopy: official journal of the ESSKA. 2012; 20:1409-17, Yu, Arthroscopy: the journal of arthroscopic & related surgery: official publication of the Arthroscopy Association of North America and the International Arthroscopy Association. 2007; 23:205-10, Lui, BMC musculoskeletal disorders. 2013; 14:248). However, a trend of increased BMP-7 expression was observed in tendons being treated with cmRNA$^{BMP-7}$ compared to tendons being treated with vehicle at all points of time after injury. Therefore it was reasoned that injecting cmRNA$^{BMP-7}$ can contribute to increased and prolonged BMP-7 expression in injured tendons.

Increased catabolism of collagen type I is considered to be a critical parameter in the inflammatory and early proliferative phase (day 1 to day 7 post injury) of tendon healing, though strong decrease of collagen type I is suspected to be associated with increased formation of non-functional scar tissue, instead of functional tendon tissue (Sharma, The surgeon: journal of the Royal Colleges of Surgeons of Edinburgh and Ireland. 2005; 3:309-16, Loiselle, PloS one. 2012; 7:e40602). In contrast, collagen type III is associated with characteristics of scar-like tissue, namely loss of tensile strength and elasticity compared to intact tendon tissue (Sharma, Foot and ankle clinics. 2005; 10:383-97). A preferably small content of collagen type III is therefore desirable. In our present study, a tendency of collagen type I catabolism in the vehicle group until day 2 post-surgery was detected, whereas the collagen type I content in tendons being treated with cmRNA$^{BMP-7}$ remained stable during the whole experiment. A strong increase in collagen type III content was observed in the vehicle group from day 2 to day 7 post-surgery, while in tendons being treated with cmRNA$^{BMP-7}$ the increase was less prominent. Consequently, a trend towards a higher ratio of collagen type I to collagen type III was detected in cmRNA$^{BMP-7}$ treated tendons. The histopathological assessment revealed an increased cellular infiltration in cmRNA$^{BMP-7}$ treated animals at day 1 post injury. However no differences regarding inflammation and callus formation became apparent after day 2 and day 7.

Taking these findings together, cmRNA$^{BMP}$-7-induced expression of physiologically functional BMP-7 protein apparently supports tendon healing, through more cellular infiltration and less fulminant collagen III formation. In principle, our present results provide insights into the early healing phase of acute Achilles tendon injury in rats. However, long term studies could be conducted to further clarify, whether cmRNA$^{BMP-7}$ intervention at early time points would be beneficial in all phases of the entire healing process. Although opinions might be discordant as to the question whether BMP-7 enhances tendon healing or impairs it by inducing heterotopic ossification or cartilage formation (Yeh, Journal of cellular biochemistry. 2008; 104:2107-22, Yee, Journal of orthopaedic research: official publication of the Orthopaedic Research Society. 2011; 29:816-21, Forslund, Acta orthopaedica Scandinavica. 1998; 69:622-6, Lui, Rheumatology (Oxford, England). 2013; 52:2116-26), the findings provided herein suggest that overexpression of BMP-7 during the inflammatory phase of tendon regeneration positively influences healing, due to chemotactic attraction of cells, less pronounced collagen type I degradation and decreased collagen type III formation.

Tendon rupture can occur spontaneously, and patients might not have suffered from symptoms before (Kvist, Sports medicine (Auckland, NZ). 1994; 18:173-201, Jozsa, Champaign, Ill.: Human Kinetics; 1997). Degenerative processes are thought to be responsible, which may lead to an altered structure in tendinopathic tissue compared to intact tendons (Riley, Matrix biology: journal of the International Society for Matrix Biology. 2002; 21:185-95). Transformed tissue is characterized by disintegration of collagen fibers, loss of matrix organization and at most mild inflammatory processes in chronic stages (Pecina, Acta chirurgiae orthopaedicae et traumatologiae Cechoslovaca. 2010; 77:277-83). One explanation for this kind of degeneration might be an upregulation of collagenolytic enzymes, such as specific matrix metalloproteinases (MMPs), as it has been detected in chronically altered tendinopathic tendons of humans and animals (Castagna, Muscles, ligaments and tendons journal. 2013; 3:132-8, Jones, Arthritis and rheumatism. 2006; 54:832-42, Muir, Veterinary Surgery. 2005; 34:482-90, Nomura, J Vet Med Sci. 2007; 69:637-9). Similar MMP expression patterns had also been observed in experimentally affected tendons by collagenase-gel injection in horses (Watts, Equine veterinary journal. 2012; 44:576-86). However, in human and veterinary medicine, patients are often presented with symptoms such as pain and discomfort, at a clinical stage before tendons are ruptured. In cases of overuse this symptoms probably result from microtraumatic fiber disruption and subsequent inflammation (Kannus, Scandinavian journal of medicine & science in sports. 1997; 7:78-85). Based on these assumptions a defect model with partial failure could be generated with injection of 100 CDU, imitating clinical characteristics of preliminary stages of tendinopathies in humans and horses. It has to be mentioned that defects induced by 200 CDU or 500 CDU caused a detrimental pathology, which is not considered to represent the clinical situation.

From the herein disclosed ex vivo experiments using β-galactosidase encoding cmRNA it can be seen that transgene expression is distributed tube-like, within fibrils in healthy specimen. Thus it was reasoned, whether this distribution pattern would be the same in pathologically altered tendons, with disintegrated fiber structure due to prior collagenase injection. To clarify this question, cmRNA$^{LUC}$ was injected into injured regions of tendons in a highly translational sheep model of tendonitis. Indeed it was observed in tendons treated with 100 CDU, that transfection efficacy in injured tendons reached equal levels as in intact tendons. Moreover, transgene expression was more widely distributed and intensive in injured tendons. Without being bound by theory, this observation is most likely due to an increased cell number and a raised metabolic activity in injured tendons as compared to intact tendon. Another possible explanation, but again without being bound by theory, could be the circumstance that parts of the extracellular matrix were disintegrated in injured tendons and as a consequence, connections between fibers were loosened. Indeed injected cmRNA may spread more widely between fibers and therefore reached a larger number of cells.

With respect to biological compatibility, intact tendons were examined histopathologically 24 hours after injection of cmRNA$^{Luc}$. The examination showed only a mild unspecific inflammatory reaction near the injection site. It can't be excluded that the cmRNA itself, the expressed protein, mechanical stress due to volume injection, or trauma caused by needle insertion, induced a mild unspecific local immune response, however. Liver and kidney test values as well as full blood count were conducted to investigate cmRNA's pharmaceutical safety in large animals after local application into tendons. In our short term studies mRNA did not lead to organ damage in liver or kidney and did not relevantly affect the immune system as determined values remained within the physiological range 24 hours after cmRNA application or have already slightly differed beforehand. It is readily possible to evaluate mRNA's therapeutic potential in chemically disintegrated tendons by application of cmRNA encoding for therapeutic proteins in an established defect model with partial failure as, for example, disclosed herein.

These results indicate that cmRNAs has the potential as a novel pro-drug, which could be used for expressing therapeutic proteins in injured tendons. Further long-term investigations can be made on the therapeutic potential, of, for example, BMP-7, for the treatment of tendon disorders.

The present invention refers to the following supplemental Tables:

TABLE 2

Solutions used for cmRNA dilution. A selection of primary ingredients is listed.

| Description | Label | Primary Ingredients |
|---|---|---|
| Nitrogen compound containing | Ammonium acetate solution[1] | Ammonium acetate |
| | Aminosteril plus[1] | Total aminoacids 100 g/l, K, Ca, Mg, Cl, Phosphate, Acetate |
| | Aminoven 15%[1] | Total aminoacids 150 g/l |
| Colloidal solutions | HAES steril 10%[1] | Hydroxyethyl starch 100 g/l, Na, Cl |
| | Gelafundin 4%[1] | Gelatine polysuccinate 40 g/l, Na, Cl |
| | HEPES buffered glucose 2.5%[2] | 12.5 mM HEPES, Glucose 25 g/l |
| Glucose containing | HEPES buffered glucose 3.75%[2] | 18.75 mM HEPES, Glucose 37.5 g/l |
| | HEPES buffered glucose 5%[2] | 25 mM HEPES, Glucose 50 g/l |
| | HEPES buffered glucose 10%[2] | 50 mM HEPES, Glucose 100 g/l |
| | Isotonic saline (NaCl)[2] | Glucose, Na, Cl |
| Elektrolyte containing | Ringer acetate[1] | Na, K, Ca, Mg, Cl, Acetate |
| | Ringer lactate[1] | Na, K, Ca, Cl, Lactate |
| Elektrolyte and glucose containing | Isotonic saline + 5% glucose[2] (NaCl + 5% Gluc) | Glucose 50 g/l, Na, Cl |

[1] commercially available,
[2] standard chemical solutions made in-house, HEPES: 2-(4-(2-hydroxyethyl)-1-piperazinethansulfonic acid.

TABLE 3

Analysis of blood count and organ test values.

| | | 400 µg | | | 800 µg | | | 1000 µg | | |
|---|---|---|---|---|---|---|---|---|---|---|
| | amount of cmRNA | d 0 | d 6 | d 7 | d 0 | d 6 | d 7 | d 0 | d 6 | d 7 |
| Blood count | WBC [G/l][1] | 7.4 ± 2.0 | 6.2 ± 0.6 | 7.6* | 6.8* | 5.2 ± 0.5 | 6.1 ± 0.6 | 4.2 ± 0.2 | 3.6 ± 0.1 | 4.2 ± 0.7 |
| | HCT [%][2] | 48.3 ± 3.3 | 51.7 ± 4.2 | 43.9* | 41.5 ± 0.7 | 35.5 ± 2.1 | 40.0 ± 1.4 | 29.5 ± 6.4 | 29.0 ± 4.2 | 36.0 ± 0.0 |
| | PLT [G/L][3] | 409* | 500 ± 87 | 461* | 450 ± 152 | 554 ± 192 | 562 ± 172 | 521 ± 52 | 421 ± 25 | 564 ± 43 |
| Kidney | blood urea nitrogen [mg/dl][4] | 21* | 11 ± 0.0 | 7.5 ± 0.7 | 17 ± 4.2 | 13.5 ± 3.5 | 6 ± 0.7 | 14 ± 1.4 | 12 ± 2.8 | 7.5 ± 2.1 |
| | Creatinine [mg/dl][5] | 1.1* | 1.0 ± 0.0 | 1.1 ± 0.1 | 1.1 ± 0.1 | 1.2 ± 0.3 | 1.1 ± 0.0 | 0.8 ± 0.1 | 0.7 ± 0.0 | 0.7 ± 0.1 |
| Liver | alkaline phosphatase (AP) [U/l][6] | 79* | 61 ± 5 | 49 ± 9 | 102 ± 38 | 88 ± 34 | 89 ± 47 | 69 ± 21 | 74 ± 36 | 89 ± 63 |
| | aspartate aminotransferase (AST) [U/l][7] | 109* | 161 ± 23 | 152 ± 21 | 99 ± 21 | 177 ± 55 | 139 ± 10 | 81 ± 6 | 78 ± 13 | 92 ± 35 |
| | γ-glutamyltransferase (γ-GT) [U/l][8] | 75* | 68 ± 5.7 | 61 ± 5.7 | 73 ± 11 | 78 ± 21 | 65 ± 1 | 63 ± 6.4 | 59 ± 4.2 | 57 ± 3.5 |
| | glutamate dehydrogenase (GLDH) [U/l][9] | 3* | 4.5 ± 2.1 | 7 ± 4.2 | 6 ± 1.4 | 3.5 ± 0.7 | 3 ± 0.0 | 6.5 ± 0.7 | 6.5 ± 3.5 | 6.5 ± 3.5 |
| | bile acids [µmol/l][10] | 4.3* | 8.6 ± 10.5 | 12.4 ± 6.9 | 12 ± 9.5 | 2.7 ± 1.8 | 10.4 ± 7.6 | 4.5 ± 3.5 | 4.6 ± 4.2 | 26.6 ± 26.4 |
| | total bilirubin [mg/dl][11] | 0.3* | 0.3 ± 0.1 | 0.4 ± 0.0 | 0.2 ± 0.0 | 0.35 ± 0.1 | 0.2 ± 0.0 | 0.3 ± 0.1 | 0.25 ± 0.1 | 40.2 ± 0.0 |
| | serum albumin [g/dl][12] | 3.8* | 3.7 ± 0.4 | 3.5 ± 0.2 | 3.7 ± 0.5 | 3.8 ± 0.8 | 3.2 ± 0.1 | 3.1 ± 0.3 | 2.9 ± 0.3 | 2.9 ± 0.2 |

Results are presented as the mean ± SD (n = 2, *n = 1).
Reference ranges:
[1] 4-11 G/l,
[2] 27-40%,
[3] 280-650 G/l,
[4] 5-11 mg/dl,
[5] <1.9 mg/dl,
[6,7] <180 U/l,
[8] <32 U/l,
[9] <9 U/l,
[10] postprandial < 40 µmol/l,
[11] <0.4 mg/dl,
[12] 2-3 g/dl.

The present invention refers to the following nucleotide sequences:

SEQ ID NO. 1:
Nucleotide sequence encoding *Homo sapiens* bone morphogenetic protein 7 (BMP7)
Pubmed accession number: NM_001719
Version: NM_001719.2 GI:187608319
AGCGCGTACCACTCTGGCGCTCCCGAGGCGGCCTCTTGTGCGATCCAGGGCGCACAAGGCTGGGAGAGCGCCCCG

GGGCCCCTGCTATCCGCGCCGGAGGTTGGAAGAGGGTGGGTTGCCGCCGCCCGAGGGCGAGAGCGCCAGAGGAGC

GGGAAGAAGGAGCGCTCGCCCGCCCGCCTGCCTCCTCGCTGCCTCCCCGGCGTTGGCTCTCTGGACTCCTAGGCT

TGCTGGCTGCTCCTCCCACCCGCGCCCGCCTCCTCACTCGCCTTTTCGTTCGCCGGGGCTGCTTTCCAAGCCCTG

CGGTGCGCCCGGGCGAGTGCGGGGCGAGGGGCCCGGGGCCAGCACCGAGCAGGGGGCGGGGTCCGGGCAGAGCG

CGGCCGGCCGGGGAGGGGCCATGTCTGGCGCGGGCGCAGCGGGGCCCGTCTGCAGCAAGTGACCGAGCGGCGCGG

ACGGCCGCCTGCCCCCTCTGCCACCTGGGGCGGTGCGGGCCCGGAGCCCGGAGCCCGGGTAGCGCGTAGAGCCGG

CGCGATGCACGTGCGCTCACTGCGAGCTGCGGCGCCGCACAGCTTCGTGGCGCTCTGGGCACCCCTGTTCCTGCT

GCGCTCCGCCCTGGCCGACTTCAGCCTGGACAACGAGGTGCACTCGAGCTTCATCCACCGGCGCCTCCGCAGCCA

GGAGCGGCGGGAGATGCAGCGCGAGATCCTCTCCATTTTGGGCTTGCCCCACCGCCCGCGCCCGCACCTCCAGGG

CAAGCACAACTCGGCACCCATGTTCATGCTGGACCTGTACAACGCCATGGCGGTGGAGGAGGGCGGCGGGCCCGG

CGGCCAGGGCTTCTCCTACCCCTACAAGGCCGTCTTCAGTACCCAGGGCCCCCCTCTGGCCAGCCTGCAAGATAG

CCATTTCCTCACCGACGCCGACATGGTCATGAGCTTCGTCAACCTCGTGGAACATGACAAGGAATTCTTCCACCC

ACGCTACCACCATCGAGAGTTCCGGTTTGATCTTTCCAAGATCCCAGAAGGGGAAGCTGTCACGGCAGCCGAATT

CCGGATCTACAAGGACTACATCCGGGAACGCTTCGACAATGAGACGTTCCGGATCAGCGTTTATCAGGTGCTCCA

GGAGCACTTGGGCAGGGAATCGGATCTCTTCCTGCTCGACAGCCGTACCCTCTGGGCCTCGGAGGAGGGCTGGCT

GGTGTTTGACATCACAGCCACCAGCAACCACTGGGTGGTCAATCCGCGGCACAACCTGGGCCTGCAGCTCTCGGT

GGAGACGCTGGATGGGCAGAGCATCAACCCCAAGTTGGCGGGCCTGATTGGGCGGCACGGGCCCCAGAACAAGCA

GCCCTTCATGGTGGCTTTCTTCAAGGCCACGGAGGTCCACTTCCGCAGCATCCGGTCCACGGGGAGCAAACAGCG

CAGCCAGAACCGCTCCAAGACGCCCAAGAACCAGGAAGCCCTGCGGATGGCCAACGTGGCAGAGAACAGCAGCAG

CGACCAGAGGCAGGCCTGTAAGAAGCACGAGCTGTATGTCAGCTTCCGAGACCTGGGCTGGCAGGACTGGATCAT

CGCGCCTGAAGGCTACGCCGCCTACTACTGTGAGGGGGAGTGTGCCTTCCCTCTGAACTCCTACATGAACGCCAC

CAACCACGCCATCGTGCAGACGCTGGTCCACTTCATCAACCCGGAAACGGTGCCCAAGCCCTGCTGTGCGCCCAC

GCAGCTCAATGCCATCTCCGTCCTCTACTTCGATGACAGCTCCAACGTCATCCTGAAGAAATACAGAAACATGGT

GGTCCGGGCCTGTGGCTGCCACTAGCTCCTCCGAGAATTCAGACCCTTTGGGGCCAAGTTTTTCTGGATCCTCCA

TTGCTCGCCTTGGCCAGGAACCAGCAGACCAACTGCCTTTTGTGAGACCTTCCCCTCCCTATCCCCAACTTTAAA

GGTGTGAGAGTATTAGGAAACATGAGCAGCATATGGCTTTTGATCAGTTTTTCAGTGGCAGCATCCAATGAACAA

GATCCTACAAGCTGTGCAGGCAAAACCTAGCAGGAAAAAAAAACAACGCATAAAGAAAAATGGCCGGGCCAGGTC

ATTGGCTGGGAAGTCTCAGCCATGCACGGACTCGTTTCCAGAGGTAATTATGAGCGCCTACCAGCCAGGCCACCC

AGCCGTGGGAGGAAGGGGCGTGGCAAGGGGTGGGCACATTGGTGTCTGTGCGAAAGGAAAATTGACCCGGAAGT

TCCTGTAATAAATGTCACAATAAAACGAATGAATGAAAATGGTTAGGACGTTACAGATATATTTTCCTAAACAAT

TTATCCCCATTTCTCGGTTTATCCTGATGCGTAAACAGAAGCTGTGTCAAGTGGAGGGCGGGGAGGTCCCTCTCC

ATTCCCTACAGTTTTCATCCTGAGGCTTGCAGAGGCCCAGTGTTTACCGAGGTTTGCCCAAATCCAAGATCTAGT

GGGAGGGGAAAGAGCAAATGTCTGCTCCGAGGAGGGCGGTGTGTTGATCTTTGGAGGAAAAATATGTTCTGTTGT

TCAGCTGGATTTGCCGTGGCAGAAATGAAACTAGGTGTGTGAAATACCCGCAGACATTTGGGATTGGCTTTTCAC

CTCGCCCCAGTGGTAGTAAATCCATGTGAAATTGCAGAGGGGACAAGGACAGCAAGTAGGATGGAACTTGCAACT

CAACCCTGTTGTTAAGAAGCACCAATGGGCCGGGCACAGTAGCTCCCACCTGTAATCCCAGCACTTTGGGAGGCT

-continued

```
GAGGTGGGCGGATCATTTGAGGTCAGGAGTTCGAGACCAGCCTGGCCAACATGGTGAAACCCCATCTCTACTAAA

AATACAAAAATTAGCCGGGCATGGTGGCACGCACCTGTAATCCCAGCTACTCTGGAGGCTGAGGCAGGAGAATTG

CTTGAACCCCAGAGGTGGAGGTTGCAGTGAGCCAAGATCGTCCCACTGCACTCCAGCTTGGGTGACAAAACAAGA

CTCCATCTCAAAAGAAAAAAAAAACAGCACCAATGAAGCCTAGTTCTCCACGGGAGTGGGGTGAGCAGGAGCACT

GCACATCGCCCCAGTGGACCCTCTGGTCTTTGTCTGCAGTGGCATTCCAAGGCTGGGCCCTGGCAAGGGCACCCG

TGGCTGTCTCTTCATTTGCAGACCCTGATCAGAAGTCTCTGCAAACAAATTTGCTCCTTGAATTAAGGGGGAGAT

GGCATAATAGGAGGTCTGATGGGTGCAGGATGTGCTGGACTTACATTGCAAATAGAAGCCTTGTTGAGGGTGACA

TCCTAACCAAGTGTCCCGATTTGGAGGTGGCATTTCTGACGTGGCTCTTGGTGTAAGCCTGCCTTGCCTTGGCTG

GTGAGTCCCATAAATAGTATGCACTCAGCCTCCGGCCACAAACACAAGGCCTAGGGGAGGGCTAGACTGTCTGCA

AACGTTTTCTGCATCTGTAAAGAAAACAAGGTGATCGAAAACTGTGGCCATGTGGAACCCGGTCTTGTGGGGGAC

TGTTTCTCCATCTTGACTCAGACAGTTCCTGGAAACACCGGGGCTCTGTTTTTATTTTCTTTGATGTTTTTCTTC

TTTAGTAGCTTGGGCTGCAGCCTCCACTCTCTAGTCACTGGGGAGGAGTATTTTTTGTTATGTTTGGTTTCATTT

GCTGGCAGAGCTGGGGCTTTTTGTGTGATCCCTCTTGGTGTGAGTTTTCTGACCCAACCAGCCTCTGGTTAGCAT

CATTTGTACATTTAAACCTGTAAATAGTTGTTACAAAGCAAAGAGATTATTTATTTCCATCCAAAGCTCTTTTGA

ACACCCCCCCCCTTTAATCCCTCGTTCAGGACGATGAGCTTGCTTTCCTTCAACCTGTTTGTTTTCTTATTTAA

GACTATTTATTAATGGTTGGACCAATGTACTCACAGCTGTTGCGTCGAGCAGTCCTTAGTGAAAATTCTGTATAA

ATAGACAAAATGAAAAGGGTTTGACCTTGCAATAAAAGGAGACGTTTGGTTCTGGCAAAAAAAAAAAAAAAAAA
```

ORF (underlined) from the above sequence may be codon optimized (e.g. by Eurofins).

SEQ ID NO. 2:
Codon optimized mRNA sequence (DNA Format) resulting from the above SEQ ID NO. 1
```
GGGAGACCCAAGCTGGCTAGCGTTTAAACTTAAGCTTGGTACCGAGCTCGGATCCATGCACGTACGCAGTCTTAGGGCTGC

TGCCCCACACAGCTTTGTGGCCCTGTGGGCACCCCTCTTTCTGCTTAGGTCTGCTCTTGCCGACTTTTCACTGGA

CAACGAGGTCCATTCCTCATTTATCCACCGTCGACTGAGAAGCCAAGAGAGGCGGGAAATGCAGCGCGAGATTTT

GTCTATCCTGGGATTGCCCCATAGACCTCGTCCCCATCTCCAAGGGAAACACAACTCTGCTCCCATGTTCATGCT

GGATCTGTACAATGCCATGGCAGTGGAGGAAGGTGGTGGCCCAGGAGGACAGGGCTTCTCCTATCCGTACAAGGC

CGTCTTTTCCACCCAAGGTCCACCGTTGGCGAGTCTCCAGGATTCCCATTTCCTGACCGATGCGGACATGGTGAT

GTCATTCGTGAACCTGGTGGAACACGACAAAGAGTTCTTTCACCCCAGGTATCACCACAGAGAGTTCCGCTTCGA

CTTGAGTAAATCCCTGAGGGAGAAGCCGTTACTGCCGCCGAGTTTCGCATTTACAAGGACTACATTCGGGAGAG

GTTCGATAACGAAACCTTCCGGATATCCGTGTATCAGGTGCTGCAAGAGCATCTGGGGAGAGAGTCCGATCTCTT

CCTCCTGGACAGTAGGACACTGTGGGCGTCTGAGGAAGGCTGGCTTGTGTTCGACATAACTGCCACGAGCAATCA

CTGGGTTGTAAACCCAAGGCATAACCTGGGGCTTCAGCTGTCTGTCGAGACACTGGATGGGCAGAGCATCAATCC

CAAACTGGCTGGGTTGATCGGACGCCATGGTCCACAGAACAAACAGCCTTTCATGGTAGCTTTCTTTAAGGCCAC

AGAAGTGCACTTTCGGAGTATTCGGAGCACTGGCAGCAAACAGAGAAGCCAGAATAGATCCAAGACCCCTAAGAA

TCAGGAAGCCCTGCGGATGGCAAATGTGGCGGAGAATAGCAGCTCAGATCAGAGACAGGCTTGCAAGAAGCATGA

ACTGTATGTGTCTTTTCGAGATCTCGGATGGCAGGACTGGATTATCGCACCAGAGGGCTATGCTGCCTACTATTG

CGAAGGCGAGTGCGCATTTCCTCTGAACAGCTACATGAACGCAACCAATCATGCCATTGTCCAAACACTCGTTCA

CTTCATCAATCCGGAAACTGTGCCTAAACCCTGTTGTGCACCTACGCAGCTGAACGCTATATCTGTTCTGTACTT

TGACGATTCATCCAACGTCATCCTCAAGAAGTACCGCAATATGGTTGTCCGAGCATGCGGCTGTCACTGA
```
GAATTC

*CTGCAGAAAAAAAAAAAAAAAAAAAAAAAAAAAAAAAAAAAAAAAAAAAAAAAAAAAAAAAAAAAAAAAAAAAAA*

*AAAAAAAAAAAAAAAAAAAAAAAAAAAAAAAAAAAAAAAAAAA*GCGGCC

Large capital letters represent the BMP-7 ORF.

SEQ ID NO. 3:

-continued cmRNA sequence (RNA Format) resulting from the above SEQ ID NO. 1
GGGAGACCCAAGCUGGCUAGCGUUUAAACUUAAGCUUGGUACCGAGCUCGGAUCCAUGCACGUACGCAGUCUUAGGGCUGC

UGCCCCACACAGCULUGUGGCCCUGUGGGCACCCCUCUUUCIJGCEUAGGUCUGCUCUUGCCGACULUUCACUGGA

CAACGAGGUCCAUUCCUCAUUUAUCCACCGUCGACUGAGAAGCCAAGAGAGGCGGGAAAUGCAGCGCGAGAUUUU

GUCUAUCCUGGGAUUGCCCCAUAGACCUCGUCCCCACUCCAAGGGAAACACAACUCUGCUCCCAUGUUCAUGCU

GGAUCUGUACAAUGCCAUGGCAGUGGAGGAAGGUGGUGGCCCAGGAGGACAGGGCUUCUCCUAUCCGUACAAGGC

CGUCUUUUCCACCCAAGGUCCACCGUUGGCGAGUCUCCAGGAUUCCCAUUUCCUGACCGAUGCGGACAUGGUGAU

GUCAUUCGUGAACCUGGUGGAACACGACAAAGAGUUCUUUCACCCCAGGUAUCACCACAGAGAGUUCCGCUUCGA

CUUGAGUAAAAAUCCCUGAGGGAGAAGCCGUUACUGCCGCCGAGUUUCGCAUUUACAAGGACUACAUUCGGGAGAG

GUUCGAUAACGAAACCUUCCGGAUAUCCGUGUAUCAGGUGCUGCAAGAGCAUCUGGGGAGAGAGUCCGAUCUCUU

CCUCCUGGACAGUAGGACACUGUGGGCGUCUGAGGAAGGCUGGCUUGUGUUCGACAUAACUGCCACGAGCAAUCA

CUGGGUUGUAAACCCAAGGCAUAACCUGGGGCUUCAGCUGUCUGUCGAGACACUGGAUGGGCAGAGCAUCAAUCC

CAAACUGGCUGGGUUGAUCGGACGCCAUGGUCCACAGAACAAACAGCCUUUCAUGGUAGCUUUCUUUAAGGCCAC

AGAAGUGCACUUUCGGAGUAUUCGGAGCACUGGCAGCAAACAGAGAAGCCAGAAUAGAUCCAAGACCCCUAAGAA

UCAGGAAGCCCUGCGGAUGGCAAAUGUGGCGGAGAAUAGCAGCUCAGAUCAGAGACAGGCUUGCAAGAAGCAUGA

ACUGUAUGUGUCUUUUCGAGAUCUCGGAUGGCAGGACUGGAUUAUCGCACCAGAGGGCUAUGCUGCCUACUAUUG

CGAAGGCGAGUGCGCAUUUCCUCUGAACAGCUACAUGAACGCAACCAAUCAUGCCAUUGUCCAAACACUCGUUCA

CUUCAUCAAUCCGGAAACUGUGCCUAAACCCUGUUGUGCACCUACGCAGCUGAACGCUAUAUCGUUCUGUACUU

UGACGAUUCAUCCAACGUCAUCCUCAAGAAGUACCGCAAUAUGGUUGUCCGAGCAUGCGGCUGUCACUGA*GAAUUC*

*CUGCAGAAAAAAAAAAAAAAAAAAAAAAAAAAAAAAAAAAAAAAAAAAAAAAAAAAAAAAAAAAAAAAAAAAAAA*

*AAAAAAAAAAAAAAAAAAAAAAAAAAAAAAAAAAAAAAAAAGCGGCC*

Large capital letters represent the BMP-7 ORF.

---

The invention claimed is:

1. A liquid composition containing naked RNA, wherein the RNA is solved in a glucose solution, and wherein the RNA is mRNA encoding a polypeptide selected from the group consisting of epidermal growth factor (EGF), platelet-derived growth factor (PDGF), basic fibroblast growth factor (bFGF), insulin-like growth factor 1 (IGF-1), transforming growth factor β1 (TGF-β1), a growth and differentiation factor (GDF), Vegf, and bone morphogenetic protein (BMP).

2. The composition of claim 1, wherein the polypeptide is a polypeptide which is therapeutically active in the healing process of ligament or tendon.

3. The composition of claim 1, wherein the buffered glucose solution is a HEPES buffered glucose solution.

4. The composition of claim 1, wherein the concentration of the RNA in the composition is between 0.1 to 5.0 µg/µl.

5. The composition of claim 1, wherein the composition is administered to a ligament or tendon by injection.

6. The composition of claim 5, wherein the injection is done by a syringe with a needle having a diameter in the range of 20 G to 27 G.

7. The composition of claim 1, wherein the GDF is GDF 5, 6 (BMP-13), 7 (BMP-12), myostatin (GDF-8).

8. The composition of claim 1, wherein the BMP is BMP-7.

9. The composition for use of claim 1, wherein said liquid composition is to be administered before or during the inflammatory phase which follows the said ligament or tendon lesions.

* * * * *

SEQUENCE LISTING

<160> NUMBER OF SEQ ID NOS: 3

<210> SEQ ID NO 1
<211> LENGTH: 4049
<212> TYPE: DNA
<213> ORGANISM: Homo sapiens

<400> SEQUENCE: 1

| | | | | | |
|---|---|---|---|---|---|
| agcgcgtacc | actctggcgc | tcccgaggcg | gcctcttgtg | cgatccaggg | cgcacaaggc | 60 |
| tgggagagcg | ccccgggggcc | cctgctatcc | gcgccggagg | ttggaagagg | gtgggttgcc | 120 |
| gccgcccgag | ggcgagagcg | ccagaggagc | gggaagaagg | agcgctcgcc | cgcccgcctg | 180 |
| cctcctcgct | gcctccccgg | cgttggctct | ctggactcct | aggcttgctg | gctgctcctc | 240 |
| ccacccgcgc | ccgcctcctc | actcgccttt | tcgttcgccg | gggctgcttt | ccaagccctg | 300 |
| cggtgcgccc | gggcgagtgc | ggggcgaggg | gcccggggcc | agcaccgagc | aggggggcggg | 360 |
| ggtccgggca | gagcgcggcc | ggccggggag | gggccatgtc | tggcgcgggc | gcagcggggc | 420 |
| ccgtctgcag | caagtgaccg | agcggcgcgg | acggccgcct | gcccctctg | ccacctgggg | 480 |
| cggtgcgggc | ccggagcccg | gagcccgggt | agcgcgtaga | gccggcgcga | tgcacgtgcg | 540 |
| ctcactgcga | gctgcggcgc | cgcacagctt | cgtggcgctc | tgggcacccc | tgttcctgct | 600 |
| gcgctccgcc | ctggccgact | tcagcctgga | caacgaggtg | cactcgagct | tcatccaccg | 660 |
| gcgcctccgc | agccaggagc | ggcgggagat | gcagcgcgag | atcctctcca | ttttgggctt | 720 |

-continued

```
gccccaccgc ccgcgcccgc acctccaggg caagcacaac tcggcaccca tgttcatgct    780
ggacctgtac aacgccatgg cggtggagga gggcggcggg cccggcggcc agggcttctc    840
ctacccctac aaggccgtct tcagtaccca gggccccccct ctggccagcc tgcaagatag    900
ccatttcctc accgacgccg acatggtcat gagcttcgtc aacctcgtgg aacatgacaa    960
ggaattcttc cacccacgct accaccatcg agagttccgg tttgatcttt ccaagatccc   1020
agaaggggaa gctgtcacgg cagccgaatt ccggatctac aaggactaca tccgggaacg   1080
cttcgacaat gagacgttcc ggatcagcgt ttatcaggtg ctccaggagc acttgggcag   1140
ggaatcggat ctcttcctgc tcgacagccg taccctctgg gcctcggagg agggctggct   1200
ggtgtttgac atcacagcca ccagcaacca ctgggtggtc aatccgcggc acaacctggg   1260
cctgcagctc tcggtggaga cgctggatgg gcagagcatc aacccaagt tggcgggcct   1320 gattgggcgg cacgggcccc agaacaagca gcccttcatg gtggctttct tcaaggccac   1380
ggaggtccac ttccgcagca tccggtccac ggggagcaaa cagcgcagcc agaaccgctc   1440
caagacgccc aagaaccagg aagccctgcg gatggccaac gtggcagaga cagcagcag   1500 cgaccagagg caggcctgta agaagcacga gctgtatgtc agcttccgag acctgggctg   1560
gcaggactgg atcatcgcgc tgaaggcta cgccgcctac tactgtgagg gggagtgtgc   1620
cttccctctg aactcctaca tgaacgccac caaccacgcc atcgtgcaga cgctggtcca   1680
cttcatcaac ccggaaacgg tgcccaagcc ctgctgtgcg cccacgcagc tcaatgccat   1740
ctccgtcctc tacttcgatg acagctccaa cgtcatcctg aagaaataca gaaacatggt   1800
ggtccgggcc tgtggctgcc actagctcct ccgagaattc agacccttg gggccaagtt   1860 tttctggatc ctccattgct cgccttggcc aggaaccagc agaccaactg cctttttgtga   1920 gaccttcccc tccctatccc caactttaaa ggtgtgagag tattaggaaa catgagcagc   1980
atatggcttt tgatcagttt ttcagtggca gcatccaatg aacaagatcc tacaagctgt   2040
gcaggcaaaa cctagcagga aaaaaaaaca acgcataaag aaaaatggcc gggccaggtc   2100
attggctggg aagtctcagc catgcacgga ctcgttttcca gaggtaatta tgagcgccta   2160
ccagccaggc cacccagccg tgggaggaag ggggcgtggc aaggggtggg cacattggtg   2220
tctgtgcgaa aggaaaattg acccggaagt tcctgtaata aatgtcacaa taaaacgaat   2280
gaatgaaaat ggttaggacg ttacagatat attttcctaa acaatttatc cccatttctc   2340
ggtttatcct gatgcgtaaa cagaagctgt gtcaagtgga gggcggggag gtccctctcc   2400
attccctaca gttttcatcc tgaggcttgc agaggcccag tgtttaccga ggtttgccca   2460
aatccaagat ctagtgggag gggaaagagc aaatgtctgc tccgaggagg gcggtgtgtt   2520
gatctttgga ggaaaaatat gttctgttgt tcagctggat ttgccgtggc agaaatgaaa   2580
ctaggtgtgt gaaataccccg cagacatttg ggattggctt ttcacctcgc cccagtggta   2640
gtaaatccat gtgaaattgc agaggggaca aggacagcaa gtaggatgga acttgcaact   2700
caaccctgtt gttaagaagc accaatgggc cgggcacagt agctcccacc tgtaatccca   2760
gcactttggg aggctgaggt gggcggatca tttgaggtca ggagttcgag accagcctgg   2820
ccaacatggt gaaaccccat ctctactaaa aatacaaaaa ttagccgggc atggtggcac   2880
gcacctgtaa tcccagctac tctggaggct gaggcaggag aattgcttga ccccagagg   2940 tggaggttgc agtgagccaa gatcgtccca ctgcactcca gcttgggtga caaacaaga   3000 ctccatctca aagaaaaaa aaaacagcac caatgaagcc tagttctcca cgggagtggg   3060
```

```
gtgagcagga gcactgcaca tcgccccagt ggaccctctg gtctttgtct gcagtggcat      3120
tccaaggctg ggccctggca agggcacccg tggctgtctc ttcatttgca gaccctgatc      3180
agaagtctct gcaaacaaat ttgctccttg aattaagggg gagatggcat aataggaggt      3240
ctgatgggtg caggatgtgc tggacttaca ttgcaaatag aagccttgtt gagggtgaca      3300
tcctaaccaa gtgtcccgat ttggaggtgg catttctgac gtggctcttg gtgtaagcct      3360
gccttgcctt ggctggtgag tcccataaat agtatgcact cagcctccgg ccacaaacac      3420
aaggcctagg ggagggctag actgtctgca acgttttct gcatctgtaa agaaaacaag       3480
gtgatcgaaa actgtggcca tgtggaaccc ggtcttgtgg gggactgttt ctccatcttg      3540
actcagacag ttcctggaaa caccggggct ctgtttttat tttctttgat gttttcttc       3600 tttagtagct tgggctgcag cctccactct ctagtcactg ggaggagta ttttttgtta       3660 tgtttggttt catttgctgg cagagctggg gcttttgtg tgatccctct tggtgtgagt       3720
tttctgaccc aaccagcctc tggttagcat catttgtaca tttaaacctg taaatagttg      3780
ttacaaagca aagagattat ttatttccat ccaaagctct tttgaacacc ccccccctt       3840 taatccctcg ttcaggacga tgagcttgct ttccttcaac ctgtttgttt tcttatttaa      3900
gactatttat taatgttggg accaatgtac tcacagctgt tgcgtcgagc agtccttagt      3960
gaaaattctg tataaataga caaaatgaaa agggtttgac cttgcaataa aaggagacgt      4020
ttggttctgg caaaaaaaaa aaaaaaaaa                                        4049

<210> SEQ ID NO 2
<211> LENGTH: 1489
<212> TYPE: DNA
<213> ORGANISM: Artificial Sequence
<220> FEATURE:
<223> OTHER INFORMATION: codon optimized mRNA sequence (DNA format)
      encoding BMP-7

<400> SEQUENCE: 2
gggagaccca agctggctag cgtttaaact taagcttggt accgagctcg gatccatgca       60
cgtacgcagt cttagggctg ctgccccaca cagctttgtg gccctgtggg cacccctctt      120
tctgcttagg tctgctcttg ccgactttc actggacaac gaggtccatt cctcatttat       180
ccaccgtcga ctgagaagcc aagagaggcg ggaaatgcag cgcgagattt tgtctatcct      240
gggattgccc catagacctc gtccccatct ccaagggaaa cacaactctg ctcccatgtt      300
catgctggat ctgtacaatg ccatggcagt ggaggaaggt ggtggcccag gaggacaggg      360 cttctccctat ccgtacaagg ccgtcttttc cacccaaggt ccaccgttgg cgagtctcca     420
ggattcccat ttcctgaccg atgcggacat ggtgatgtca ttcgtgaacc tggtggaaca      480
cgacaaagag ttctttcacc ccaggtatca ccacagagag ttccgcttcg acttgagtaa      540
aatccctgag ggagaagccg ttactgccgc cgagtttcgc atttacaagg actacattcg      600
ggagaggttc gataacgaaa ccttccggat atccgtgtat caggtgctgc aagagcatct      660
ggggagagag tccgatctct tcctcctgga cagtaggaca ctgtgggcgt ctgaggaagg      720
ctggcttgtg ttcgacataa ctgccacgag caatcactgg gttgtaaacc caaggcataa      780 cctgggggctt cagctgtctg tcgagacact ggatgggcag agcatcaatc ccaaactggc     840
tgggttgatc ggacgccatg tccacagaa caaacagcct ttcatggtag ctttctttaa       900
ggccacagaa gtgcactttc ggagtattcg gagcactggc agcaaacaga aagccagaa       960 tagatccaag acccctaaga atcaggaagc cctgcggatg gcaaatgtgg cggagaatag     1020
```

-continued

| | |
|---|---|
| cagctcagat cagagacagg cttgcaagaa gcatgaactg tatgtgtctt ttcgagatct | 1080 |
| cggatggcag gactggatta tcgcaccaga gggctatgct gcctactatt gcgaaggcga | 1140 |
| gtgcgcattt cctctgaaca gctacatgaa cgcaaccaat catgccattg tccaaacact | 1200 |
| cgttcacttc atcaatccgg aaactgtgcc taaaccctgt tgtgcaccta cgcagctgaa | 1260 |
| cgctatatct gttctgtact tgacgattc atccaacgtc atcctcaaga agtaccgcaa | 1320 |
| tatggttgtc cgagcatgcg gctgtcactg agaattcctg cagaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaagcggcc | 1489 |

<210> SEQ ID NO 3
<211> LENGTH: 1489
<212> TYPE: RNA
<213> ORGANISM: Artificial Sequence
<220> FEATURE:
<223> OTHER INFORMATION: codon optimized mRNA sequence (RNA format)
    encoding BMP-7

<400> SEQUENCE: 3

| | |
|---|---|
| gggagaccca agcuggcuag cguuuaaacu uaagcuuggu accgagcucg gauccaugca | 60 |
| cguacgcagu cuuagggcug cugccccaca cagcuuugug gcccugugg caccccucuu | 120 |
| ucugcuuagg ucugcucuug ccgacuuuuc acuggacaac gagguccauu ccucauuuau | 180 |
| ccaccgucga cugagaagcc aagagaggcg ggaaaugcag cgcgagauuu ugucuauccu | 240 |
| gggauugccc cauagaccuc gucccccaucu ccaagggaaa cacaacucug ucccaugu | 300 |
| caugcuggau cuguacaaug ccauggcagu ggaggaaggu gguggcccag gaggacaggg | 360 |
| cuucuccuau ccguacaagg ccgucuuuuc cacccaaggu ccaccguugg cgagucucca | 420 |
| ggauuccau uuccugaccg augcggacau ggugaugca uucgugaacc ugguggaaca | 480 |
| cgacaaagag uucuuucacc ccagguauca ccacagagag uuccgcuucg acuugaguaa | 540 |
| aaucccugag ggagaagccg uuacugccgc cgaguuucgc auuuacaagg acuacauucg | 600 |
| ggagagguuc gauaacgaaa ccuuccggau auccguguau caggugcugc aagagcaucu | 660 |
| ggggagagag uccgaucucu uccuccugga caguaggaca cuguggcgu cugaggaagg | 720 |
| cuggcuugug uucgacauaa cugccacgag caaucacugg guuguaaacc caaggcauaa | 780 |
| ccuggggcuu cagcugucug ucgagacacu ggaugggcag agcaucaauc ccaaacuggc | 840 |
| ugggguugauc ggacgccaug guccacagaa caaacagccu uucaugguag cuuucuuuaa | 900 |
| ggccacagaa gugcacuuuc ggaguauucg gagcacuggc agcaaacaga aagccagaa | 960 |
| uagauccaag accccuaaga aucaggaagc ccugcggaug gcaaugugg cggagaauag | 1020 |
| cagcucagau cagagacagg cuugcaagaa gcaugaacug uaugugucuu uucgagaucu | 1080 |
| cggauggcag gacuggauua ucgcaccaga gggcuaugcu gccuacuauu gcgaaggcga | 1140 |
| gugcgcauuu ccucugaaca gcuacaugaa cgcaaccaau caugccauug uccaaacacu | 1200 |
| cguucacuuc aucaauccgg aaacugugcc uaaacccugu ugugcaccua cgcagcugaa | 1260 |
| cgcuauaucu guucuguacu ugacgauuc auccaacguc auccucaaga aguaccgcaa | 1320 |
| uaugguuguc cgagcaugcg gcugucacug agaauuccug cagaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaagcggcc | 1489 |